(12) United States Patent
Sucheck et al.

(10) Patent No.: US 10,647,725 B2
(45) Date of Patent: May 12, 2020

(54) ANTI-INFECTIVE 2-AMINOTHIOPHENES

(71) Applicants: The University of Toledo, Toledo, OH (US); Colorado State University Research Foundation, Fort Collins, CO (US)

(72) Inventors: Steven Sucheck, Toledo, OH (US); Sandeep Thanna, Toledo, OH (US); Richard Slayden, Fort Collins, CO (US)

(73) Assignees: The University of Toledo, Toledo, OH (US); Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 16/094,770

(22) PCT Filed: Apr. 21, 2017

(86) PCT No.: PCT/US2017/028782
§ 371 (c)(1),
(2) Date: Oct. 18, 2018

(87) PCT Pub. No.: WO2017/184947
PCT Pub. Date: Oct. 26, 2017

(65) Prior Publication Data
US 2019/0119296 A1    Apr. 25, 2019

Related U.S. Application Data

(60) Provisional application No. 62/325,755, filed on Apr. 21, 2016.

(51) Int. Cl.
*C07D 495/04* (2006.01)
*A61P 31/06* (2006.01)

(52) U.S. Cl.
CPC ............ *C07D 495/04* (2013.01); *A61P 31/06* (2018.01)

(58) Field of Classification Search
CPC ..... C07D 495/04; A61P 31/06; A61K 31/435; A61K 31/4365; A61K 31/4427

USPC .......................................................... 514/301
See application file for complete search history.

(56) References Cited

U.S. PATENT DOCUMENTS

| | | | | |
|---|---|---|---|---|
| 7,365,080 | B2 * | 4/2008 | Gregor | A61K 31/4365 514/301 |
| 2007/0275962 | A1 * | 11/2007 | Koul | C07D 209/42 514/233.8 |
| 2016/0362420 | A1 * | 12/2016 | Skouta | C07D 495/04 |

FOREIGN PATENT DOCUMENTS

DE          272 078      * 9/1989

OTHER PUBLICATIONS

Saxena; European Journal of Medicinal Chemistry 2015, 92, 401-414. (Available online Dec. 27, 2014). (Year: 2015).*
National Center for Biotechnology Information. PubChem Database. CID=4415089, https://pubchem.ncbi.nlm.nih.gov/compound/4415089 (accessed on May 8, 2019). Created Sep. 14, 2005. (Year: 2005).*
Thanna; Org. Biomol. Chem., 2016, 14, 6119-6133. Published on May 25, 2016. (Year: 2016).*
Wolpaw; Proceedings of the National Academy of Sciences Sep. 2011, 108 (39) E771-E780; with Supplementary Information. (Year: 2011).*
Chemical Abstracts STN Registry database, record for RN 524064-67-3, entered on Jun. 2, 2003. (Year: 2003).*
Chemical Abstracts STN Registry database, record for RN 924800-78-2, entered on Mar. 5, 2007. (Year: 2007).*
Thanna, S. (2017). Design and Synthesis of Novel Inhibitors for Enzymatic Targets in Trehalose Utilization Pathways of *Mycobacterium tuberculosis*. (Electronic Thesis or Dissertation). Retrieved from https://etd.ohiolink.edu/ (Year: 2017).*
Chemical Abstracts STN Registry database, record for RN 1152984-05-8, entered on Jun. 7, 2009. (Year: 2009).*
Nam; European Journal of Medicinal Chemistry 2015, 97, 245-258. DOI: 10.1016/j.ejmech.2015.04.060 (Year: 2015).*

* cited by examiner

*Primary Examiner* — Daniel R Carcanague
(74) *Attorney, Agent, or Firm* — MacMillan, Sobanski & Todd, LLC

(57) ABSTRACT

2-Aminothiophene derivatives, uses of the same, and methods of making the same, are described.

12 Claims, 60 Drawing Sheets

Ag85C-inhibitors
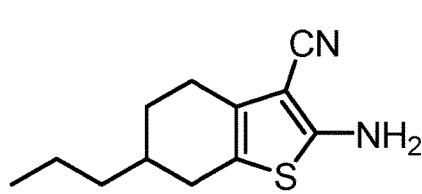
1 (I3-AG85)
MIC = 200 µg/mL
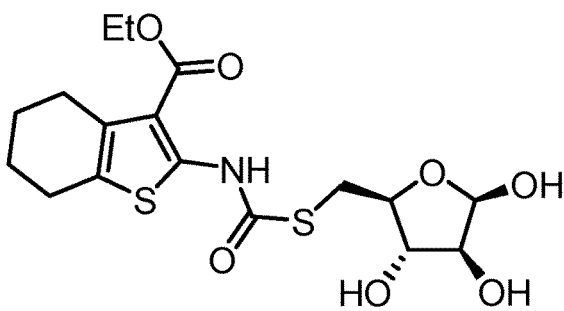
2
$K_i$ = 18.2 ± 1.8 µM
PKs13-inhibitors
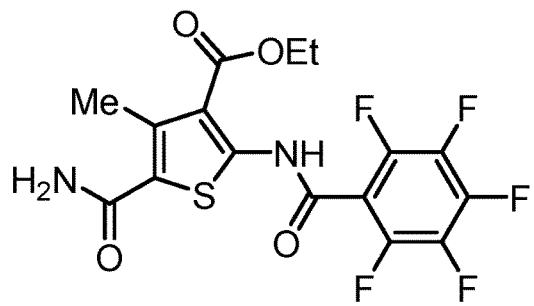
3
MIC = 0.5 µM
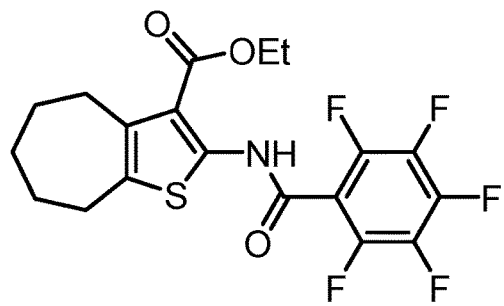
4
MIC = 1.0 µM
PRIOR ART FIG. 1

| | H37Rv (aerobic) | H37Rv (low oxygen) | H37Rv (intracellular) | INH-R1 | INH-R2 | RIF-R1 | RIF-R2 | FQ-R1 |
|---|---|---|---|---|---|---|---|---|
| | MIC = 0.23 | MIC > 200 | | MIC = 0.44 | MIC = 0.20 | MIC = 0.30 | MIC = 0.44 | MIC = 0.37 |
| | MIC$_{50}$ = 0.12 | IC$_{50}$ = 0.27 | IC$_{50}$ = 5.6 | IC$_{50}$ = 0.16 | IC$_{50}$ = 0.053 | IC$_{50}$ = 0.095 | IC$_{50}$ = 0.11 | IC$_{50}$ = 0.14 |
| | MIC$_{90}$ = 0.23 | IC$_{90}$ = 15 | IC$_{90}$ = 9.75 | IC$_{90}$ = 0.45 | IC$_{90}$ = 0.20 | IC$_{90}$ = 0.35 | IC$_{90}$ = 0.48 | IC$_{90}$ = 0.39 |
| Controls | | | | | | | | |
| RIF | MIC = 0.048, n=8 | | MIC = 0.012 | MIC = 0.0070 | MIC = 3.5 | MIC > 50 | MIC = 0.020 | |
| INH | | | IC$_{50}$ = 0.24 | MIC > 200 | MIC > 200 | MIC = 0.18 | MIC > 0.60 | MIC = 0.32 |
| Levofloxacin | | | | MIC = 1.3 | MIC = 1.4 | MIC = 1.2 | MIC = 1.2 | MIC = 24 |

FIG. 4A – Table 1

| Compound No. | MICs (μM) | Structure |
|---|---|---|
| 4{3,3,0} | Mtb H37Rv = 0.23 | 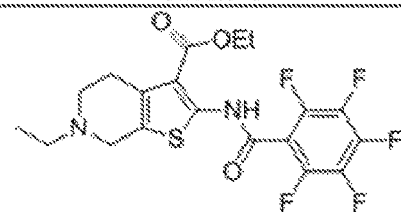 |
| 506 | Mtb H37Rv = 3.5 | 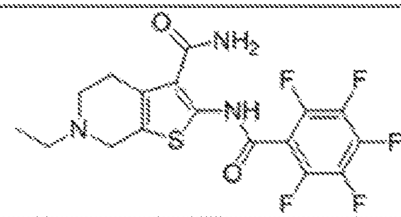 |
| 507 | Mtb H37Rv = 5.8 | 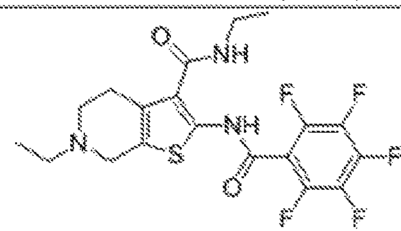 |
| 508 | Mtb H37Rv = 0.81 | 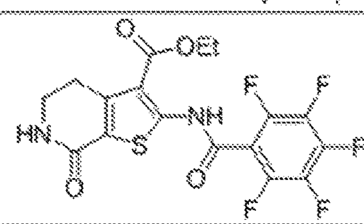 |
| 509 | Mtb H37Rv = 1.6 | 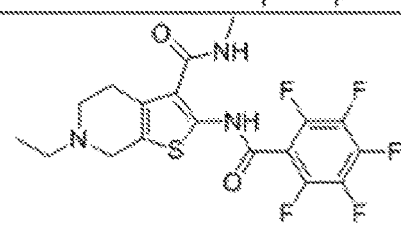 |
| 510 | Mtb H37Rv = 9.8 | 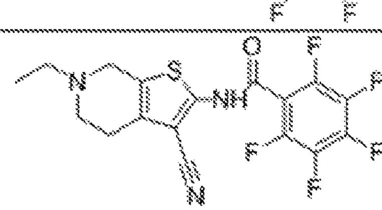 |

FIG. 4B – Table 2A

| Compound No. | MICs (μM) | Structure |
|---|---|---|
| 511 | Mtb H37Rv = 30 | 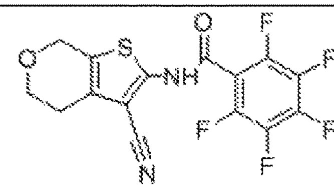 |
| 512 | Mtb H37Rv = 0.1 | 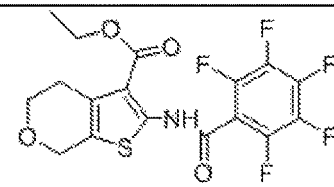 |
| 513 | Mtb H37Rv = 0.4 | 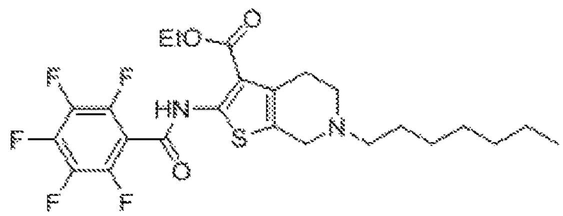 |
| 514 | Mtb H37Rv = 0.2<br>*Mycobacterium abscessus* = 1.7 | 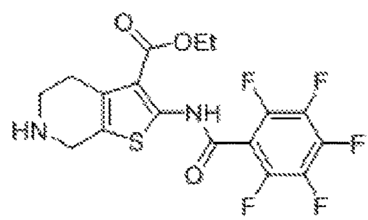 |
| 515 | Mtb H37Rv = 34 | 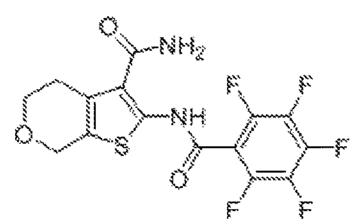 |

FIG. 4C – Table 2B

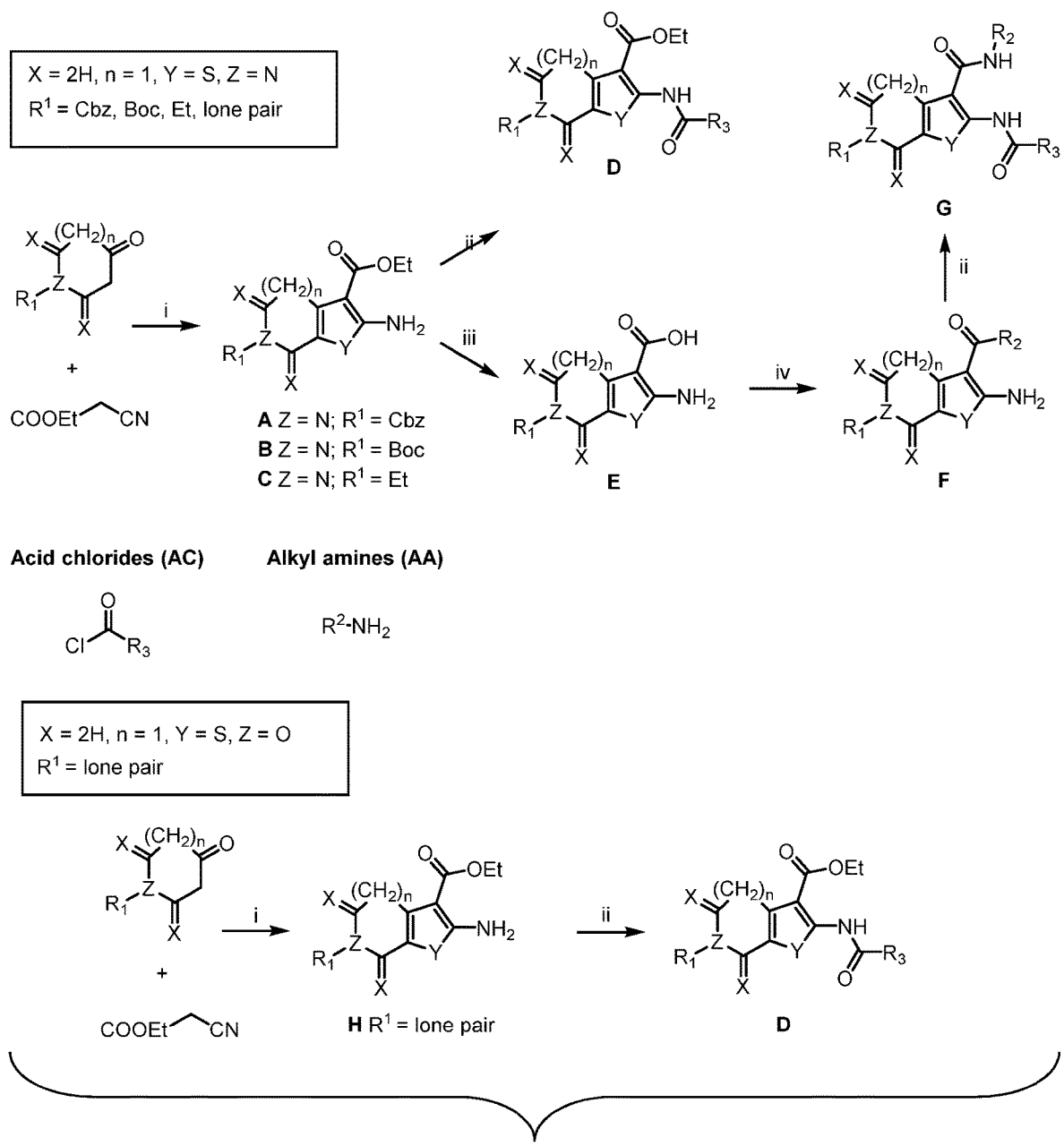
FIG. 5 - Scheme 1

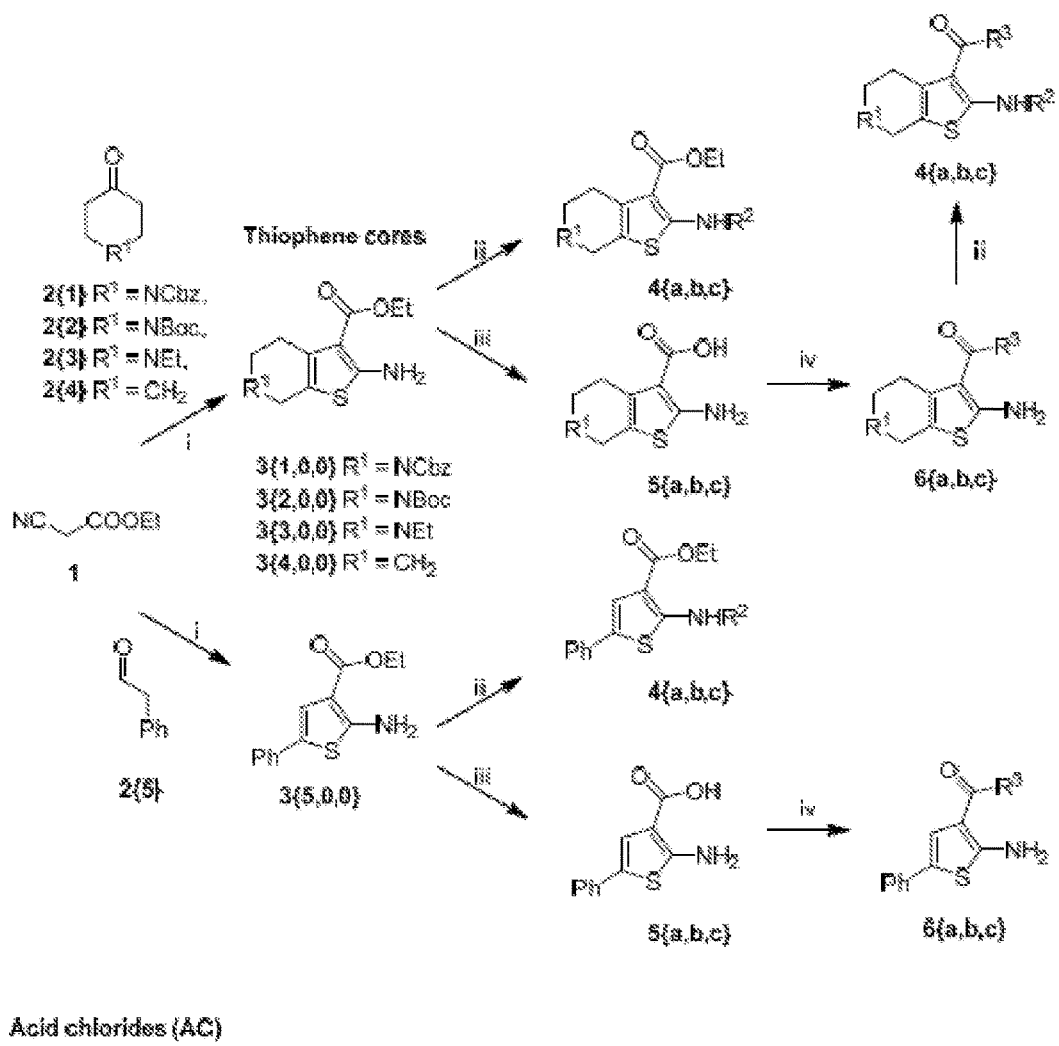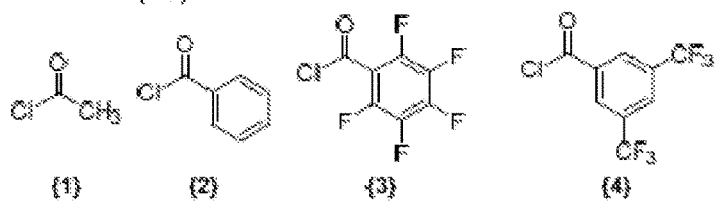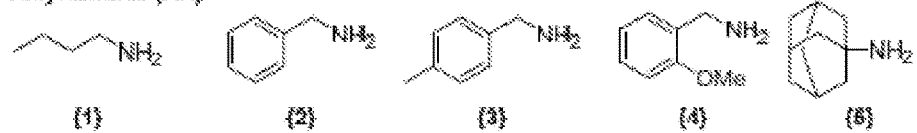
FIG. 6 - Scheme 2

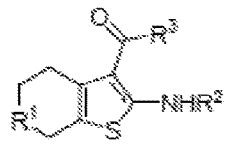

FRT

4{2,1,0}, 41%; R¹ = NBoc, R² = CH₃CO, R³ = OEt
4{2,2,0}, 23%; R¹ = NBoc, R² = C₆H₅CO, R³ = OEt
4{2,3,0}, 82%; R¹ = NBoc, R² = C₆F₅CO, R³ = OEt
4{2,4,0}, 39%; R¹ = NBoc, R² = 3,5-(CF₃)₂C₆H₃CO, R³ = OEt
4{3,1,0}, 45%; R¹ = NEt, R² = CH₃CO, R³ = OEt
4{3,2,0}, 35%; R¹ = NEt, R² = C₆H₅CO, R³ = OEt
4{3,3,0}, 45%; R¹ = NEt, R² = C₆F₅CO, R³ = OEt
4{3,4,0}, 43%; R¹ = NEt, R² = 3,5-(CF₃)₂C₆H₃CO, R³ = OEt
4{3,4,3}, 22%; R¹ = NEt, R² = 3,5-(CF₃)₂C₆H₃CO, R³ = 4-(CH₃)BnNH
4{4,1,0}, 59%; R¹ = CH₂, R² = CH₃CO, R³ = OEt
4{4,2,0}, 57%; R¹ = CH₂, R² = C₆H₅CO, R³ = OEt
4{4,3,0}, 50%; R¹ = CH₂, R² = C₆F₅CO, R³ = OEt
4{4,4,0}, 15%; R¹ = CH₂, R² = 3,5-(CF₃)₂C₆H₃CO, R³ = OEt
5{1,0,0}, 69%; R¹ = NCbz, R² = H, R³ = OH
5{2,0,0}, 89%; R¹ = NBoc, R² = H, R³ = OH
5{3,0,0}, 66%; R¹ = NEt, R² = H, R³ = OH
5{4,0,0}, 44%; R¹ = CH₂, R² = H, R³ = OH

6{3,0,1}, 36%; R¹ = NEt, R² = H, R³ = BuNH
6{3,0,2}, 25%; R¹ = NEt, R² = H, R³ = BnNH
6{3,0,3}, 40%; R¹ = NEt, R² = H, R³ = 4-(CH₃)BnNH
6{3,0,4}, 30%; R¹ = NEt, R² = H, R³ = 2-(OCH₃)BnNH
6{3,0,5}, 29%; R¹ = NEt, R² = H, R³ = AdamantylNH
6{4,0,1}, 26%; R¹ = CH₂, R² = H, R³ = BuNH
6{4,0,2}, 24%; R¹ = CH₂, R² = H, R³ = BnNH
6{4,0,3}, 36%; R¹ = CH₂, R² = H, R³ = 4-(CH₃)BnNH
6{4,0,4}, 23%; R¹ = NEt, R² = H, R³ = 2-(OCH₃)BnNH
6{4,0,5}, 21%; R¹ = NEt, R² = H, R³ = AdamantylNH

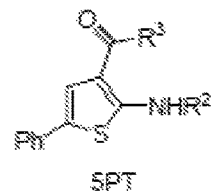

SPT

4{5,1,0}, 58%; R² = CH₃CO, R³ = OEt
4{5,2,0}, 94%; R² = C₆H₅CO, R³ = OEt
4{5,3,0}, 45%; R² = C₆F₅CO, R³ = OEt
4{5,4,0}, 45%; R² = 3,5-(CF₃)₂C₆H₃CO, R³ = OEt
5{5,0,0}, 83%; R² = H, R³ = OH
6{5,0,1}, 61%; R² = H, R³ = BuNH
6{5,0,2}, 59%; R² = H, R³ = BnNH
6{5,0,3}, 57%; R² = H, R³ = 4-(CH₃)BnNH
6{5,0,4}, 68%; R² = H, R³ = 4-(CH₃)BnNH
6{5,0,5}, 44%; R² = H, R³ = AdamantylNH

FIG. 7

MICs and IC$_{50}$s (μg/mL) of the 2AT Library *Mtb* H37Rv

| Comp No | NV/CLogP | MIC | IC$_{50}$ | Comp No | NV/CLogP | MIC | IC$_{50}$ |
|---|---|---|---|---|---|---|---|
| 3{1,0,0} | 0/2.80 | >100 | N/A | 4{5,4,0} | 1/6.39 | >100 | N/A |
| 3{2,0,0} | 0/2.39 | >100 | N/A | 5{1,0,0} | 0/2.16 | >100 | N/A |
| 3{3,0,0} | 0/1.73 | >100 | N/A | 5{2,0,0} | 0/1.75 | >100 | N/A |
| 3{4,0,0} | 0/2.52 | >200 | N/A | 5{3,0,0} | 0/1.09 | >100 | N/A |
| 3{5,0,0} | 0/3.26 | >100 | N/A | 5{4,0,0} | 0/1.88 | 100 | N/A |
| 4{2,1,0} | 0/2.12 | >100 | N/A | 5{5,0,0} | 0/2.62 | 50 | 28.29 |
| 4{2,2,0} | 0/3.79 | >100 | N/A | 6{3,0,1} | 0/2.15 | >100 | >100 |
| 4{2,3,0} | 1/4.33 | >100 | N/A | 6{3,0,2} | 0/2.11 | >100 | N/A |
| 4{2,4,0} | 2/5.51 | >100 | N/A | 6{3,0,3} | 0/2.56 | >100 | N/A |
| 4{3,1,0} | 0/1.46 | >100 | N/A | 6{3,0,4} | 0/2.12 | >100 | N/A |
| 4{3,2,0} | 0/3.50 | 100 | N/A | 6{3,0,5} | 0/3.48 | >100 | N/A |
| 4{3,3,0} | 0/4.03 | 0.31 | 0.29 | 6{4,0,1} | 0/2.94 | >100 | N/A |
| 4{3,4,0} | 1/5.22 | >100 | N/A | 6{4,0,2} | 0/2.90 | >100 | N/A |
| 4{3,4,3} | 2/5.89 | 200 | N/A | 6{4,0,3} | 0/3.35 | 100 | N/A |
| 4{4,1,0} | 0/2.25 | >100 | N/A | 6{4,0,4} | 0/2.91 | 100 | N/A |
| 4{4,2,0} | 0/3.95 | >200 | N/A | 6{4,0,5} | 0/4.27 | >100 | N/A |
| 4{4,3,0} | 0/4.45 | 12.5 | 12.5 | 6{5,0,1} | 0/3.68 | >100 | N/A |
| 4{4,4,0} | 1/5.64 | 1/5.64 | N/A | 6{5,0,2} | 0/3.64 | 100 | 107.78 |
| 4{5,1,0} | 0/3.00 | >100 | N/A | 6{5,0,3} | 0/4.09 | >100 | N/A |
| 4{5,2,0} | 0/4.67 | >100 | N/A | 6{5,0,4} | 0/3.65 | >100 | N/A |
| 4{5,3,0} | 1/5.20 | >100 | N/A | 6{5,0,5} | 1/5.01 | >100 | N/A |

FIG. 8 – Table 2

| Compound Preparation | |
|---|---|
| Both compounds were soluble in DMSO at 10 mM | |

| MIC | Task Summary | | | |
|---|---|---|---|---|
| Both compounds had activity against *M. tuberculosis* under aerobic conditions | Compound | MIC (µM) | IC$_{50}$ (µM) | IC$_{90}$ (µM) |
| | 4{3,3,0} | 0.23 | 0.12 | 0.23 |
| | selenylamide | 95 | 72 | 79 |

| MIC Under Low Oxygen | Task Summary | | | |
|---|---|---|---|---|
| Both compounds had activity against *M. tuberculosis* under low oxygen conditions | Compound | MIC (µM) | IC$_{50}$ (µM) | IC$_{90}$ (µM) |
| | 4{3,3,0} | > 200 | 0.27 | 15 |
| | selenylamide | > 200 | 21 | 64 |

| Minimum Bactericidal Concentration | Task Summary | |
|---|---|---|
| Both compounds were bactericidal | Compound | MBC (µM) |
| | 4{3,3,0} | <5 |
| | selenylamide | <5 |

| Intracellular Activity and Cytotoxicity | Task Summary | | |
|---|---|---|---|
| Both compounds were cytotoxic | | IC$_{50}$ (µM) | |
| | 4{3,3,0} | 6.2 | |
| | selenylamide | 39 | |
| Both compounds had activity against intracellular *M. tuberculosis* | Compound | IC$_{50}$ (µM) | IC$_{90}$ (µM) |
| | 4{3,3,0} | 5.8 | 9.7 |
| | selenylamide | 21 | > 50 |

| MIC Against Resistant Isolates | Task Summary | | |
|---|---|---|---|
| *M. tuberculosis* resistant isolates were resistant to 1 compound | Compound | MIC (µM) | Resistant Isolate |
| | selenylamide | 200 | RIF-R2 |

| MIC Against Other Disease Relevant Mycobacteria | Task Summary | | |
|---|---|---|---|
| 1 compound had activity against *M. abscessus*, 1 compound had activity against *M. avium* | Compound | MIC (µM) | Species |
| | 4{3,3,0} | 1.1 | *M. abscessus* |
| | selenylamide | 100 | *M. avium* |

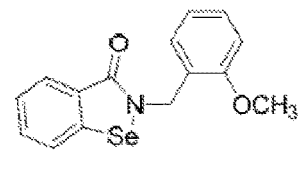

selenylamide

FIG. 10A

| Test Compounds | | | | | | |
|---|---|---|---|---|---|---|
| Compound ID | Assay Date | MIC (µM) | | | | |
| | | INH-R1 | INH-R2 | RIF-R1 | RIF-R2 | FQ-R1 |
| 4{3,3,0} | 20150729 | 0.44 | 0.20 | 0.30 | 0.44 | 0.37 |
| selenylamide | 20150729 | 74 | 84 | 63 | 200 | 86 |

| Test Compounds | | | | | | |
|---|---|---|---|---|---|---|
| Compound ID | Assay Date | $IC_{50}$ (µM) | | | | |
| | | INH-R1 | INH-R2 | RIF-R1 | RIF-R2 | FQ-R1 |
| 4{3,3,0} | 20150729 | 0.16 | 0.053 | 0.095 | 0.11 | 0.14 |
| selenylamide | 20150729 | 58 | 58 | 58 | 71 | 60 |

| Test Compounds | | | | | | |
|---|---|---|---|---|---|---|
| Compound ID | Assay Date | $IC_{90}$ (µM) | | | | |
| | | INH-R1 | INH-R2 | RIF-R1 | RIF-R2 | FQ-R1 |
| 4{3,3,0} | 20150729 | 0.45 | 0.20 | 0.35 | 0.48 | 0.39 |
| selenylamide | 20150729 | 67 | 66 | 65 | 98 | 67 |

FIG. 11

| Control Compounds | | | | | |
|---|---|---|---|---|---|
| | MIC (µM) | | | | |
| Compound ID | INH-R1 | INH-R2 | RIF-R1 | RIF-R2 | FQ-R1 |
| Rifampicin | 0.012 | 0.0070 | 3.5 | > 50 | 0.020 |
| Isoniazid | > 200 | > 200 | 0.18 | 0.60 | 0.32 |
| Levofloxacin | 1.3 | 1.4 | 1.2 | 1.2 | 24 |

| Control Compounds | | | | | |
|---|---|---|---|---|---|
| | $IC_{50}$ (µM) | | | | |
| Compound ID | INH-R1 | INH-R2 | RIF-R1 | RIF-R2 | FQ-R1 |
| Rifampicin | 0.0067 | 0.0047 | 1.9 | > 50 | 0.0094 |
| Isoniazid | > 200 | > 200 | 0.17 | 0.39 | 0.29 |
| Levofloxacin | 0.74 | 0.89 | 0.69 | 0.72 | 14 |

| Control Compounds | | | | | |
|---|---|---|---|---|---|
| | $IC_{90}$ (µM) | | | | |
| Compound ID | INH-R1 | INH-R2 | RIF-R1 | RIF-R2 | FQ-R1 |
| Rifampicin | 0.015 | 0.011 | 3.5 | > 50 | 0.031 |
| Isoniazid | > 200 | > 200 | 0.24 | 0.55 | 0.33 |
| Levofloxacin | 1.3 | 1.5 | 1.2 | 1.2 | 23 |

FIG. 12

Data Summary for *M. abscessus*

| Test Compounds | | | | | |
|---|---|---|---|---|---|
| Compound ID | Assay Date | Species | MIC (µM) | $IC_{50}$ (µM) | $IC_{90}$ (µM) |
| 4(3,3,0) | 20150731 | *M. abscessus* | 1.11 | 0.70 | 1.4 |
| selenylamide | 20150731 | *M. abscessus* | > 200 | > 200 | > 200 |

| Control Compounds | | | | | |
|---|---|---|---|---|---|
| Control Compound ID | Assay Date | Species | MIC (µM) | $IC_{50}$ (µM) | $IC_{90}$ (µM) |
| Rifampicin | 20150731 | *M. abscessus* | 6.1 | 3.9 | 5.7 |

Data Summary for *M. avium*

| Test Compounds | | | |
|---|---|---|---|
| Compound ID | Assay Date | Species | MIC (µM) |
| 4(3,3,0) | 20150731 | *M. avium* | > 200 |
| selenylamide | 20150731 | *M. avium* | 100 |

| Control Compounds | | | |
|---|---|---|---|
| Control Compound ID | Assay Date | Species | MIC (µM) |
| Rifampicin | 20150731 | *M. avium* | 0.10 |

FIG. 13A

| Compound Preparation | |
|---|---|
| All compounds were soluble in DMSO at 10 mM | |

| Plasma Protein Binding | |
|---|---|
| Compound | Protein Binding (%) |
| 4{3.3.0} | 99.9 |
| selenylamide | ND |

| Caco-2 Permeability | | | | |
|---|---|---|---|---|
| Compound | Assay Duration (h) | A→B $P_{app}$ ($10^{-6}$ cm/s) | B→A $P_{app}$ ($10^{-6}$ cm/s) | Efflux Ratio |
| 4{3.3.0} | 1 | 0.004 | 0.017 | 4.2 |
| selenylamide | 1 | 0 | 0 | NC |
| 4{3.3.0} | 2 | 0.07 | 0.67 | 9.6 |
| selenylamide | 2 | 0.1 | 0 | NC |

| Cytochrome P450 Inhibition | Task Summary | | |
|---|---|---|---|
| | Compound | CYP | IC50 (µM) |
| 2 compounds inhibited > 1 cytochrome P450 | 4{3.3.0} | CYP3A4 - Midazolam | 25.9 |
| | | CYP3A4 - Testosterone | 16.1 |
| | | CYP2C9 | 30.4 |
| | | CYP2D6 | 13.7 |
| | | CYP2C19 | 37.9 |
| | | CYP2B6 | 30.5 |
| | selenylamide | CYP3A4 - Midazolam | 3.7 |
| | | CYP3A4 - Testosterone | 2.5 |
| | | CYP2C9 | 10 |
| | | CYP2D6 | 6.4 |
| | | CYP2C19 | 8.9 |
| | | CYP2B6 | 6.93 |
| | | CYP2C8 | 1.3 |

| In vitro Microsomal Stability | Task Summary | | | | |
|---|---|---|---|---|---|
| Compound | Concentration (µM) | NADPH-Dependent $CL_{int}$ (µL/min/mg) | NADPH-Dependent $T_{1/2}$ (min) | NADPH-Free $CL_{int}$ (µL/min/mg) | NADPH-Free $T_{1/2}$ (min) |
| 4{3.3.0} | 1 | 57.4 | 40.2 | 27.7 | 83.8 |
| selenylamide | 1 | ND | ND | ND | ND |

FIG. 14

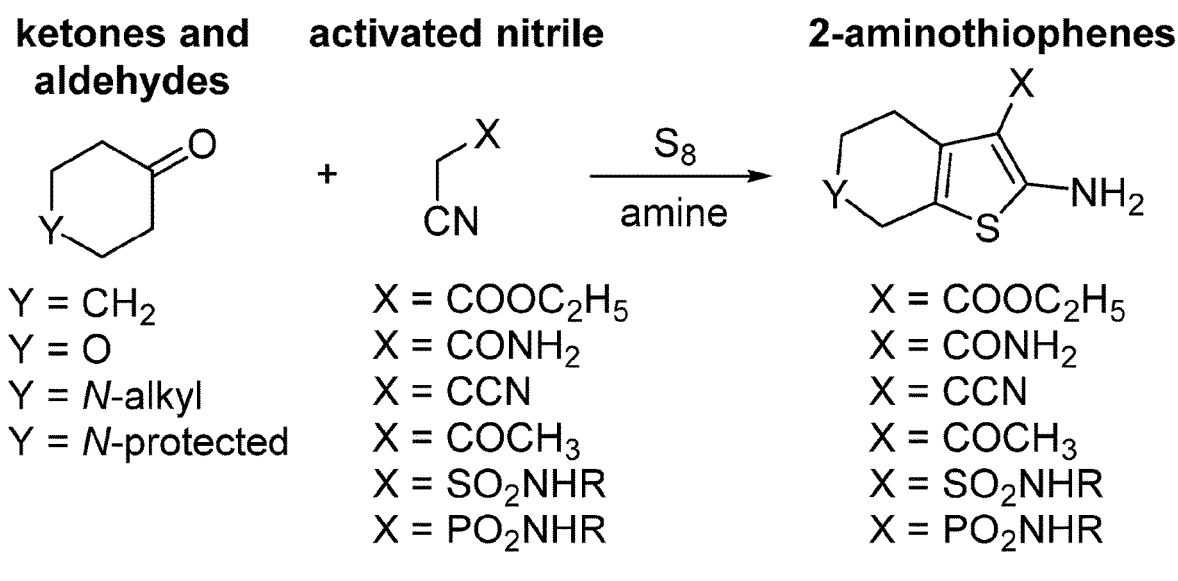
FIG. 17 – Scheme 3

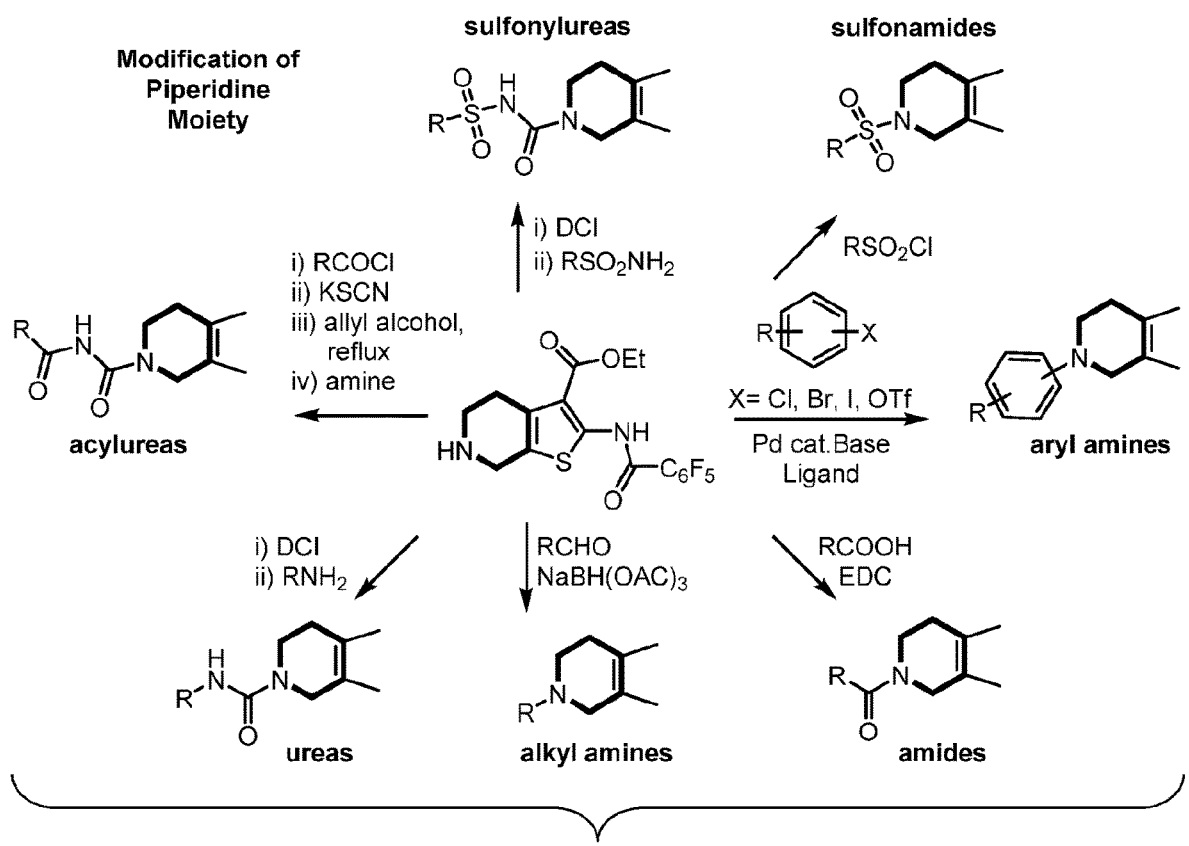
FIG. 18 – Scheme 4

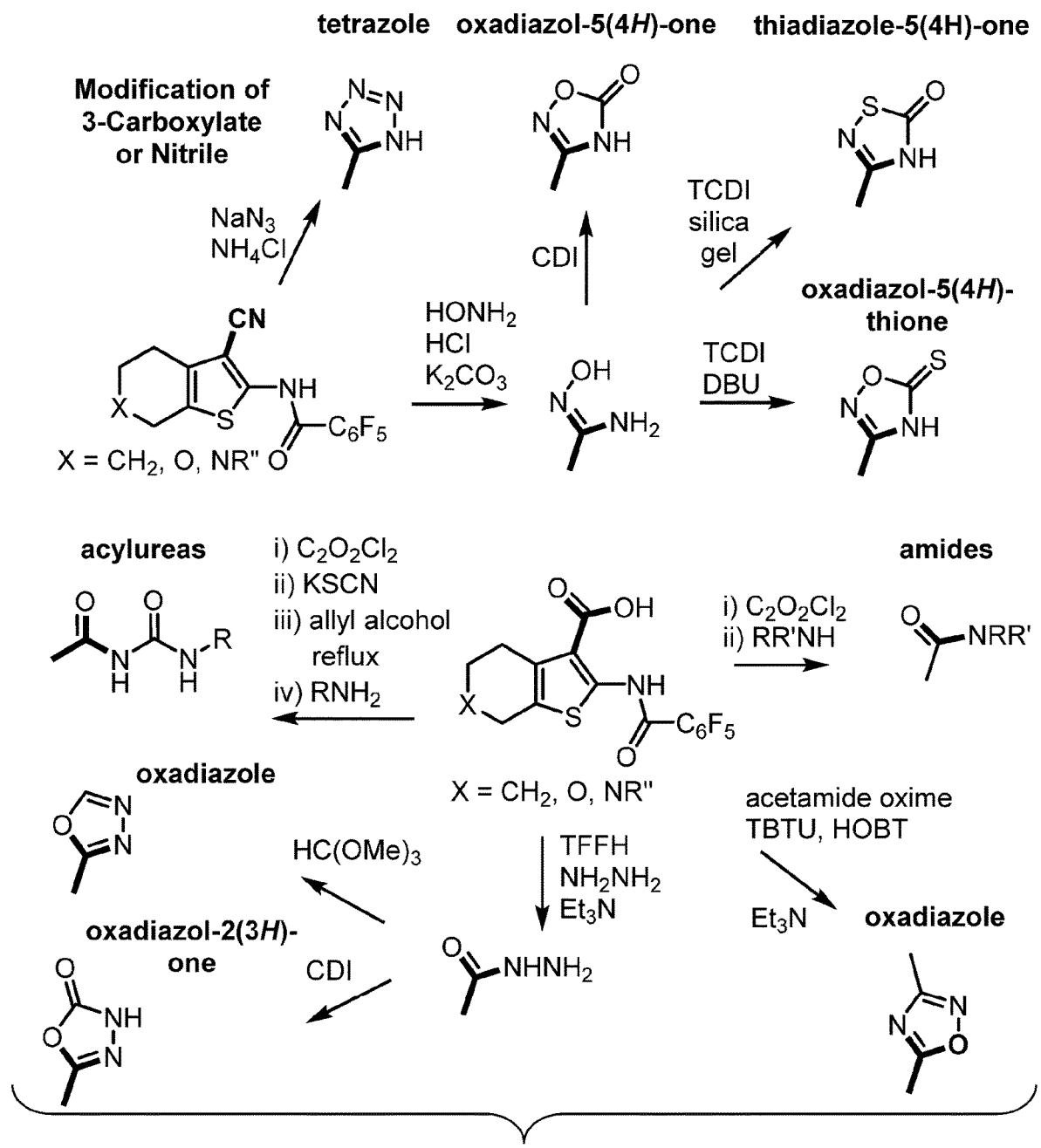
FIG. 19 – Scheme 5

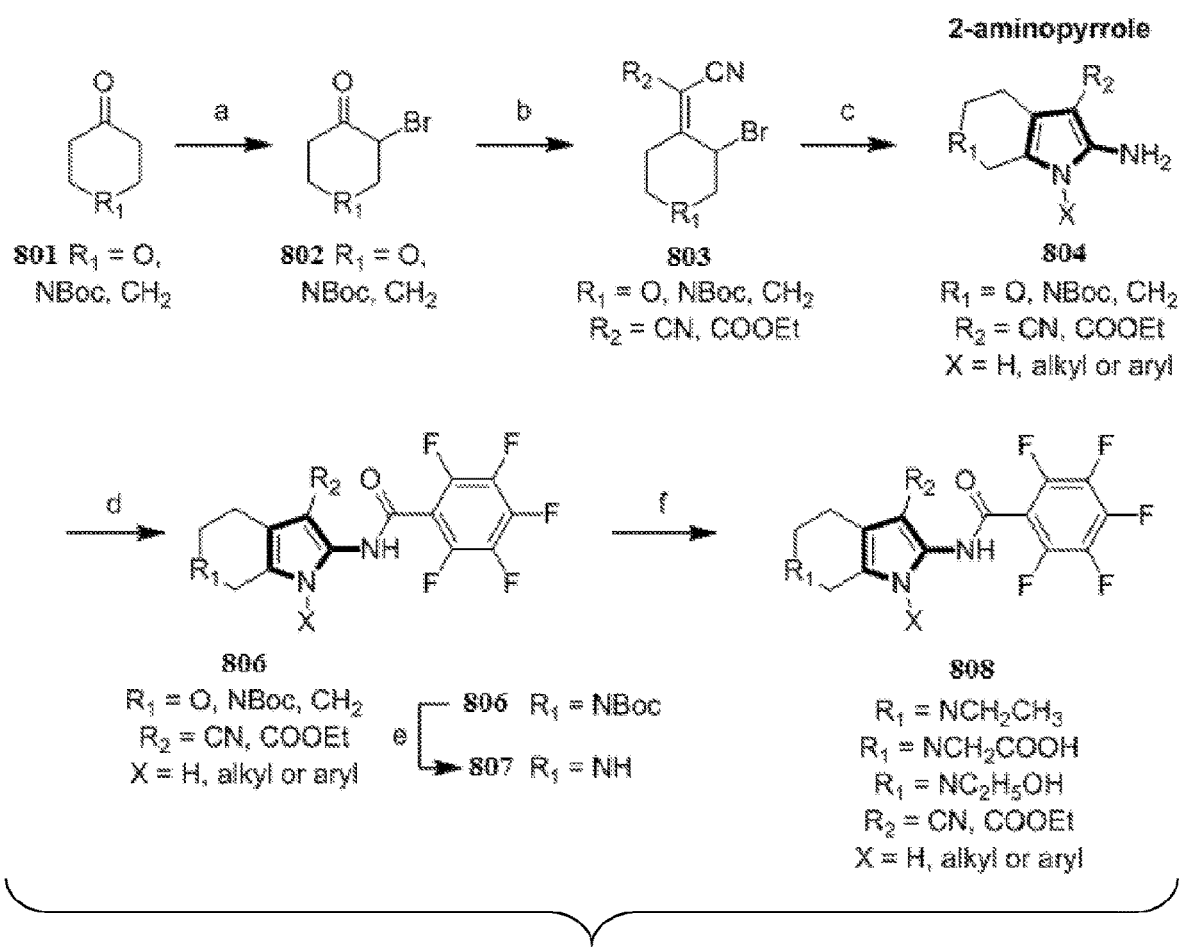
FIG. 20 – Scheme 6

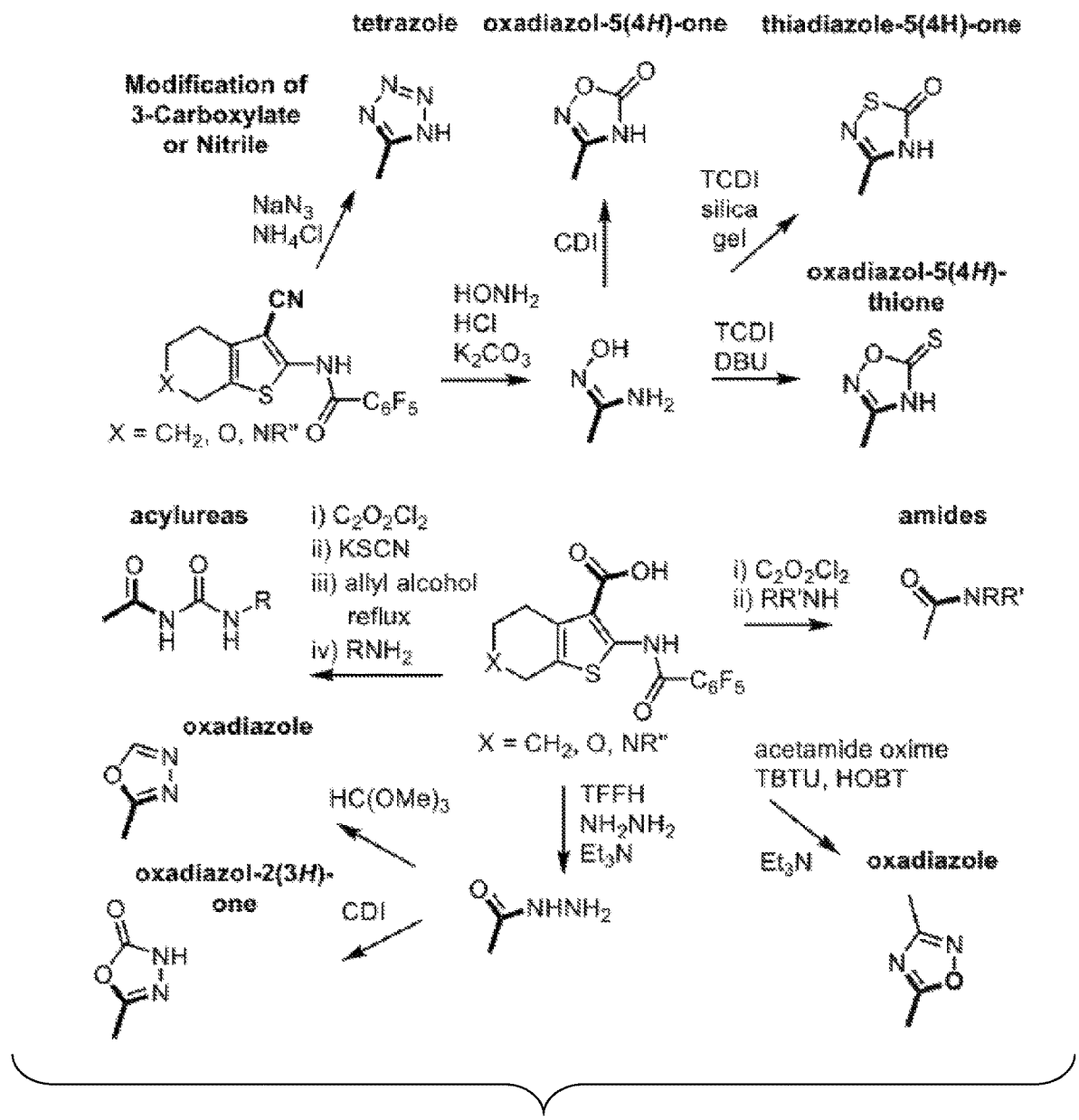
FIG. 21 – Scheme 7

| Compound Preparation | Task Summary | | |
|---|---|---|---|
| 1 compound was not soluble in DMSO at 10 mM | Compound | Solubility (mM) | Notes |
| | 509 | 5 | |

| MIC | Task Summary | | | |
|---|---|---|---|---|
| 4 compounds had activity against *M. tuberculosis* under aerobic conditions | Compound | MIC (µM) | IC$_{50}$ (µM) | IC$_{90}$ (µM) |
| | 506 | 6.0 | 2.4 | 6.9 |
| | 507 | 7.1 | 2.7 | 7.4 |
| | 508 | 0.75 | 0.27 | 0.75 |
| | 509 | 5.2 | 0.89 | 5.7 |

| MIC Under Low Oxygen | Task Summary | | | |
|---|---|---|---|---|
| 4 compounds had activity against *M. tuberculosis* under low oxygen conditions | Compound | MIC (µM) | IC$_{50}$ (µM) | IC$_{90}$ (µM) |
| | 506 | 50 | 5.0 | 43 |
| | 507 | 130 | 2.0 | 15 |
| | 508 | 13 | 1.3 | 3.8 |
| | 509 | 50 | 1.9 | 9.1 |

| Minimum Bactericidal Concentration | Task Summary | |
|---|---|---|
| 4 compounds had bactericidal activity | Compound | MBC (µM) |
| | 506 | 18 |
| | 507 | 29 |
| | 508 | 4.1 |
| | 509 | 8.0 |

| Intracellular Activity and Cytotoxicity | Task Summary | | |
|---|---|---|---|
| 4 compounds were cytotoxic | Compound | IC$_{50}$ (µM) | |
| | 506 | 8.6 | |
| | 507 | 22 | |
| | 508 | 44 | |
| | 509 | 10 | |
| 3 compounds had activity against intracellular *M. tuberculosis* | Compound | IC$_{50}$ (µM) | IC$_{90}$ (µM) |
| | 506 | 6.1 | 15 |
| | 507 | 2.7 | 5.2 |
| | 509 | 3.0 | 11 |

| MIC Against Resistant Isolates |
|---|
| *M. tuberculosis* resistant isolates were not resistant to any compounds |

| MIC Against Other Disease Relevant Mycobacteria |
|---|
| No compounds had activity against other Mycobacterial species |

FIG. 22

Test Compounds

| Compound | Assay Date | MIC (µM) | | | | |
|---|---|---|---|---|---|---|
| | | FQ-R1 | INH-R1 | INH-R2 | RIF-R1 | RIF-R2 |
| 506 | 20160527 | 11 | 11 | 12 | 12 | 8.6 |
| 507 | 20160527 | 9.8 | 10 | 11 | 8.5 | 9.2 |
| 508 | 20160527 | 3.2 | 4.4 | 1.4 | 1.5 | 2.0 |
| 509 | 20160527 | 3.8 | 1.7 | 3.2 | 4.0 | 3.0 |

Test Compounds

| Compound | Assay Date | $IC_{50}$ (µM) | | | | |
|---|---|---|---|---|---|---|
| | | FQ-R1 | INH-R1 | INH-R2 | RIF-R1 | RIF-R2 |
| 506 | 20160527 | 3.9 | 5.5 | 3.7 | 3.3 | 1.9 |
| 507 | 20160527 | 4.4 | 5.7 | 3.5 | 3.3 | 2.6 |
| 508 | 20160527 | 1.2 | 1.3 | 0.27 | 0.35 | 0.34 |
| 509 | 20160527 | 2.1 | 1.6 | 1.9 | 1.5 | 1.1 |

Test Compounds

| Compound | Assay Date | $IC_{90}$ (µM) | | | | |
|---|---|---|---|---|---|---|
| | | FQ-R1 | INH-R1 | INH-R2 | RIF-R1 | RIF-R2 |
| 506 | 20160527 | 11 | 12 | 14 | 15 | 11 |
| 507 | 20160527 | 11 | 11 | 13 | 9.3 | 9.4 |
| 508 | 20160527 | 3.4 | 4.7 | 1.4 | 1.6 | 1.9 |
| 509 | 20160527 | 3.8 | 2.4 | 3.0 | 4.4 | 3.3 |

Control Compounds

| Compound | Assay Date | MIC (µM) | | | | |
|---|---|---|---|---|---|---|
| | | FQ-R1 | INH-R1 | INH-R2 | RIF-R1 | RIF-R2 |
| Rifampicin | 20160527 | 0.018 | 0.011 | 0.013 | 6.1 | >50 |
| Isoniazid | 20160527 | 0.32 | >200 | >200 | 0.31 | 0.7 |
| Levofoxacin | 20160527 | 30 | 1.5 | 3.8 | 1.5 | 1.9 |

Control Compounds

| Compound | Assay Date | $IC_{50}$ (µM) | | | | |
|---|---|---|---|---|---|---|
| | | FQ-R1 | INH-R1 | INH-R2 | RIF-R1 | RIF-R2 |
| Rifampicin | 20160527 | 0.0087 | 0.0071 | 0.0056 | 0.86 | >50 |
| Isoniazid | 20160527 | 0.28 | >200 | >200 | 0.28 | 0.68 |
| Levofoxacin | 20160527 | 19 | 0.93 | 0.85 | 0.85 | 1.1 |

Control Compounds

| Compound | Assay Date | $IC_{90}$ (µM) | | | | |
|---|---|---|---|---|---|---|
| | | FQ-R1 | INH-R1 | INH-R2 | RIF-R1 | RIF-R2 |
| Rifampicin | 20160527 | 0.029 | 0.018 | 0.013 | 18 | >50 |
| Isoniazid | 20160527 | 0.33 | >200 | >200 | 0.32 | 0.83 |
| Levofoxacin | 20160527 | 34 | 1.5 | 4.8 | 1.6 | 1.9 |

FIG. 26

*M.abscessus*

Test Compounds

| Compound | Assay Date | Species | MIC (µM) | IC$_{50}$ (µM) | IC$_{90}$ (µM) |
|---|---|---|---|---|---|
| 506 | 20160531 | M. abscessus | > 200 | > 200 | > 200 |
| 507 | 20160531 | M. abscessus | > 200 | 120 | >200 |
| 508 | 20160531 | M. abscessus | > 200 | > 200 | > 200 |
| 509 | 20160531 | M. abscessus | >100 | >100 | >100 |

Control Compounds

| Control Compound ID | Assay Date | Species | MIC (µM) | IC$_{50}$ (µM) | IC$_{90}$ (µM) |
|---|---|---|---|---|---|
| Rifampicin | 20160531 | M. abscessus | 4.9 | 2.7 | 5.3 |

*M.avium*

Test Compounds

| Compound | Assay Date | Species | MIC (µM) |
|---|---|---|---|
| 506 | 20160527 | M. avium | > 200 |
| 507 | 20160527 | M. avium | > 200 |
| 508 | 20160527 | M. avium | > 200 |
| 509 | 20160527 | M. avium | > 100 |

Control Compounds

| Control Compound ID | Assay Date | Species | MIC (µM) |
|---|---|---|---|
| Rifampicin | 20160527 | M. avium | 0.098 |

FIG. 27

| Compound Preparation |
|---|
| All compounds were soluble in DMSO at 10 mM |

| MIC | Task Summary | | | |
|---|---|---|---|---|
| | Compound | MIC (µM) | IC$_{50}$ (µM) | IC$_{90}$ (µM) |
| All compounds had activity against *M. tuberculosis* under aerobic conditions | 510 | 9.8 | 5.7 | 11 |
| | 511 | 3.0 | 2.1 | 2.8 |
| | 512 | 0.10 | 0.10 | 0.18 |

| MIC Under Low Oxygen | Task Summary | | | |
|---|---|---|---|---|
| | Compound | MIC (µM) | IC$_{50}$ (µM) | IC$_{90}$ (µM) |
| All compounds had activity against *M. tuberculosis* under low oxygen conditions | 510 | 140 | 6.1 | 27 |
| | 511 | 180 | 2.2 | 18.0 |
| | 512 | 4.4 | 0.25 | 1.0 |

| Minimum Bactericidal Concentration | Task Summary | | | |
|---|---|---|---|---|
| | Compound | MBC (uM) | Compound | MBC (uM) |
| compounds were bactericidal | 510 | 22.5 | TSN-06-237 | 0.01675 |

| Intracellular Activity and Cytotoxicity | Task Summary | | |
|---|---|---|---|
| | Compound | IC$_{50}$ (µM) | |
| compounds were cytotoxic | 511 | 24 | |
| | 512 | 5.3 | |
| | Compound | IC$_{50}$ (µM) | IC$_{90}$ (µM) |
| All compounds had activity against intracellular *M. tuberculosis* | 510 | 5.2 | 9.9 |
| | 511 | 4.5 | 8.9 |
| | 512 | 1.9 | 4.5 |

| MIC Against Resistant Isolates |
|---|
| *M. tuberculosis* resistant isolates were not resistant to any compounds |

| MIC Against Other Disease Relevant Mycobacteria |
|---|
| No compounds had activity against other mycobacterial species |

FIG. 28

Test Compounds

| Compound | Assay Date | MIC (µM) | | | | |
|---|---|---|---|---|---|---|
| | | FQ-R1 | INH-R1 | INH-R2 | RIF-R1 | RIF-R2 |
| 510 | 20180721 | 18 | 20 | 20 | 18 | 13 |
| 511 | 20180721 | 13 | 16 | 12 | 10 | 3.4 |
| 512 | 20180721 | 0.33 | 0.37 | 0.26 | 0.25 | 0.23 |

Test Compounds

| Compound | Assay Date | $IC_{50}$ (µM) | | | | |
|---|---|---|---|---|---|---|
| | | FQ-R1 | INH-R1 | INH-R2 | RIF-R1 | RIF-R2 |
| 510 | 20180721 | 8.4 | 10 | 7.1 | 7.2 | 6.3 |
| 511 | 20180721 | 4.9 | 5.6 | 4.3 | 3.8 | 3.4 |
| 512 | 20180721 | 0.17 | 0.18 | 0.12 | 0.13 | 0.085 |

Test Compounds

| Compound | Assay Date | $IC_{90}$ (µM) | | | | |
|---|---|---|---|---|---|---|
| | | FQ-R1 | INH-R1 | INH-R2 | RIF-R1 | RIF-R2 |
| 510 | 20180721 | 20 | 21 | 22 | 21 | 13 |
| 511 | 20180721 | 15 | 18 | 13 | 12 | 5.4 |
| 512 | 20180721 | 0.35 | 0.40 | 0.28 | 0.27 | 0.24 |

Control Compounds

| Compound | Assay Date | MIC (µM) | | | | |
|---|---|---|---|---|---|---|
| | | FQ-R1 | INH-R1 | INH-R2 | RIF-R1 | RIF-R2 |
| Rifampicin | 20170821 | 0.024 | 0.022 | 0.010 | 3.8 | > 50 |
| Isoniazid | 20170821 | 1.2 | > 200 | > 200 | 0.39 | 1.2 |
| Levofloxacin | 20170821 | 46 | 1.6 | 1.3 | 1.5 | 2.0 |

Control Compounds

| Compound | Assay Date | $IC_{50}$ (µM) | | | | |
|---|---|---|---|---|---|---|
| | | FQ-R1 | INH-R1 | INH-R2 | RIF-R1 | RIF-R2 |
| Rifampicin | 20170821 | 0.012 | 0.011 | 0.005 | 2.1 | > 50 |
| Isoniazid | 20170821 | 0.84 | > 200 | > 200 | 0.29 | 0.85 |
| Levofloxacin | 20170821 | 28 | 1.3 | 1.2 | 1.2 | 1.3 |

Control Compounds

| Compound | Assay Date | $IC_{90}$ (µM) | | | | |
|---|---|---|---|---|---|---|
| | | FQ-R1 | INH-R1 | INH-R2 | RIF-R1 | RIF-R2 |
| Rifampicin | 20170821 | 0.035 | 0.018 | 0.010 | 4.0 | > 50 |
| Isoniazid | 20170821 | 1.3 | > 200 | > 200 | 0.50 | 1.1 |
| Levofloxacin | 20170821 | 49 | 2.0 | 1.4 | 1.7 | 2.2 |

FIG. 32

| Compound Formatting | Task Summary | |
| --- | --- | --- |
| 1 compound was not soluble in DMSO at 10 mM | Compound | Solubility (mM) |
| | 513 | 5 |

| Compound Solubility | Task Summary | |
| --- | --- | --- |
| Solubility of compounds was ≤ 200 µM in microbiological medium | Compound | Solubility (µM) |
| | 514 | 200 |
| | 515 | 50 |

| Compound Fluorescence |
| --- |
| No compounds were fluorescent |

| MIC under aerobic conditions | Task Summary | | | |
| --- | --- | --- | --- | --- |
| All compounds had activity against M. tuberculosis under aerobic conditions | Compound | MIC (µM) | $IC_{50}$ (µM) | $IC_{90}$ (µM) |
| | 513 | 0.40 | 0.21 | 0.40 |
| | 514 | 0.20 | 0.080 | 0.21 |
| | 515 | 34 | 7.8 | 38 |

| MIC Against Other Disease Relevant Mycobacteria | Task Summary | | |
| --- | --- | --- | --- |
| compounds had activity against other mycobacterial species | Compound | MIC (µM) | Species |
| | 514 | 1.7 | M. abscessus |
| | 515 | 95 | M. abscessus |
| | 514 | 200 | M. avium |

FIG. 33

*M. abscessus*

Test Compounds

| Compound | Assay Date | Species | MIC (µM) | IC$_{50}$ (µM) | IC$_{90}$ (µM) |
|---|---|---|---|---|---|
| 513 | 20170217 | M. abscessus | > 100 | 34 | > 100 |
| 514 | 20170217 | M. abscessus | 1.7 | 1.1 | 1.7 |
| 515 | 20170217 | M. abscessus | 95 | 68 | 86 |

Control Compounds

| Compound | Assay Date | Species | MIC (µM) | IC$_{50}$ (µM) | IC$_{90}$ (µM) |
|---|---|---|---|---|---|
| Rifampicin | 20170217 | M. abscessus | 5.4 | 2.8 | 5.5 |

*M. avium*

Test Compounds

| Compound | Assay Date | Species | MIC (µM) |
|---|---|---|---|
| 513 | 20170217 | M. avium | > 100 |
| 514 | 20170217 | M. avium | 200 |
| 515 | 20170217 | M. avium | > 200 |

Control Compounds

| Compound | Assay Date | Species | MIC (µM) |
|---|---|---|---|
| Rifampicin | 20170217 | M. avium | 0.078 |

ANTI-INFECTIVE 2-AMINOTHIOPHENES

RELATED APPLICATIONS

This application is a national stage application filed under 35 U.S.C. § 371 of international application PCT/US2017/028782, filed under the authority of the Patent Cooperation Treaty on Apr. 21, 2017, which claims priority to United States Provisional Application No. 62/325,755, filed under 35 U.S.C. § 111(b) on Apr. 21, 2016, the disclosure of which is incorporated herein by reference in its entirety for all purposes.

STATEMENT REGARDING FEDERALLY SPONSORED RESEARCH

This invention was made with government support under grant number AI105084 awarded by the National Institutes of Health. The government has certain rights in this invention.

BACKGROUND OF THE INVENTION

*Mycobacterium tuberculosis* (Mtb) is an acid-fast gram positive *bacillus* that causes tuberculosis (TB). TB, and its drug-resistant forms, kills more people than any other infectious disease. In 2013, there were 9.0 million active cases of TB. Of these, 0.48 case million were multidrug-resistant TB (MDR-TB). It is notable that the number of MDR-TB cases tripled from 2009 to 2013. This increase in MDR-TB and extensively drug-resistant TB (XDR-TB) has drawn worldwide attention. Furthermore, HIV-TB co-infection is a serious problem in countries where TB is endemic. HIV positive patients are 26-31 times more likely to develop active TB in comparison to an HIV negative person. Overall, 1.5 million people die every year from this disease.

It has been difficult to eradicate TB even though the infection is treatable. Treatment for TB takes at least 6 months and sometimes up to 2 years. The basic 6-month therapy involves two months of an intensive phase using the quadruple drug regimen consisting of Isoniazid (INH), Rifampicin (RIF), Ethambutol (EMB), and Pyrazinamide (PZA), followed by a 4-month continuous phase consisting of INH and RIF. Often, patients do not comply with the entire regimen due to the high numbers of pills/day and side-effects. The discontinuation of treatment allows resistance to develop. Therefore, there is an immediate need for drugs with improved efficacy and reduced toxicity.

SUMMARY OF THE INVENTION

Provided is a compound comprising Formula I:

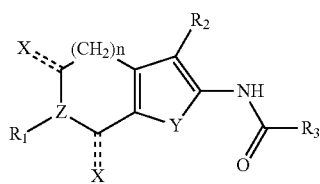

Formula I where dashed lines represent optional bonds; Z is O, N, or S; $R_1$ is a lone pair of electrons, H, $C_1$-$C_8$ alkyl, $C_1$-$C_8$ acyl, or $C_1$-$C_8$ aminoalkyl, or (a) $C_1$-$C_8$ alkyl optionally substituted with one or more of the following: F, Cl, hydroxy, $C_1$-$C_8$ alkyl, $C_1$-$C_8$ acyloxy, $C_1$-$C_8$ aminoalkyl, Ph or vinyl, $C_3$-$C_6$ cycloalkyl, or Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, C(O)$NR_4$, C(O)$OR_4$; (b) $C_1$-$C_8$ alkenyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph or vinyl, $C_3$-$C_6$ cycloalkyl, or Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, C(O)$NR_4$, or C(O)$OR_4$; (c) Ph optionally substituted with one or more of the following: F, Cl, hydroxy, $C_1$-$C_8$alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, C(O)$NR_4$, or C(O)$OR_4$; or (d) $C_3$-$C_6$ cycloalkyl; provided, however, that when Z is O or S, $R_1$ is a lone pair; $R_2$ is independently H, F, Cl, $C_1$-$C_8$ alkyl, $C_3$-$C_6$ cycloalkyl, $C_1$-$C_8$ alkoxy, $C_1$-$C_8$ acyloxy, $C_1$-$C_8$ aminoalkyl, amino, $C_1$-$C_8$ alkylamino, $C_1$-$C_8$ dialkylamino, O—$CH_2$-Ph, Ph, vinyl, CN, $CO_2H$, C(O)$OR_4$, or C(O)$NR_4$; $R_3$ is Ph optionally substituted with one to five of: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, C(O)$NR_4$, or C(O)$OR_4$; $R_4$ is independently Ph or $C_1$-$C_8$ alkyl, optionally substituted with one or more of: hydroxy, $C_1$-$C_8$ alkoxy, $C_1$-$C_8$ acyloxy, amino, $C_1$-$C_8$ alkylamino, $C_1$-$C_8$ dialkylamino, Ph, or vinyl; each X, when present, is independently O, NH, 2H, or S; Y is S, O, NH, $NR_4$, or $CH_2$; and n is 1 or 2. Also provided are salts, stereoisomes, racemates, hydrates, solvates, prodrugs, and polymorphs thereof.

In certain embodiments, $R_1$ is ethyl. In certain embodiments, each X is absent. In certain embodiments, $R_3$ is Ph substituted with five F. In certain embodiments, $R_1$ is ethyl, and each X is absent. In certain embodiments, $R_1$ is ethyl, and $R_3$ is Ph substituted with five F. In certain embodiments, each X is absent, and $R_3$ is Ph substituted with five F. In certain embodiments, $R_1$ is ethyl, each X is absent, and $R_3$ is Ph substituted with five F. In certain embodiments, n is 1. In certain embodiments, n is 1, each X is absent, and $R_3$ is Ph substituted with five F. In certain embodiments, $R_2$ comprises an ethyl ester. In certain embodiments, each X is absent, and $R_2$ comprises an ethyl ester. In certain embodiments, n is 1, and $R_2$ comprises an ethyl ester. In certain embodiments, n is 1, $R_2$ comprises an ethyl ester, and $R_3$ is Ph substituted with five F. In certain embodiments, Y is S. In certain embodiments, Y is S, n is 1, each X is absent, and $R_3$ is Ph substituted with five F.

In certain embodiments, the compound comprises Formula II:

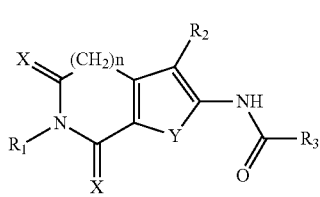

Formula II

In certain embodiments, the compound comprises Formula III:

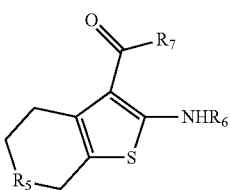
Formula III where $R_5$ is NEt, and $R_6$ is $COPhF_5$, and $R_7$ is $C_1$-$C_8$ alkyl, $C_1$-$C_8$ alkoxy, or $C_1$-$C_8$ carboxamide. In particular embodiments, $R_7$ is OEt. In particular embodiments, $R_7$ comprises benzamide.

In certain embodiments, the compound consists essentially of compound 4{3,3,0}:

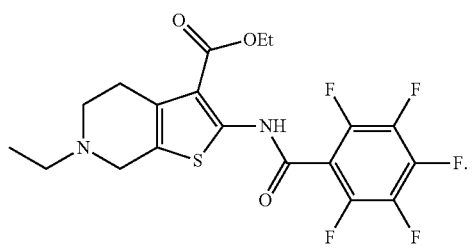
4{3,3,0}

In certain embodiments, Y is NH or $NR_4$. In particular embodiments, $R_4$ is alkyl or aryl.

In certain embodiments, the compound is compound 506:

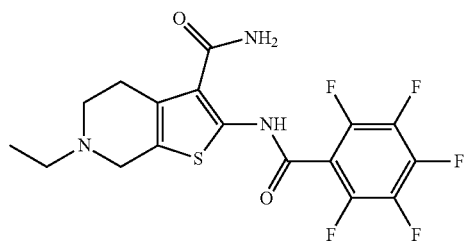
506

In certain embodiments, the compound is compound 507:

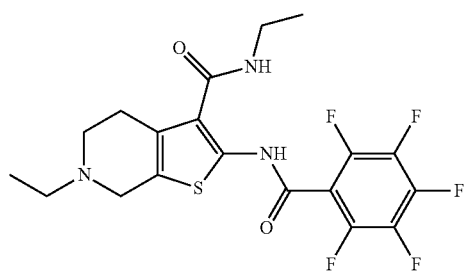
507

In certain embodiments, the compound is compound 508:

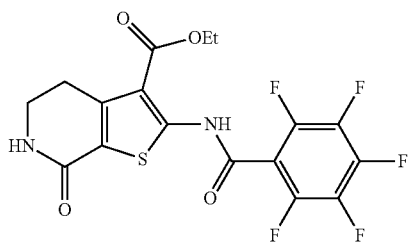
508

In certain embodiments, the compound is compound 509:

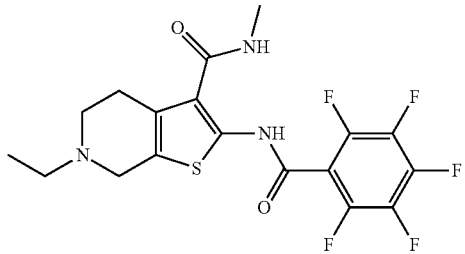
509

In certain embodiments, the compound is compound 510:

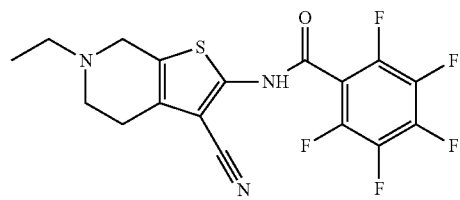
510

In certain embodiments, the compound is compound 511:

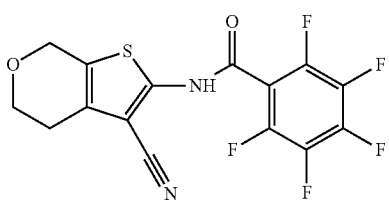
511

In certain embodiments, the compound is compound 512:

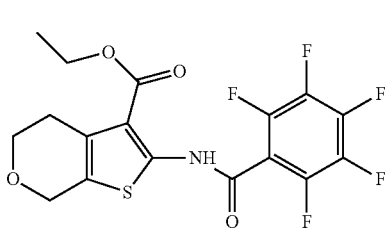
512

In certain embodiments, the compound is compound 513:

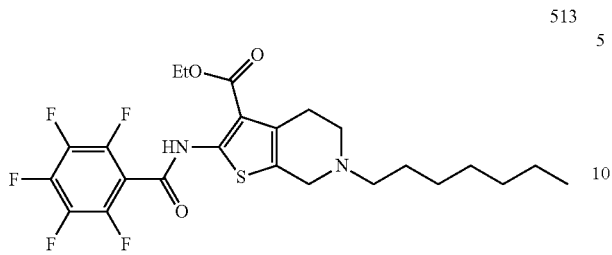

In certain embodiments, the compound is compound 514:

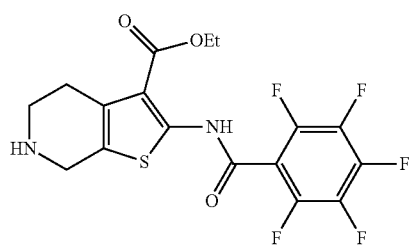

In certain embodiments, the compound is compound 515:

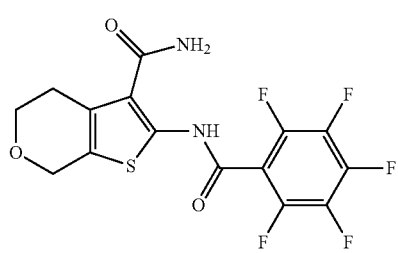

Also provided is a compound comprising Formula IV:

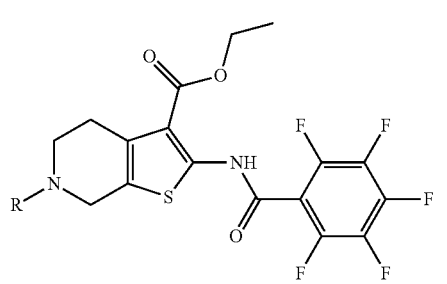

where R is a substituted or unsubstituted alkyl, sulfonyl, acyl, or aryl group, such that the compound contains a piperidine moiety modified with a urea, an acylurea, a sulfonylurea, an alkyl amine, an amide, an aryl amine, or a sulfonamide. Also provided are salts, stereoisomers, racemates, hydrates, solvates, prodrugs, and polymorphs of Formula IV.

Also provided is a compound comprising Formula V:

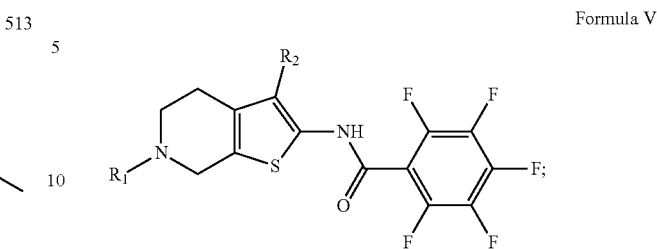

where $R_1$ is H, or substituted or unsubstituted $C_1$-$C_8$ acyl, $C_1$-$C_8$ alkyl, $C_1$-$C_8$ aminoalkyl, $C_1$-$C_8$ alkenyl, or Ph; and $R_2$ is a substituted or substituted tetrazole, oxadiazole, thiadiazole, thiadiazole ketone, oxadiazolethione, amide, acylurea, or oxadiazole ketone. Also provided are salts, stereoisomes, racemates, hydrates, solvates, prodrugs, and polymorphs of Formula V.

Also provided is a pharmaceutical composition comprising an effective amount of a compound of Formula I, and a pharmaceutically acceptable carrier, diluent, or excipient.

Also provided is a method of treating an infection, the method comprising administering an effective amount of a compound of Formula I to a subject having an infection, and treating the infection. In certain embodiments, the infection is an infection caused by a *Mycobacterium* species. In certain embodiments, the infection is an infection caused by *Mycobacterium tuberculosis*. In certain embodiments, the infection is an infection caused by a sensitive or drug-resistant strain of *Mycobacterium tuberculosis*. In certain embodiments, the infection is caused by *Mycobacterium abscessus* or *Mycobacterium avium*. In certain embodiments, the compound of Formula I is administered in a combination therapy with one or more antibacterial agents.

Also provided is a method of making a compound of Formula I, the method comprising reacting ethyl cyanoacetate with sulfur and a piperidinone to produce an aminothiophene carboxylate core, and reacting the aminothiophene carboxylate core with an acid chloride to produce a compound of Formula I.

Also provided is a kit for making a 2-aminothiophene derivative, the kit comprising a first container housing one or more of ethyl cyanoacetate, sulfur, and a piperidinone, and a second container housing an acid chloride.

Also provided is a method of determining coverage of health insurance reimbursement or payments, the method comprising denying coverage or reimbursement for a treatment, wherein the treatment comprises a compound of Formula I.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIG. 1: Structures of known Ag85C and Pks13 inhibitors with a 2-aminothiophene core.

FIGS. 4A-4C: Tables 1, 2A, and 2B. Table 1 (FIG. 4A) shows an evaluation of compound 4{3,3,0} MICs and ICs (μM) against Mtb under aerobic, low oxygen, and intracellular conditions, as well as an evaluation of compound 4{3,3,0} against isoniazid (INH)-, rifampicin (RIF)-, and fluoroquinolone (FQ)-resistant strains of Mtb. INH resistant INH-R1 was derived from H37Rv and is a katG mutant (Y155*=truncation). INH resistant INH-R2 is strain ATCC 35822. RIF resistant RIF-R1 was derived from H37Rv and is an rpoB mutant (S522L). RIF resistant RIF-R2 is strain ATCC 35828. FQ-R1 is a fluoroquinolone-resistant strain derived from H37Rv and is a gyrB mutant (D94N). Tables 2A (FIG. 4B) and 2B (FIG. 4C) show MICs against Mtb H37Rv under aerobic conditions and MICs against *Mycobacterium abscessus* (μM).

FIG. 5: Scheme 1, showing the synthesis scheme for 2-aminothiophene cores A-H. Reagents and conditions: (i) $S_8$, $Et_2N$, EtOH; (ii) Acid chloride, $Et_3N$, DCM, DMAP (15-82%); (iii) LiOH, THF: $H_2O$: MeOH (3:1:1) (44-89%); (iv) Alkyl amine, EDC. HCl, HOBt, DMAP, dry $CH_2Cl_2$ (21-61%).

FIG. 6: Scheme 2, showing the synthesis scheme for 2-aminothiophene cores 3{1,0,0} to 3{5,0,0}. Reagents and conditions: i) $S_8$, $Et_2N$, EtOH, 3{1,0,0} (86%), 3{2,0,0} (63%), 3{3,0,0} (75%), 3{4,0,0} (83%), 3{5,0,0} (61%); (ii) acid chloride (AC), $Et_3N$, DCM, DMAP (15-82%); (iii) LiOH, THF: $H_2O$:MeOH (3:1:1) (44-89%); (iv) alkylamine (AA), EDC. HCl, HOBt, DMAP, dry $CH_2Cl_2$ (21-61%). In a compound numbered {a,b,c}, a=thiophene core, b=acid chloride, c=alkylamine.

FIG. 7: 2-Aminothiophenes prepared as described in the Examples herein. The yield is shown following the compound number.

FIG. 8: Table 2, showing MICs and $IC_{50}$s (μg/mL) of the 2AT library Mtb H37Rv. NV=Number of violations for Lipinski rule of five. CLogP=Calculated Log P value.

FIGS. 10A-10G: Data showing comparison of a selenylamide and compound 4{3,3,0} in activity against *M. tuberculosis* under aerobic conditions and low oxygen conditions, minimum bactericidal concentrations, intracellular activity and cytotoxicity, activity against *M. tuberculosis* resistant isolates, and activity against other Mycobacteria, as well as P450 enzyme inhibition and HepG2 toxicity data for compound 4{3,3,0} and the selenylamide. FIG. 10A is a summary of the data. FIG. 10B shows the dose-response curves of compound 4{3,3,0} under low and normal oxygen. FIGS. 10C-10F show inhibition of six cytochrome P450 enzyme isoforms—CYP2B6, $CYP2C_8$, $CYP2C_9$, $CYP2C_{19}$, CYP2D6, and CYP3A4—by compound 4{3,3,0} and the selenylamide. FIG. 10G shows the results of an in vitro microsomal stability assay for compound 4{3,3,0}.

FIG. 11: Summary showing a comparison of compound 4{3,3,0} and a selenylamide against drug resistant Mtb.

FIG. 12: Summary of the controls against drug resistant Mtb.

FIGS. 13A-13C: Evaluation of MIC of compound 4{3,3,0} and a selenylamide against other disease-relevant Mycobacteria. FIG. 13A shows a summary of the data against *M. abscessus* and *M. avium*. FIG. 13B shows the dose-response curves for compound 4{3,3,0} against *M. abscessus*. FIG. 13C shows the plate image and plate layout of the MIC evaluation for compound 4{3,3,0} and selenylamide against *M. avium*.

FIG. 14: Summary of certain pharmacokinetic data for compound 4{3,3,0} and a selenylamide.

FIG. 17: Scheme 3, depicting the general synthesis of certain 2-aminothiophenes.

FIG. 18: Scheme 4, depicting example modifications of the piperidine ring within a 2-aminothiophene.

FIG. 19: Scheme 5, depicting example isosteres of the 3-carboxylate accessed through hthe 3-nitrile or 3-carboxylate (bold) within a 2-aminothiophene.

FIG. 20: Scheme 6, depicting the synthesis of 2-aminopyrrole (bold) libraries. Reagents: a) Br, $CHCl_3$, 41%; b) malononitrile or ethyl cyanoacetate, β-alanine, $H_2O$, reflux; c) primary amine, piperidine, DMF; d) DMAP, DCM; e) TFA, DCM; f) aldehyde, $NaBH(OAc)_3$, DCE.

FIG. 21: Scheme 7, depicting isosteres of the 3-carboxylate accessed through the 3-nitrile or 3-carboxylate (bold) within a 2-aminothiophene.

FIG. 22: Summary of data for compounds 506-509 showing activity against *M. tuberculosis* under aerobic conditions and low oxygen conditions, minimum bactericidal concentrations, intracellular activity and cytotoxicity, activity against *M. tuberculosis* resistant isolates, and activity against other Mycobacteria.

FIG. 26: Summary of activity of compounds 506-509 against five resistant isolates of *M. tuberculosis* strains assessed under aerobic conditions by determining the minimum inhibitory concentration (MIC) of compound.

FIG. 27: Summary of the MICs for compounds 506-509 against *M. abscessus* and *M. avium*.

FIG. 28: Summary of MIC data for compounds 510-512.

FIG. 32: Summary of MICs for compounds 510-512 against resistant isolates.

FIG. 33: Summary of MIC data for compounds 513-515.

FIG. 35: Summary of MICs for compounds 513-515 against *M. abscessus* and *M. avium*.

FIG. 37: Summary of evaluation of compounds 506-509 for plasma protein binding, Caco-2 permeability, cytochrome P450 inhibition, in vitro microsomal stability, and HepG2 cytotoxicity.

DETAILED DESCRIPTION

Figure 2:
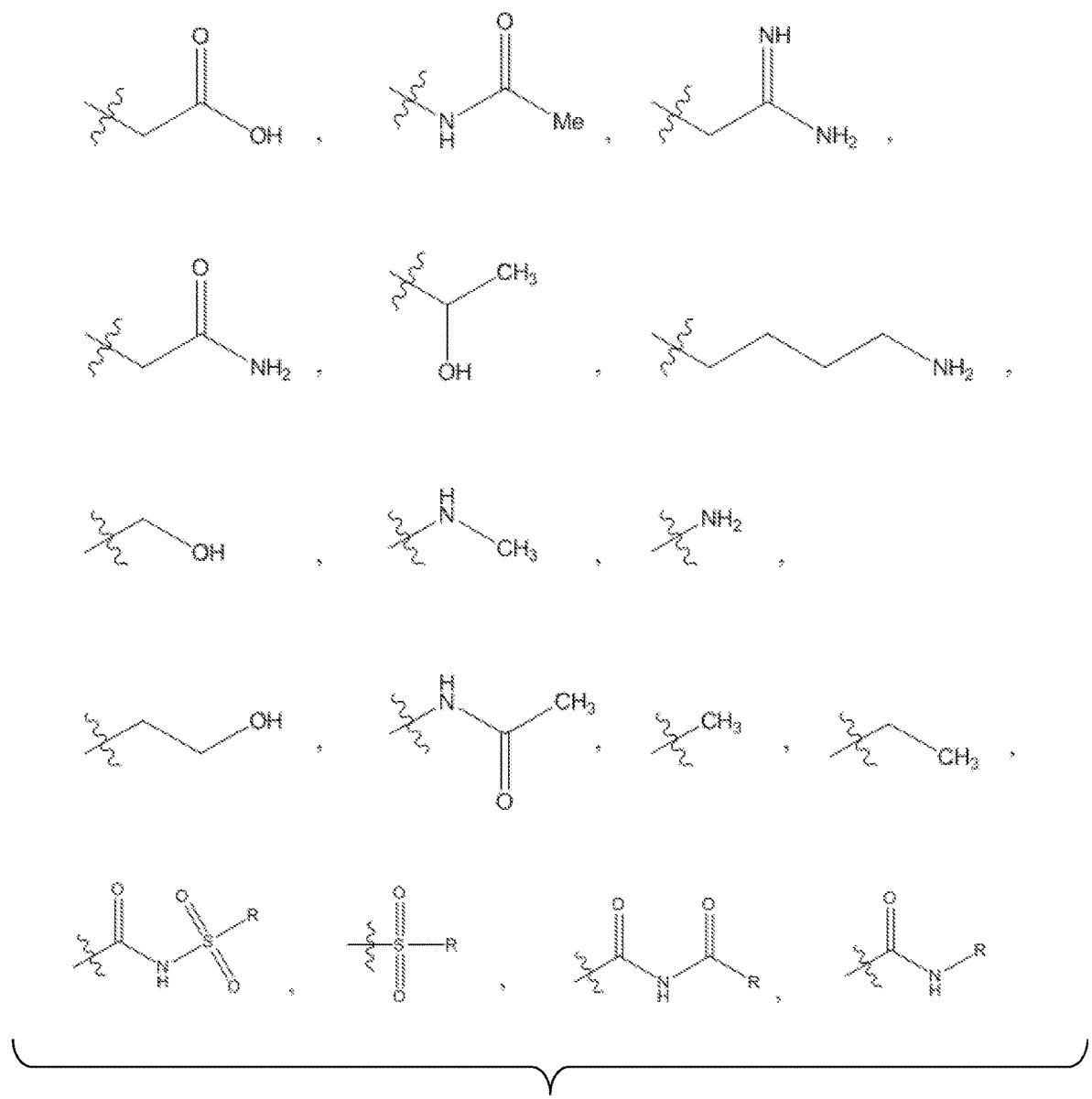
FIG. 2: Non-limiting examples of suitable structures for $R_1$ of Formula I.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, various terms are defined prior to further description of the present disclosure.

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

It will also be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

The term "prodrug" refers to a precursor or derivative of a particular compound which, when consumed, generates the pharmacologically active compound by action of natural processes or biological conditions. For example, a prodrug can be cleaved, hydrolyzed, or oxidized by enzymes in vivo to produce the pharmacologically active compound.

The carbon content of various hydrocarbon-containing moieties is indicated by a prefix designating the minimum and maximum number of carbon atoms in the moiety, i.e., the prefix $C_i$-$C_j$ defines the number of carbon atoms present from the integer 'i' to the integer "j" inclusive. Thus, $C_1$-$C_3$ alkyl refers to alkyl of 1-3 carbon atoms, inclusive, or methyl, ethyl, propyl, and isopropyl; $C_1$-$C_8$ alkyl is methyl, ethyl, propyl, butyl, pentyl, hexyl, heptyl, octyl, and isomeric forms thereof.

The term "alkyl" means a functional group or substituent derived from an alkane missing one hydrogen. "Alkyl" can be a straight or branched alkyl such as, but not limited to, methyl, ethyl, propyl, tert-butyl, or sec-butyl. The number of carbons in alkyl may be specified. For example, "$C_1$-$C_6$ alkyl" means an alkyl as described above containing from 1 to 6 carbon atoms.

The term "haloalkyl" means an alkyl as described above wherein one or more hydrogens are replaced by halo. The term "halo" means fluoro, chloro, bromo, or iodo.

The term "aryl" refers to a functional group containing, or derived from, an aromatic ring. Aryl groups include, but are not limited to, phenyl, naphthyl, thienyl, indolyl, or any of the preceding functional groups substituted by $C_1$-$C_6$ alkyl, one or more halogens, trifluoromethyl, or lower alkyl or lower alkoxy moieties.

The term "acyl" refers to a functional group derived from an oxoacid having one or more hydroxyl groups removed. An acyl group contains a double bonded oxygen atom and an alkyl group. The number of carbons in acyl may be specified. For example, "$C_n$-acyl" refers to a radical having a single carbon atom of a carbonyl group as the point of attachment, further having a linear or branched, cyclic or acyclic structure, further having a total of n carbons, 1 or more hydrogen atoms, and a total of one oxygen atom.

The term "aryloxy" means an aryl group singular bonded to oxygen. A non-limiting example of an aryloxy group is phenoxy, $C_6H_5O$—.

The term "alkoxy" means an alkyl group singular bonded to oxygen.

The term "aralkyl" refers to a radical derived from an alkyl radical by replacing one or more hydrogen atoms with one or more aryl groups. In other words, an aralkyl group is an aryl-substituted alkyl group.

The term "Ph" refers to phenyl. The term "Bn" refers to benzyl.

The term $C_1$-$C_8$ alkylamino means an amino moiety (—NH—) containing one alkyl moiety having 1 to 8 carbon atoms. The term $C_1$-$C_8$ dialkylamino means an amino moiety containing two alkyl moieties having 1 to 8 carbon atoms, for example, propylamino and dipropylamino, respectively. The $C_1$-$C_8$alkyl or $C_1$-$C_4$ alkyl groups can be optionally substituted with fluoro, chloro, azido, hydroxy, $C_1$-$C_8$ alkyl, $C_1$-$C_8$ alkoxy, amino, $C_1$-$C_8$ alkylamino, $C_1$-$C_8$ dialkylamino, or —O—$CH_2Ph$, where "Ph" is phenyl. The term $C_1$-$C_8$ aminoalkyl means an alkyl radical containing one amino moiety having 1 to 8 carbon atoms. The term "vinyl" refers to —CH=$CH_2$. "Acyloxy" refers to groups such as methylcarbamate, ethylcarbamate, etc. Optionally substituted $C_1$-$C_8$ alkyl groups can include 1-chloropropyl, 1-fluoropropyl, 3-chloropropyl, 3-fluoropropyl, 1-hydroxybutyl, 2-hydroxybutyl, 1-methoxypropyl, 1-octyloxypropyl, 1-aminopropyl, 1-aminooctyl, 1-butylaminopropyl, 1-dibutylaminopropyl, and the like.

The term "pharmaceutically acceptable salts," as used herein, refers to salts of compounds of the present disclosure that are substantially non-toxic to living organisms. Typical pharmaceutically acceptable salts include those salts prepared by reaction of a compound of the present disclosure with an inorganic or organic acid, or an organic base, depending on the substituents present on the compounds. Pharmaceutically acceptable salts includes acid addition salts useful for administering the compounds of the present disclosure. Non-limiting examples of pharmaceutically acceptable salts are hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, and the like when a basic group is present. These salts may be in hydrated form. The benzene ring, in addition to being unsubstituted, can be substituted with one or more halogen atoms in the series fluorine or chlorine. Thus, the $R_1$ through $R_4$ groups can be independently either hydrogen atoms or halogen atoms in a variety of substitution patterns.

Examples of inorganic acids which may be used to prepare pharmaceutically acceptable salts include: hydrochloric acid, phosphoric acid, sulfuric acid, hydrobromic acid, hydroiodic acid, phosphorous acid, and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the compounds of the present disclosure with an organic base such as methylamine, ethylamine, ethanolamine, lysine, ornithine, and the like. Other suitable salts are known to one of ordinary skill in the art.

It should be recognized that the particular anion or cation forming a part of any salt is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference for all purposes.

General Description

The present disclosure describes 2-aminothiophene derivatives that are useful antibacterial agents, effective against acid-fast bacteria such as, but not limited to, *Mycobacterium* species such as *Mycobacterium tuberculosis, Mycobacterium abscessus*, and *Mycobaterium avium*. The compounds have the following general Formula I:

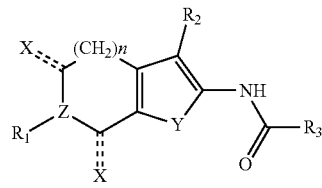

Figure 3A:
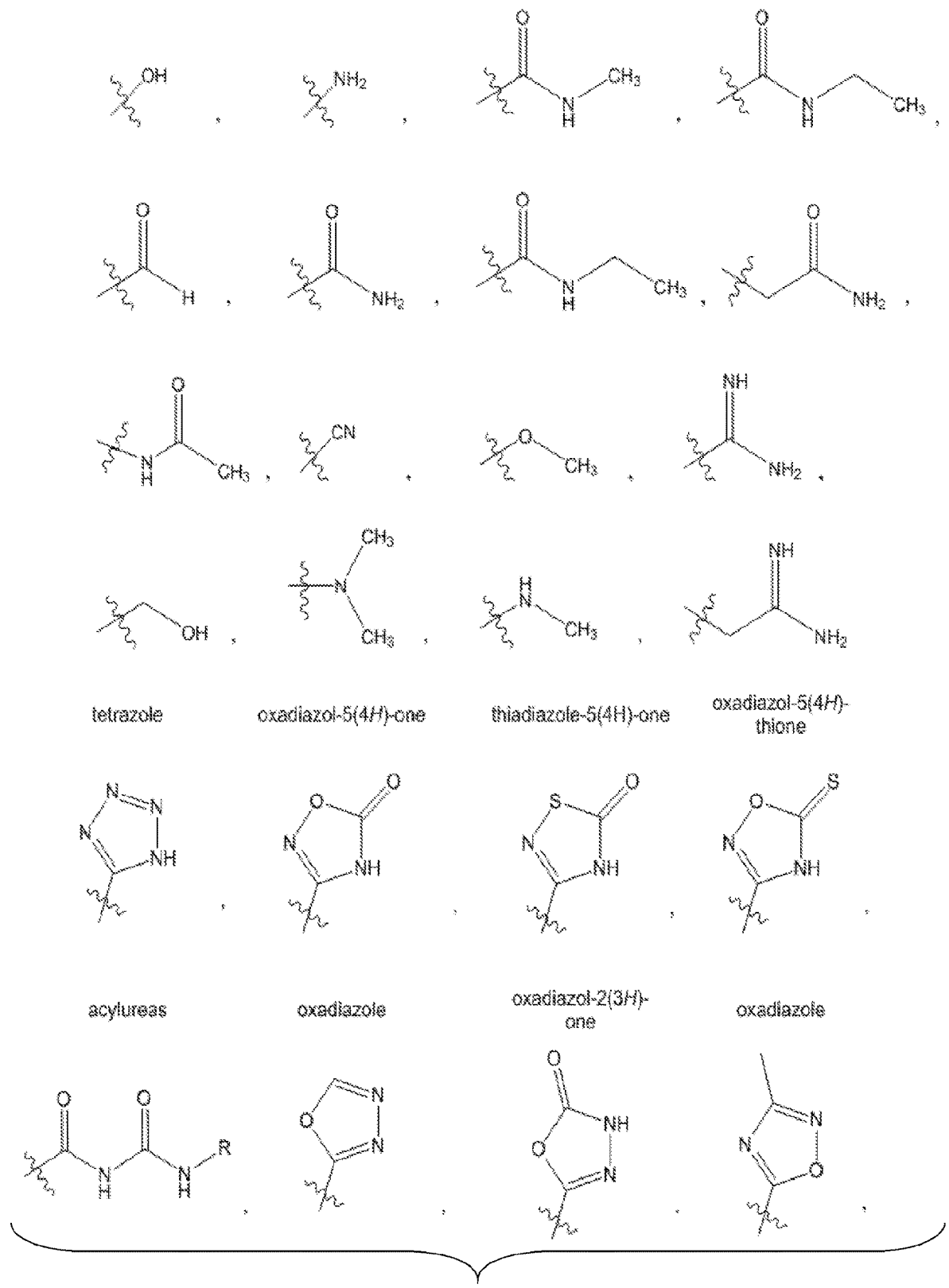
FIGS. 3A-3B: Non-limiting examples of suitable structures for $R_2$ of Formula I.
Figure 3B:
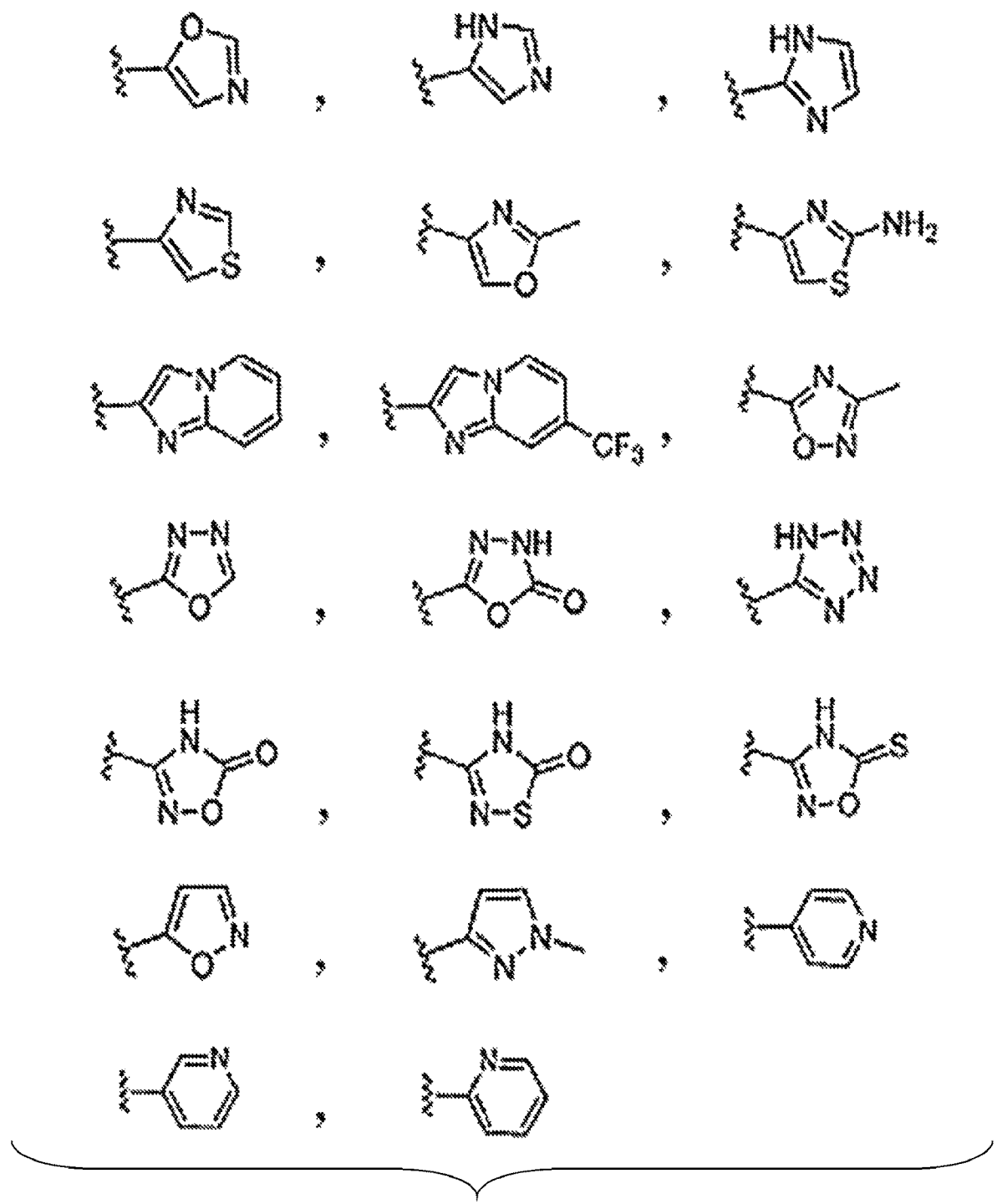

Formula I where dashed lines represent optional bonds; Z is O, N, or S; $R_1$ is a lone pair, one the groups shown in FIG. 2, or (a) $C_1$-$C_8$ alkyl optionally substituted with one or more of the following: F, Cl, hydroxy, $C_1$-$C_8$ alkyl, $C_1$-$C_8$ acyloxy, $C_1$-$C_8$ aminoalkyl, Ph or vinyl, $C_3$-$C_6$ cycloalkyl, or Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $C(O)NR_4$, or $C(O)OR_4$; (b) $C_1$-$C_8$ alkenyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph or vinyl, $C_3$-$C_6$ cycloalkyl, or Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $C(O)NR_4$, or $C(O)OR_4$; (c) Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $C(O)NR_4$, or $C(O)OR_4$; or (d) $C_3$-$C_6$ cycloalkyl; $R_1$ is independently H, $C_1$-$C_8$ alkyl, $C_1$-$C_8$ acyl, or $C_1$-$C_8$ aminoalkyl; provided, however, that when Z is O or S, $R_1$ is a lone pair; $R_2$ is independently H, F, Cl, $C_1$-$C_8$ alkyl, $C_3$-$C_6$ cycloalkyl, $C_1$-$C_8$ alkoxy, $C_1$-$C_8$ acyloxy, $C_1$-$C_8$ aminoalkyl, amino, $C_1$-$C_8$ alkylamino, $C_1$-$C_8$ dialkylamino, O—$CH_2$-Ph, Ph, vinyl, CN, $CO_2H$, $C(O)OR_4$, $C(O)NR_4$; $R_3$ is one of the groups shown in FIGS. 3A-3B, or Ph optionally substituted with one to five of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $C(O)NR_4$, or $C(O)OR_4$; $R_4$ is independently Ph, $C_1$-$C_8$ alkyl (optionally substituted with one or more of the following: hydroxy, $C_1$-$C_8$ alkoxy, $C_1$-$C_8$ acyloxy, amino, $C_1$-$C_8$ alkylamino, $C_1$-$C_8$ dialkylamino, Ph, or vinyl; each X, when present, is independently O, NH, 2H, or S; Y is S, O, NH, $NR_4$, or $CH_2$; and n is 1 or 2. In certain embodiments, $R_1$ is one the groups shown in FIG. 2. Without wishing to be bound by theory, it is believed that the identity of $R_1$ modifies the PK activity of the compounds. In certain embodiments, $R_2$ is one of the groups shown in FIGS. 3A-3B. Even though the compounds herein are often described as 2-aminothiophenes for convenience, it is understood that Y of Formula I need not be S, and therefore, many non-thiophenes are encompassed within Formula I.

In one non-limiting example, the compound of Formula I has the following structural formula:

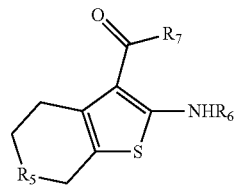

Formula III where $R_5$ is NEt, $R_6$ is $COPhF_5$, and $R_7$ is OEt. This example compound is referred to as compound 4{3,3,0}. Thus, compound 4{3,3,0} has the following structural formula:

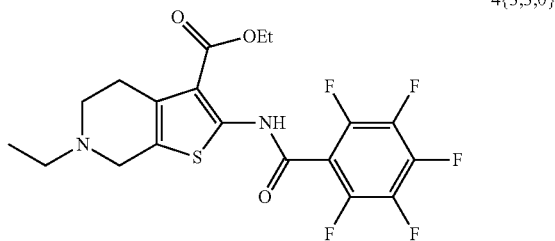

4{3,3,0}

Compound 4{3,3,0} is also known as ethyl 6-ethyl-2-(perfluorobenzamido)-4,5,6,7-tetrahydrothieno[2,3-c]pyridine-3-carboxylate.

Another non-limiting example of a compound of Formula I is a compound similar to compound 4{3,3,0} except that the $R_2$ ethoxy is replaced with a methyl benzamide (4{3,4,3}). Compound 4{3,4,3} is also known as 2-(3,5-bis(trifluoromethyl)benzamido)-6-ethyl-N-(4-methylbenzyl)-4,5,6,7-tetrahydrothieno[2,3-c]pyridine-3-carboxamide.

Additional non-limiting examples of compounds of Formula I are compounds 506-515, depicted in FIGS. 4B-4C (Tables 2A-2B).

The compounds herein can be made in a variety of manners, such as through the synthetic schemes depicted in FIGS. 5-6. Scheme 1 (FIG. 5) shows the synthesis of certain examples from Scheme 2 (FIG. 6). For instance, core D from Scheme 1 (FIG. 5) is an example of core 4(a,b,c) from Scheme 2 (FIG. 6).

As seen from FIGS. 5-6, the compounds herein can be prepared beginning from ethyl cyanoacetate, which can be reacted with sulfur and a piperidinone to produce a 2-aminothiophene-3-carboxylate core (compounds A-C in FIG. 5). The 2-aminothiophene-3-carboxylate can be reacted with an acid chloride, such as a fluoro-substituted benzoyl chloride, in the presence of a suitable base, such as triethylamine, to produce a 2-aminothiophene derivative of Formula I. In one non-limiting example, the acid chloride is 2,3,4,5,6-pentafluorobenzoyl chloride, and the resulting 2-aminothiophene derivative of Formula I is compound 4{3,3,0}. Advantageously, the compounds of Formula I have a low cost of preparation.

The compounds herein can also be made through the synthetic schemes depicted in FIGS. 17-20. The 2-AT systems can be accessed from the Gewald three-component reaction (Scheme 3, FIG. 17). In some embodiments, the nitrogen is replaced with oxygen. As seen from Scheme 3, 2-amino-3-sulfonamide and 2-amino-3-phosphonamide thiophene derivatives can be accessed. Cyanomethanesulfonamides are commercially available and therefore available for use in the Gewald reaction. The corresponding cyanomethanephosphonamide starting materials are accessible using bromomethanesulfonamides followed by substitution with NaCN. Scheme 3 depicts further modification to the R groups in these 2-AT scaffolds. For example, a piperidine moiety can be introduced. The nitrogen of the piperidine can be used as a handle to improve the drug proproperies of 2-ATs. Scheme 4 (FIG. 18) represents other 2-AT libraries. Amides, alkyl or aryl amines, ureas, acylureas, sulfonylureas, and sulfonamides can be accessed according to Scheme 4 (FIG. 18). In some embodiments (e.g., acylureas and sulfonylureas), these functional groups provide the ability to impart improved drug permeability properties.

The ethyl ester of compound 801 (Scheme 6, FIG. 20) may be hydrolyzed by esterases so that compound stability may be improved by employing transformations shown in Scheme 5 (FIG. 19). The Gewald reaction yields 3-nitriles or 3-carboxylates, depending on the choice of starting materials (that is, using malononitrile or ethyl cyanoacetate, respectively). These nitriles can be converted to tetrazoles, oxadiazol-5(4H)-ones, thiadiazol-5(4H)-ones, and ozadiazol-5(4H)-thiones, according to the upper section of Scheme 5 (FIG. 19). The lower section of Scheme 5 shows how 3-carboxylates can be converted to amides, oxadiazoles, oxadiaxol-2(3H)-ones, and even acylureas. The skilled person will recognize that there are a number of additional carboxylate isosteres that can be accessed. The isosteres of the 3-carboxylate on the 2-aminothiophene structure accessible via Scheme 7, depicted in FIG. 21, are encompassed by the present disclosure. These isosteres are accessible through the 3-nitrile or 3-carboxylate (shown in bold in FIG. 21).

Further compounds can be accessed by modifying the 2-AT to an 2-aminopyrrole as shown in Scheme 6 (FIG. 20), which may improve metabolic stability. The 2-aminopyrrole motif was selected based on in silico ADME modeling studies using StarDrop (Optibrium, Ltd). Modules within StarDrop predict log P, log D7.4, solubility, human intestinal absorption, CNS Penetration, cytochrome P450 affinities, P-gp transport, hERG pIC50, and plasma protein binding. The ring system can be accessed by bromination of ketones 801 with molecular bromine to access the α-haloketones. Cyclohexanone, N-Boc protected 4-piperidinone, or tetrahydropyran-4-one can be used as starting ketones. α-Haloketones can be subjected to a Knoevenagel condensation with malononitrile or ethyl cyanoacetate to afford compounds 803. These vinyl nitriles can be cyclized in the presence of primary amines to obtain 2-aminopyrroles 804 Amines such as tritylamine can afford N-protected derivatives. Compounds 804 can be acylated with pentafluorobenzoyl chloride to obtain compounds 806. These resulting compounds can be modified according to, for example, Scheme 5 (FIG. 19), depending on the available functional group. In the case where compound 806 is an N-Boc derivative, the Boc group can be deprotected to afford 807 and modified according to Scheme 4 (FIG. 18). Scheme 6 (FIG. 20) shows compound 807 subjected to reductive amination with various aldehyde groups to form compounds 808.

The compounds described herein are useful anti-microbial agents, particularly against Mtb. Mtb has an unusual cell wall that contains a thick hydrophobic layer. This differs from typical Gram positive (G+) and Gram negative (G−) bacteria, making it resistant to many drugs that normally act on G+ and G− bacteria. The main constituents of the Mtb cell wall include a plasma membrane, peptidoglycan layer, hydrophobic layer, and an outer capsule. The hydrophobic layer is made up of mycolylarabinogalactan (mAG), trehalose monomycolate (TMM), trehalose dimycolate (TDM, Cord Factor), phenolic glycolipids, and many other lipids, and is critical for bacterial virulence. The arabinogalactan and trehalose are found in the cell wall as esters of mycolic acids (MAs). MAs are α-alkyl-β-hydroxy fatty acids with total carbon chain lengths ranging from $C_{60}$ to $C_{90}$, with an α-side chain with carbon lengths ranging from $C_{24}$ to $C_{26}$. They esterify both the cell wall arabinogalactan and extractable glycolipids of the cell envelope, particularly, trehalose monomycolate (TMM), and trehalose dimycolate (TDM, Cord Factor).

Biosynthesis of MAs is achieved by at least two fatty acid synthases (FASs): FAS-I and FAS-II. FAS-I is considered "eukaryotic-like" and produces two acyl-CoA fatty acids. One fatty acid has a carbon chain length of $C_{24}$-$C_{26}$, which is carboxylated by ACCase/AccD4 to form a carboxyacyl-CoA derivative which becomes the α-branch of MAs. The second fatty acid has a chain length of $C_{16}$-$C_{18}$ and is elongated by FAS-II. FAS-II is considered a "bacterial-like" fatty acid synthase which participates in the production of the meromycolic chain ($C_{42}$-$C_{62}$). The product of FAS-II is a $C_{42}$-$C_{62}$ carboxylic acid which is converted to meromycoloyl-AMP by FadD32. Pks13 is a polyketide synthase that catalyzes a Claisen-type condensation between the meromycoloyl-AMP and carboxyacyl-CoA to produce a mycolic β-ketoester. This product is transferred to trehalose and the β-ketoester is reduced by Cmr to form TMM. Pks13 is important for Mtb and is an anti-tuberculosis drug target.

Some 2-aminothiophenes are found in a variety of natural and synthetic products, and include compounds with anti-tuberculosis activity. Some 2-aminothiophenes are reported to inhibit either Pks13 or Ag85s. The compound I3-AG85 (1) has been reported to be an inhibitor of Ag85s (PRIOR ART FIG. 1). Ethyl 2-amino-4,5,6,7-tetrahydrobenzo[b]thiophene-3-carboxylate derivative (2) was designed and synthesized as an Ag85C inhibitor with moderate activity. Other compounds that act as Pks13 inhibitors have been identified, including the finding that compounds 3 and 4 had low MICs against Mtb H37Rv (PRIOR ART FIG. 1). In contrast to the compounds shown in PRIOR ART FIG. 1, the compounds of the present disclosure show MIC values lower than compounds 3 and 4, and have been shown to have activity against both sensitive and drug resistant strains of *Mycobacterium tuberculosis*, as well as against *Mycobacterium abscessus* and *Mycobacterium avium* in some embodiments.

The compounds of Formula I are useful antimicrobial agents, effective against human and veterinary pathogens, particularly acid-fast organisms such as *Mycobacterium tuberculosis*. Antimicrobial activity of the compounds herein was demonstrated by determining the minimum inhibitory concentration for *Mycobacterium tuberculosis* H37Rv strain. The compound 4{3,3,0} showed good MIC values, as displayed in Table 1 (FIG. 4A). FIGS. 4B-4C show Tables 2A and 2B, displaying MIC values for compounds 506-515 (in addition to compound 4{3,3,0}) against Mtb H37Rv under aerobic conditions and, for certain compounds, against *Mycobacterium abscessus* (μM).

Further, the compounds of Formula I have a good activity to toxicity ratio. In some embodiments, the compounds of Formula I are active at concentrations 20-fold lower than toxicity, are active under low oxygen conditions, and are active against the most important drug-resistant strains of Mtb, as well as mycobacteria other than Mtb. It is understood that the compounds of Formula I may be effective against many different types of organisms other than *Mycobacteria* species, and the treatment of infections by such organisms with the compounds of Formula I is encompassed within the present disclosure.

Pharmaceutical compositions of the present disclosure comprise an effective amount of a compound of Formula I (an "active" ingredient), and/or additional agents, dissolved or dispersed in a pharmaceutically acceptable carrier. The pharmaceutically acceptable composition of compounds of Formula I may be prepared by combining the solid or liquid of pharmaceutically acceptable carrier and optionally with pharmaceutically acceptable adjuvants and excipients by using standard and conventional techniques. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered orally, intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 2003, incorporated herein by reference).

For oral administration, the compound of Formula I and its salts can be formulated as solids as well as liquids. Solid medications include pills, tablets, dispersible granules, capsules, powder, cachets, and suppositories. A solid carrier which can be at least one substance of which may also function as flavoring agent, solubilizer, lubricant, suspending agent, binder, tablet disintegrating agent and encapsulating agent, which including lactose, sucrose, cornstarch, gelatin, magnesium carbonate, magnesium stearate, sugar, pectin, dextrin, cellulosic materials, low melting wax, cocoa butter, and the like. For liquid medicaments, the composition may include aqueous solutions such as syrups, flavored syrups, aqueous or suspensions, emulsions with edible oils, and elixirs. In one non-limiting example, a compound is suspended or dispersed in synthetic agents such as tragacanth, acacia, dextran, sodium carboxymethylcellouse, methylcellouse, and gelatin.

For intravenous-administered medicaments, the compound is formulated with suitable liquid injection vehicle, which includes water, saline, dextrose, water-miscible solvents such as ethanol, polyethylene glycol and propylene glycol, non-aqueous vehicle such as animal and plant oil. The buffer, such as citrate, acetate, or phosphate, can be present to maintain pH, optionally between 6-8, and preferably between pH 6.5-7.5. Antioxidants such as ascorbic acid, sodium bisulphite can be present. The solubilizing agents and stabilizers such as cyclodextrin, lysolectin, oleic acid, stearic acid and dextrin can be present.

Preferably, the compound is administered in unit dosage form which contain an appropriate amount of active compound. The quantity of active compound, that is, compounds of Formula I in a dose, are varied or adjusted depending upon its potency and its particular application. In some embodiments, quantity ranges between 0.5% to 90% composition weight. In some embodiments, the suitable dosage of compound ranges about 0.1 to 5000 mg per human patient per day, for example from 50 to 2000 mg per human patient per day. In some embodiments, the dosage of compounds of Formula I can be divided in to 2-4 doses per day.

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active ingredient. In other embodiments, an active ingredient may comprise between about 2% to about 75% of the weight of the unit, or between about 25% to about 60%, for example, and any range derivable therein. Naturally, the amount of active ingredient(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158, 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating, preventing, or ameliorating a bacterial infection. Thus, provided herein is a method for treating microbial infections in patients by administering to a patient in need thereof an effective amount of a compound of Formula I. In some embodiments, the compound is administered in a pharmaceutical composition orally, parenterally, or topically. The treatment is not limited to microbial infections.

Furthermore, the compounds and compositions herein can be used in combination therapies. That is, the compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active ingredient in a way that the therapeutic effects of the first administered procedure or drug is not entirely disappeared when the subsequent procedure or drug is administered.

In certain embodiments, the compounds herein are useful in combination with other anti-infectives, such as antibacterial agents. Without wishing to be bound by theory, it is believed that the compounds herein use oxygen to inhibit cell walls, and are therefore especially useful in combination with other anti-infectives in low-oxygen environments. Suitable other antibacterial agents include, but are not limited to: soniazid, rifampin, pyrazinamide, fluoroquinolone, streptomycin, ethambutol, capreomycin, ethionamide, cycloserine, levofloxacin, ciprofloxacin, amikacin, moxifloxacin, p-amino salicylic acid, kanamycin, viomycin, prothionamide, rifabutin, clarithromycin, linezolid, Chioasetazon, arginine, vitamin B, or a corticosteroid.

It is further envisioned that the compositions and methods described herein can be embodied in the form of a kit or kits. A non-limiting example of such a kit is a kit for making a 2-aminothiophene derivative, the kit comprising ethyl cyanoacetate, sulfur, a piperidinone, and an acid chloride in two or more separate containers, where the containers may or may not be present in a combined configuration. One non-limiting example of such a kit has a first container housing oen or more of ethyl cyanoacetate, sulfur, and a piperidinone, and a second container housing an acid chloride. Many other kits are possible, such as kits for making a pharmaceutical composition that further comprise a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Further provided is a method of determining coverage of health insurance reimbursement or payments, the method comprising denying coverage or reimbursement for a treatment, wherein the treatment comprises a compound of Formula I.

EXAMPLES

Various compounds of Formula I were synthesized and tested for anti-microbial activity.

General Procedure for the Synthesis of 2-aminothiophene-3-carboxylate Cores A and B (FIG. 5, Scheme 1)

Ethyl cyanoacetate (0.53 g, 4.71 mmol), sulfur (0.18 g, 5.68 mmol), and ketone (1.0 g, 4.28 mmol) were suspended in EtOH (10.0 mL). Diethylamine (0.62 g, 8.57 mmol) was added and the mixture was heated to 70° C. for 3 h. After the reaction was complete, EtOH was evaporated under reduced pressure resulting in a brown solid, which was dissolved in $CH_2Cl_2$. The $CH_2Cl_2$ layer was washed with sat. $NH_4Cl$ (20.0 mL), deionized $H_2O$ (20.0 mL), and sat. NaCl (20.0 mL). After drying with anhydrous $NaSO_4$ and filtration, the solvent was evaporated and the crude product was purified by crystallization from cold MeOH to obtain product.

General Procedure for the Synthesis of 2-aminothiophene-3-carboxylate Cores C (FIG. 5, Scheme 1)

Ethyl cyanoacetate (4.89 g, 43.24 mmol), sulfur (1.66 g, 51.10 mmol), and 1-ethylpiperidine (5.0 g, 39.31 mmol) were suspended in EtOH (50.0 mL). Diethylamine (5.74 g, 78.62 mmol) was added and the mixture was heated to 70° C. for 12 h. After the reaction was complete, the EtOH was evaporated under reduced pressure to afford a brown solid. To the brown solid was added diethyl ether (30.0 mL) followed by sonication for 5 mins. The ether layer was decanted and this process was repeated twice to remove unreacted starting material. The solid compound was dissolved in ethyl acetate and filtered. The filtrate was concentrated under reduced pressure and crystallized from cold MeOH to obtain brown crystals. Yield: 75% (7.52 g); silica gel TLC $R_f$=0.50 (7% methanol in dichloromethane).

General Procedure for the Synthesis of 2-amidothiophene-3-carboxylate Cores D (FIG. 5, Scheme 1)

Compounds A-C, H (115.0 mg, 0.452 mmol) were dissolved in dry $CH_2Cl_2$ (1.0 mL), and cooled to 0° C. N,N-(dimethylamino)pyridine (22.10 mg, 0.180 mmol) and $Et_3N$ (137.0 mg, 1.350 mmol) were added to the solution followed by the dropwise addition of acid chloride (135.6 mg, 0.580 mmol). The resulting solution was allowed to warm to room temperature and allowed to stir for 12 h. After the reaction was complete, the $CH_2Cl_2$ was evaporated under reduced pressure to obtain a crude solid which was purified by flash column chromatography on silica gel (methanol:$CH_2Cl_2$) to obtain product.

General Procedure for the Deprotection of ethyl 2-aminothiophene-3-carboxylate ester Cores E (FIG. 5, Scheme 1)

The ethyl ester compounds A-C (1.0 g, 2.77 mmol) were dissolved in THF:$H_2O$:MeOH (3:1:1) to obtain a clear solution. LiOH (0.349 g, 8.33 mmol) was added to the solution, and then the solution was heated to 70° C. and maintained at that temperature for 12 h. The solution was concentrated to obtain a solid and then the solid was taken up in water and extracted with $Et_2O$ (20.0 mL) 3 times. The aqueous layer was acidified to pH ~3-4 using 6N HCl. The acidified $H_2O$ layer was extracted with EtOAc (20.0 mL×3). The combined EtOAc extracts were dried over anhydrous $Na_2SO_4$, filtered, and concentrated to obtain a solids which were crystallized from $CH_2Cl_2$.

General Procedure for the Synthesis of alkyl 2-aminothiophene-3-carboxamides Cores F (FIG. 5, Scheme 1)

A solution of carboxylic acid E (400 mg, 1.77 mmol) was dissolved in $CH_2Cl_2$ (3.6 mL) and was cooled to 0° C. A solution of the appropriate alkyl amine (236 mg, 1.95 mmol), and 1-(3-dimethylaminopropyl)-3-ethylcarbodiimide hydrochloride (339 mg, 1.77 mmol), 1-hydroxybenzotriazole hydrate (271 mg, 1.77 mmol), and N,N-(dimethylamino)pyridine (361 mg, 1.77 mmol) dissolved in $CH_2Cl_2$ (3.6 mL) was added. The solution was allowed to warm to room temperature and was stirred for 18 h. The solution was diluted with $CH_2Cl_2$ (15.0 mL), washed with brine (20.0 mL), dried over anhydrous $Na_2SO_4$, and concentrated to obtain a crude solid. The product was purified by flash column chromatography (methanol:$CH_2Cl_2$) to obtain a product F.

General Procedure for the Synthesis of 2-amidothiophene-3-carboxylate Cores G (FIG. 5, Scheme 1)

Compounds F were dissolved in dry $CH_2Cl_2$ and cooled to 0° C. N,N-(dimethylamino)pyridine and $Et_3N$ were added to the solution followed by the dropwise addition of acid chloride. The resulting solution was allowed to warm to room temperature and allowed to stir for 12 h. After the reaction was complete, the $CH_2Cl_2$ was evaporated under reduced pressure to obtain a crude solid which was purified by flash column chromatography on silica gel (methanol: $CH_2Cl_2$) to obtain product.

General Procedure for the Synthesis of 2-aminothiophene-3-carboxylate Cores, H

To a mixture of ethyl 2-cynoacetate (12.4 g) tetrahydro-4H-pyran-4-one (10.0 g, 0.10 mol) in (100.0 mL) absolute ethanol, sulfur (4.16 g, 0.12 mol) was added, followed by slow addition of morpholine (4.0 mL). The reaction was heated at 40-50° C. for 24 h. After that, it was filtrated and washed by EtOH to obtain crude product. The yellow crude product was purified by recrystallization from cold MeOH to obtain a lime yellow product. Yield: 20.5 g, 90%. Silica gel TLC $R_f$=0.45 (30% Ethyl acetate in Hexanes). $^1$H NMR (600 MHz, $CDCL_3$) δ ppm 1.34 (t, J=7.15 Hz, 3H) 2.80-2.85 (m, 2H) 3.92 (t, J=5.59 Hz, 2H) 4.27 (q, J=7.15 Hz, 2H) 4.56 (t, J=2.02 Hz, 2H); $^{13}$C NMR (151 MHz, $CDCL_3$) δ 166.0, 162.3, 130.4, 114.9, 105.6, 65.3, 64.7, 59.7, 27.8, 14.6; HRMS (ESI-MS) m/z: [M+Na]$^+$ Calcd for $C_9H_{10}N_2SNa$ 250.05; Found 250.04.

Core A Example: 6-Benzyl 3-ethyl 2-amino-4,7-dihydrothieno[2,3-c]pyridine-3,6(5H)-dicarboxylate Yield: 86% (1.36 g); silica gel TLC $R_f$=0.51 (40% ethyl acetate in hexanes); $^1$H-NMR (600 MHz, $CDCl_3$): δ 7.38 (m, 4H, H-19, 20, 22, 23), 7.33 (m, 1H, H-21), 6.02 (s, 2H, H-17), 5.17 (s, 2H, H-8), 4.44 (s, 2H, H-6), 4.26 (q, 2H, 2H, $J_{13,14}$ 6 Hz, H-13), 3.71 (s, 2H, H-10), 2.83 (m, 2H, H-5), 1.34 (t, 3H, $J_{14,13}$ 6 Hz, H-14); $^{13}$C-NMR (150 MHz, $CDCl_3$): δ 165.79 (C-2), 162.34 (C-110, 155.27 (C-15), 136.67 (C-18), 131.66 (C-9), 130 (C-22, 20), 128.10 (C-19, 23), 128 (C-21), 113.13 (C-4), 105.22 (C-5), 67.33 (C-17), 56.65 9C-13), 50.92 (C-8), 42.68 (C-6), 41.20 (C-5), 14.45 (C-14); mass spectrum (ESI), m/z=383.10 (M+23)$^+$ $C_{18}H_{20}N_2O_4S$ requires 383.10 (M+23)$^+$.

Core B Example: 6-(tert-butyl) 3-ethyl 2-amino-4,7-dihydrothieno[2,3-c]pyridine-3,6(5H)-dicarboxylate Yield: 63% (4.2 g); silica gel TLC $R_f$=0.49 (40% ethyl acetate in hexanes); $^1$H-NMR (600 MHz, $CDCl_3$): δ 4.36 (s, 2H, H-9), 4.27 (q, 2H, $J_{16,17}$ 6 Hz, H-16), 3.62 (t, 2H, $J_{2,3}$ 6 Hz, H-2), 2.81 (t, 2H, $J_{3,2}$ 6 Hz, H-3), 1.49 (s, 9H, H-13, 20, 21), 1.35 (t, 3H, $J_{16,17}$ 6 Hz, H-17); $^{13}$C-NMR (150 MHz, $CDCl_3$): 166.54 (C-2), 163.44 (C-11), 153.88 (C-13), 130.80 (C-4, 9), 102.61 (C-3), 79.08 (C-15), 42.48 (C-8), 41.45 (C-6), 28.07 (C-20, 19, 16), 14.11 (C-5); mass spectrum (ESI), m/z=349.1 (M+23)$^+$ $C_{15}H_{22}N_2O_4S$ requires 349.11 (M+23)$^+$.

Core C Example: Ethyl 2-amino-6-ethyl-4,5,6,7-tetrahydrothieno[2,3-c]pyridine-3-carboxylate Yield: 86% (140.0 mg); silica gel TLC $R_f$=0.2 (10% methanol in $CH_2C_{12}$); $^1$H-NMR (600 MHz, $CDCl_3$): δ 5.96

(s, 2H, H-10), 4.25 (q, 2H, $^3J_{15,16}$ 7.2 Hz, H-15), 3.43 (s, 2H, H-8), 2.84 (t, 2H, $^3J_{5,6}$ 8 Hz, H-5), 2.72 (t, 2H, $^3J_{6,5}$ 8 Hz, H-6), 2.58 (q, 2H, $^3J_{13,14}$ 7.2 Hz, H-13), 1.33 (t, 3H, $^3J_{16,15}$ 7.2 Hz, H-16), 1.17 (t, 3H, $^3J_{14,13}$ 7.2H-14); $^{13}$C-NMR (150 MHz, CDCl$_3$): δ 165.96 (C-2), 162.01 (C-11), 131.14 (C-4), 114.82 (C-9), 105.36 (C-3), 59.41 (C-15), 51.57 (C-12), 51.09 (C-8), 50.23 (C-6), 27.43 (C-5), 14.43 (C-16), 12.58 (C-14); mass spectrum (ESI), m/z=277.09 (M+23)$^+$ $C_{12}H_{18}N_2O_2S$ requires 277.10 (M+23)$^+$.

Core D Example: Ethyl 6-ethyl-2-(perfluorobenzamido)-4,5,6,7-tetrahydrothieno[2,3-c]pyridine-3-carboxylate (4{3,3,0})

Yield: 16% (34.0 mg); silica gel TLC R$_f$=0.38 (10% methanol in CH$_2$C$_{12}$); $^1$H-NMR (600 MHz, CDCl$_3$): δ 12.02 (s, 1H, H-10), 4.36 (q, 2H, $^3J_{7,18}$ 7.15 Hz, H-17), 3.65 (s, 2H, H-8), 2.97 (t, 2H, H-5) 2.82 (t, 2H, H-6), 2.68 (q, 2H, $^3J_{15,16}$ 6.79 Hz, H-15), 1.38 (t, 3H, $^3J_{18,17}$ 7.15 Hz, H-18), 1.22 (t, 3H, $^3J_{16,15}$ 7.15 Hz, H-16); $^{13}$C-NMR (150 MHz, CDCl$_3$): δ 166.39 (C-2), 154.13 (C-11), 146.35 (C-13), 145.14 ($^1J_{22,F}$ 256.39 Hz, C-22), 143.27 (md, $^1J_{22,F}$ 259.69 Hz, C-20,24), 137.99 (md, $^1J_{22,F}$ 255.29 Hz, C-23,21), 130.13 (C-4), 125.47 (C-9), 112.97 (C-3), 109.77 (C-19), 81.18 (C-17), 51.65 (C-15), 50.96 (C-8), 50.10 (C-6), 26.78 (C-5), 14.37 (C-18), 12.48 (C-16); mass spectrum (HRMS), m/z=449.0971 (M+H)$^+$ $C_{19}H_{18}F_5N_2O_3S$ requires 449.0953 M+H)$^+$.

Core E Example: 2-Amino-6-((benzyloxy)carbonyl)-4,5,6,7-tetrahydrothieno[2,3-c]pyridine-3-carboxylic acid Yield: 69% (617.0 mg); silica gel TLC R$_f$=0.55 (7% methanol in CH$_2$C$_{12}$); $^1$H-NMR (600 MHz, CDCl$_3$): δ 7.37 (m, 4H, H-18, 17, 21, 20), 7.32-7.31 (m, 1H, H-19), 5.10 (s, 2H, H-15), 4.31 (m, 2H, H-8), 3.59 (s, 2H, H-6), 2.68 (s, 2H, H-5); $^{13}$C-NMR (150 MHz, CDCl$_3$): δ166.49 (C-2), 163.51 (C-11), 154.51 (C-13), 136.86 (C-9), 130.75 (C-4), 128.43 (C-18, 20), 127.86 (C-21, 17), 127.55 (C-19), 111.56 (C-3), 42.47 (C-15), 41.13 (C-8), 40.73 (C-6), 26.77 (C-5); mass spectrum (HRMS), m/z=355.0732 (M+23)$^+$ $C_{16}H_{16}N_2O_4S$ requires 355.0723 (M+23)$^+$.

Core F Example: 2-Amino-N-benzyl-6-ethyl-4,5,6,7-tetrahydrothieno[2,3-c]pyridine-3-carboxamide Yield: 59% (140.0 mg); silica gel TLC R$_f$=0.57 (7% methanol in CH$_2$C$_{12}$); $^1$H-NMR (600 MHz, CDCl$_3$): δ 7.36-7.28 (m, 5H, H-18, 19, 20, 21, 22), 6.04 (s, 2H, H-10), 5.91 (s, 1H, H-15), 4.59 (d, 2H, $^3J_{16,15}$ 5.58 Hz, H-16), 3.46 (s, 2H, H-8), 2.74 (s, 4H, H-6, 5), 2.58 (q, 2H, $^3J_{13,14}$ 7.14, H-13), 1.16 (t, 3H, $^3J_{14,13}$ 7.14, H-14); $^{13}$C-NMR (150 MHz, CDCl$_3$): δ166.26 (C-2), 159.70 (C-11), 138.69 (C-9), 128.76 (C-21, 19), 127.45 (C-18, 20, 22, 4), 116.34 (C-17), 108.52 (C-3), 51.56 (C-16), 51.27 (C-8), 50.08 (C-6), 43.20 (C-13), 27.73 (C-5), 12.58 (C-14); mass spectrum (HRMS), m/z=316.1486 (M+H)$^+$ $C_{17}H_{21}N_3OS$ requires 316.1478 (M+23)$^+$.

Core G Example: 2-(3,5-Bis(trifluoromethyl)benzamido)-6-ethyl-N-(4-methylbenzyl)-4,5,6,7-tetrahydrothieno[2,3-c]pyridine-3-carboxamide Yield: 22% (18.0 mg); silica gel TLC R$_f$=0.55 (10% methanol in CH$_2$C$_{12}$); $^1$H-NMR (600 MHz, CDCl$_3$): δ 13.65 (s, 1H, H-10), 8.47 (s, 2H, H-22,18), 8.08 (s, 1H, H-20), 7.23 (d, 2H, J$_{33,35}$ 6 Hz, H-33,28), 7.19 (d, 2H, J$_{35,33}$ 6 Hz, H-35,29), 6.23 (s, 1H, H-23), 4.63 (d, 2H, J$_{26,23}$ 5 Hz, H-26), 3.71 (s, 2H, H-8), 2.87 (m, 4H, H-5,6), 2.70 (q, 2H, J$_{15,16}$ 6 Hz, H-15), 2.36 (s, 3H, H-34), 1.23 (t, 3H, J$_{16,15}$ 6 Hz, H-16); $^{13}$C-NMR (150 MHz, CDCl$_3$): δ 166.20 (C-2), 160.74 (C-13), 145.91 (C-11), 136.03 (C-30), 134.67 (C-17, 27), 132.52 (C-19, 21), 129.75 (C-35, 29), 127.78 (C-22, 18), 126.13 (C-4), 125.84 (C-20), 123.90, 120.29 (C-9), 114.65 (C-3), 51.74 (C-15), 51.10 (C-8), 49.93 (C-6), 43.64 (C-26), 26.96 (C-5), 21.27 (C-34), 12.35 (C-16); mass spectrum (HRMS), m/z=592.1467 (M+23)$^+$ $C_{27}H_{25}F_6N_3NaO_2S$ requires 592.1464 (M+23)$^+$.

Core H: Ethyl 2-(perfluorobenzamido)-4,7-dihydro-5H-thieno[2,3-c]pyran-3-carboxylate Yield: 188.0 mg 50.5%; silica gel TLC R$_f$=0.65 (30% Ethyl acetate in Hexanes); $^1$H NMR (600 MHz, CDCL$_3$) δ 12.05 (br. s., 1H), 7.28 (s, 1H), 4.77 (s, 2H), 4.39 (q, f=7.2 Hz, 2H), 3.99 (t, f=5.7 Hz, 2H), 2.94 (t, J=5.6 Hz, 2H), 1.41 (t, J=7.2 Hz, 3H); $^{13}$C NMR (151 MHz, CDCL$_3$) δ 166.3, 154.2, 146.5, 145.21 (md, J=256.39 Hz) 143.33 (md, J=261.0 Hz) 138.03 (md, J=255.29 Hz), 129.4, 125.9, 113.2, 109.7, 65.1, 64.8, 61.3, 27.1, 14.4; HRMS (ESI-MS) m/z: [M+H]' Calcd for $C_{17}H_{13}F_5NO_4S$, 422.0480, Found 422.0482.

6-Ethyl-2-(perfluorobenzamido)-4,5,6,7-tetrahydrothieno[2,3-c]pyridine-3-carboxamide (506)

Yield: 80 mg, 20%. Silica gel TLC R$_f$=0.46 (10% MeOH in CH$_2$C$_{12}$). $^1$H NMR (600 MHz, DMSO-d$_6$) δ 12.46-12.29 (m, 1H), 10.74-10.48 (m, 2H), 4.64-4.54 (m, 1H), 4.31-4.21 (m, 1H), 3.73-3.63 (m, 1H), 3.35-3.20 (m, 3H), 3.14-3.03 (m, 2H), 1.32 (t, f=7.2 Hz, 3H); $^{13}$C NMR: (150 MHz, DMSO-d$_6$) δ 6.98, 19.75, 45.63, 45.72, 47.55, 108.1, 117.2, 126, 136.2, 135.3, 138.53, 142, 144.5, 152.8, 163.4 ppm. HRMS (ESI-MS) m/z: [M+H]$^+$ Calcd for $C_{17}H_{15}F_5N_3O_2S$, 420.0800, Found 420.0813.

N,6-diethyl-2-(perfluorobenzamido)-4,5,6,7-tetrahydrothieno[2,3-c]pyridine-3-carboxamide (507)

Yield: 102.0 mg, 15%. Silica gel TLC R$_f$=0.77 (10% MeOH in CH$_2$C$_{12}$). $^1$H NMR (600 MHz, DMSO-d$_6$) δ 12.14 (br. s., 1H), 11.74 (br. s., 1H), 8.18 (br. s., 1H), 4.60-4.20 (m, 2H), 3.60 (br. s., H), 3.33-3.17 (m, J=6.1 Hz, 5H), 3.15-3.00 (m, 2H), 1.35 (t, J=7.2 Hz, 3H), 1.11 (t, J=6.7 Hz, 3H); $^{13}$C NMR (151 MHz, METHANOL-d$_4$) δ 166.2, 156.3, 149.5, 146.2, 143.2, 139.3, 128.6, 121.0, 120.7, 52.6, 50.6, 50.5, 35.9, 23.9, 14.9, 10.1; HRMS (ESI-MS) m/z: [M+H]$^+$ Calcd for $C_{19}H_{19}F_5N_3O_2S$, 448.1113, Found 448.1121.

Ethyl 7-oxo-2-(perfluorobenzamido)-4,5,6,7-tetrahydrothieno[2,3-c]pyridine-3-carboxylate (508)

Yield: 168.7 mg, 42%. Silica gel TLC R$_f$=0.81 (10% MeOH in CH$_2$C$_{12}$). $^1$H-NMR (600 MHz, DMSO-d$_6$) δ 12.04 (s, 1H), 7.83 (s, 1H), 4.32 (q, 2H), 3.44 (t, 2H), 3.02 (t, 2H), 1.30 (t, 3H). $^{13}$C-NMR: (150 MHz, CDCl$_3$) δ 13.91, 24.62, 28.2, 30.72, 60.2, 113.8, 120.1, 128, 137, 139, 142.21, 161.8, 163.94. HRMS (ESI-MS) m/z: [M+H]$^+$ Calcd for $C_{17}H_{12}F_5N_2O_4S$, 435.0438, Found 435.0547.

6-Ethyl-N-methyl-2-(perfluorobenzamido)-4,5,6,7-tetrahydrothieno[2,3-c]pyridine-3-carboxamide (509)

Yield: 50.1 mg, 28%. Silica gel TLC R$_f$=0.59 (10% MeOH in CH$_2$C$_{12}$). $^1$H NMR (600 MHz, DMSO-d$_6$) δ 12.17

(br. s., 1H) 10.33 (br. s., 1H) 9.73 (br. s., 1H) 4.02-4.56 (m, 2H) 3.40-3.91 (m, 2H) 2.92-3.28 (m, 4H) 2.70 (br. s., 3H) 1.26 (br. s., 3H); $^{13}$C NMR (151 MHz, DMSO-d$_6$) δ165.7, 158.0, 155.3, 143.7, 139.7, 137.0, 128.9, 117.4, 114.6, 113.1, 50.3, 49.2, 28.7, 24.9, 24.4, 9.3; HRMS (ESI-MS) m/z: [M+H]$^+$ Calcd for C$_{18}$H$_{17}$F$_5$N$_3$O$_2$S, 434.0956, Found 434.0950.

N-(3-Cyano-6-ethyl-4,5,6,7-tetrahydrothieno[2,3-c]pyridin-2-yl)-2,3,4,5,6-pentafluorobenzamide (510)

Yield: 0.98 g, 34%. Silica gel TLC R$_f$=0.47 (10% MeOH in CH$_2$C$_{12}$). $^1$H-NMR: (600 MHz, DMSO-d$_6$) δ 9.85 (s, 1H), 4.17 (s, 2H), 3.33 (s, 2H), 2.81 (s, 2H), 2.50 (s, 2H), 1.25 (t, J=6.8 Hz 3H); $^{13}$C NMR (151 MHz, DMSO-d$_6$) δ 159.5, 143.02 (md, J=246.49 Hz) 139.91 (md, J=244.29 Hz) 136.08 (md, J=249.79 Hz), 126.9, 116.9, 112.8, 112.0, 91.2, 54.9, 50.3, 49.1, 48.6, 21.7, 9.8. $^{13}$C NMR (151 MHz, DMSO-d$_6$) δ 159.5, 143.0, 139.9, 136.1, 126.9, 116.9, 112.8, 112.0, 91.2, 54.9, 50.3, 49.1, 48.6, 21.7, 9.8, 8.6; HRMS (ESI-MS) m/z: [M+H]$^+$ Calcd for C$_{17}$H$_{13}$F$_5$N$_3$OS 402.0694, Found 402.0692.

N-(3-Cyano-4,7-dihydro-5H-thieno[2,3-c]pyran-2-yl)-2,3,4,5,6-pentafluorobenzamide (511)

Yield: 1.19 g, 38.6%. Silica gel TLC R$_f$=0.81 (10% MeOH in CH$_2$C$_{12}$). $^1$H NMR (600 MHz, DMSO-d$_6$) δ 12.84 (s, 1H) 4.66 (s, 2H) 3.90 (t, J=5.59 Hz, 2H) 2.65 (t, J=5.50 Hz, 2H); $^{13}$C NMR (151 MHz, DMSO-d$_6$) δ 155.0, 145.6, 143.60 (md, J=249.79 Hz) 142.09 (md, J=255.29 Hz) 137.00 (md, J=249.79 Hz), 129.7, 126.9, 113.3, 110.1, 94.9, 63.8 (2C), 54.9, 24.0; HRMS (ESI-MS) m/z: [M+H]$^+$ Calcd for C$_{15}$H$_7$F$_5$N$_2$O$_2$S, 375.0221, Found 375.0240.

Ethyl 2-(perfluorobenzamido)-4,7-dihydro-5H-thieno[2,3-c]pyran-3-carboxylate (512)

Yield: 188.0 mg 50.5%; silica gel TLC R$_f$=0.65 (30% Ethyl acetate in Hexanes); $^1$H NMR (600 MHz, CDCl$_3$) δ 12.05 (br. s., 1H), 7.28 (s, 1H), 4.77 (s, 2H), 4.39 (q, J=7.2 Hz, 2H), 3.99 (t, J=5.7 Hz, 2H), 2.94 (t, J=5.6 Hz, 2H), 1.41 (t, J=7.2 Hz, 3H); $^{13}$C NMR (151 MHz, CDCl$_3$) δ 166.3, 154.2, 146.5, 145.21 (md, J=256.39 Hz) 143.33 (md, J=261.0 Hz) 138.03 (md, J=255.29 Hz), 129.4, 125.9, 113.2, 109.7, 65.1, 64.8, 61.3, 27.1, 14.4; HRMS (ESI-MS) m/z: [M+H]' Calcd for C$_{17}$H$_{13}$F$_5$NO$_4$S, 422.0480, Found 422.0482.

Ethyl 6-heptyl-2-(perfluorobenzamido)-4,5,6,7-tetrahydrothieno[2,3-c]pyridine-3-carboxylate (513)

Yield: 203 mg, 83%. $^1$H NMR (600 MHz, CDCl$_3$) δ12.02 (s, 1H), 4.36 (q, J=7.1 Hz, 2H), 3.60 (s, 2H), 2.93 (t, J=5.7 Hz, 2H), 2.77 (t, J=5.7 Hz, 2H), 2.59-2.50 (m, J=7.5 Hz, 2H), 1.63-1.56 (m, J=7.2 Hz, 3H), 1.39 (t, J=7.2 Hz, 3H), 1.36-1.28 (m, 9H), 0.90 (t, J=7.0 Hz, 3H); $^{13}$C NMR (151 MHz, CDCl$_3$) δ 166.4, 154.0, 146.1, 143.27 (md, J=270.70 Hz) 137.84 (md, J=259.69 Hz) 134.96 (md, J=227.78 Hz), 130.1, 126.0, 112.9, 109.7, 61.0, 57.9, 51.5, 50.4, 31.8, 29.3, 27.5, 27.4, 26.9, 22.7, 14.3, 14.1; HRMS (ESI-MS) m/z: [M+H]$^+$ Calcd for C$_{24}$H$_{28}$F$_5$N$_2$O$_3$S, 519.1735, Found 519.1739.

Ethyl 2-(perfluorobenzamido)-4,5,6,7-tetrahydrothieno[2,3-c]pyridine-3-carboxylate (514)

Yield: 385.6 mg, 95%. Silica gel TLC R$_f$=0.21 (20% EtOAc in Hexanes). $^1$H NMR (600 MHz, CDCl$_3$) δ 12.44 (br. s., 1H), 12.18-12.03 (m, 1H), 4.40 (d, J=7.2 Hz, 4H), 3.55 (d, J=5.1 Hz, 2H), 3.24 (t, J=6.0 Hz, 2H), 1.40 (t, J=7.2 Hz, 3H); $^{13}$C NMR (151 MHz, CDCl$_3$) δ 165.6, 161.7, 154.9, 148.0, 145.43 (md, J=254.19 Hz), 143.64 (md, J=260.79 Hz), 138.10 (md, J=255.29 Hz), 128.9, 118.4, 116.6, 114.7, 112.7, 109.0, 61.9, 42.1, 42.0, 23.4, 14.2; HRMS (ESI-MS) m/z: [M+H]$^+$ Calcd for C$_{17}$H$_{14}$F$_5$N$_2$O$_3$S, 421.0640, Found 421.0648.

2-(Perfluorobenzamido)-4,7-dihydro-5H-thieno[2,3-c]pyran-3-carboxamide (515)

Yield: 983.0 mg, 35%). Silica gel TLC R$_f$=0.82 (10% MeOH in CH$_2$C$_{12}$). $^1$H NMR (600 MHz, DMSO-d$_6$) δ 12.92 (s, 1H), 4.83 (s, 2H), 3.95 (t, J=5.5 Hz, 2H), 2.93 (t, J=5.5 Hz, 2H); $^{13}$C NMR (151 MHz, DMSO-d$_6$) δ 160.0, 157.4, 153.5, 149.6, 143.5 (d, J=250.89 Hz, 1C), 142.5 (d, J=256.39 Hz), 137.1 (d, J=249.79 Hz), 134.5, 129.6, 117.0, 110.3, 64.4, 63.7, 25.4; HRMS (ESI-MS) m/z: [M+H]$^+$ Calcd for C$_{15}$H$_{10}$F$_5$N$_2$O$_3$S, 393.0327, Found 393.0390.

Discussion

A library of 42 2-aminothiophene compounds was synthesized. Among these, compound 4{3,3,0} showed remarkable potency against *Mycobacterium tuberculosis* (Mtb) H37RV (MIC=0.23 µM), and showed an impressive potency (MIC=0.20-0.44 µM) against Mtb strains resistant to isoniazid, rifampicin, and fluoroquinolones. Without wishing to be bound by theory, the site of action for the compound 4{3,3,0} is believed to be Pks13 or an earlier enzyme in the mycolic acid biosynthetic pathway. This inference is based structural similarity of the compound 4{3,3,0} with known Pks13 inhibitors, which is corroborated by mycolic acid biosynthesis studies which show the compound strongly inhibits the biosynthesis of all forms of mycolic acid in Mtb. In summary, this example indicates that 4{3,3,0} is a useful anti-TB compound which showed activity well below toxicity to human monoocytic cells.

The compounds were screened for growth inhibition against Mtb H37Rv using a modified 96-well microplate Alamar blue assay (MABA). The MABA identified thiophenes with MICs ranging from 0.31 to >200 µg/mL, in which compound 4{3,3,0} showed potent Mtb growth inhibition MIC=0.31 µg/mL. The activity assay for 4{3,3,0} was repeated on Mtb H37Rv modified with a fluorescent reporter and grown under aerobic and low oxygen conditions. The data confirmed 4{3,3,0} to be very potent with an MIC=0.23 µM under aerobic conditions. Additional activity screens revealed 4{3,3,0} to be active against common drug resistant reference strains of Mtb. To determine whether or not any of the compounds inhibited Ag85s, a high throughput screening of the compound library against Ag85C was performed using a fluorescence-based assay. None of the compounds in the library showed inhibition below 100 µg/mL against Ag85C. Without wishing to be bound by theory, it is believed that the compounds herein are Pks13 inhibitors or target an earlier enzyme in the mycolic acid biosynthetic pathway. In order to confirm this, the effect of 4{3,3,0} on mycolic acid biosynthesis was characterized. In those experiments, Mtb cultures containing 14C-labeled acetate were exposed to 4{3,3,0}, and the levels of TMM, TDM, and mAG-attached mycolates were determined following TLC analysis and autoradiography. The experiments revealed that 4{3,3,0} strongly inhibits the synthesis of all forms of mycolic acids in the cell envelope.

Two types of 2-aminothiophenes (2AT) were prepared: (i) fused ring 2-amino thiophenes (FRT) formed from cores 3{1,0,0}-3{4,0,0}, and (ii) 2-amino-5-phenylthiophenes (5PT) compounds formed from core 3{5,0,0}. The four FRT cores were synthesized from ketones 2 containing an active methylene group. The ketones were: benzyl 4-oxopiperidine-1-carboxylate 2{1}, tert-butyl 4-oxopiperidine-1-carboxylate 2{2}, 1-ethylpiperidin-4-one 2{3}, and cyclohexanone 2{4}. The 5PT core was synthesized from 2-phenylacetaldehyde 2{5}, (Scheme 2, FIG. 6). 2-Alkylamido compounds 4{a,b,c} were synthesized from 3{1,0,0}-3{5,0,0} using acid chlorides (AC). The ACs used were: acetyl chloride, benzoyl chloride, 2,3,4,5,6-pentafluorobenzoyl chloride, and 3,5-bis(trifluoromethyl)benzoyl chloride. The 3-carboxamide compounds 6{a,b,c} were synthesized using alkylamines (AA): butylamine, benzylamine, 4-methylbenzylamine, 2-methoxybenzylamine, and adamantylamine (Scheme 2, FIG. 6).

The core compounds 3{1,0,0}-3{5,0,0} (Scheme 2, FIG. 6) were synthesized using Gewald chemistry. This reaction involves the use of aldehyde or ketone 2{1}-2{5} with the activated nitrile, ethyl 2-cyanoacetate (1), in presence of elemental sulfur ($S_8$) and diethylamine to obtain the respective cores. The cores 3{1,0,0}-3{5,0,0}, on reacting with ACs 1-4 in presence of DMAP and $Et_3N$, vary the $R^2$ group and afford 2-alkylamido compounds 4{a,b,c}. The 3-carboxamide compounds labelled 6{a,b,c} were accessed by deprotection of the ethyl ester 3 with LiOH to obtain compounds labeled 5{1,0,0}-5{5,0,0}, which on further treating with AAs 1-5 using coupling reagent 1-ethyl-3-(3-dimethylaminopropyl)carbodiimide (EDC.HCl), hydroxybenzotriazole (HOBt), and DMAP, afforded 3-carboxamide compounds (labeled 6{a,b,c}) (FIG. 7).

Growth Inhibition and Cytotoxicity

The 2-aminothiophene library (FIG. 7) was subjected to growth inhibition studies using a modified 96-well MABA, Table 2 (FIG. 8). Among these compounds 4{3,3,0}, 4{4,3,0}, and 5{5,0,0} showed MIC≤50 µg/mL, whereas compound 5{4,0,0} showed an MIC=100 µg/mL. The compounds 3{4,0,0}, 4{3,4,3}, and 4{4,2,0} showed MIC of ≥200 µg/mL, and the remainder of the compounds showed MIC>100 µg/mL. The most potent compound was 4{3,3,0}, with a MIC=0.31 µg/mL (Table 2, FIG. 8). Having identified 4{3,3,0}, a second set of assays were conducted to confirm the MIC of 4{3,3,0} and determine $IC_{50}$ and $IC_{90}$ values for this compound, using Mtb H37Rv grown under aerobic as well as low oxygen conditions. These MICS assays were based on measurement of growth in liquid medium of a fluorescent (mCherry) reporter strain of Mtb H37Rv where the readout is either optical density (OD) or fluorescence. In addition, the antimicrobial activity of compounds against Mtb H37Rv grown under hypoxic conditions was assessed using a low oxygen recovery assay (LORA). In this assay, bacteria are first adapted to low oxygen conditions and then exposed to compounds under hypoxia; this is followed by a period of outgrowth in aerobic conditions and growth is measured using luminescence. The mCherry assay confirmed the initial screening result and showed and MIC=0.23 µM (Table 1, FIG. 4A). The LORA showed an MIC>200 µM, $IC_{50}$=0.27 µM, and $IC_{90}$=15 µM. This result is considered activity under low oxygen; however, this activity is less than the control compound rifampicin (RIF) which shows an MIC=0.048 µM under the same conditions.

Figure 9:
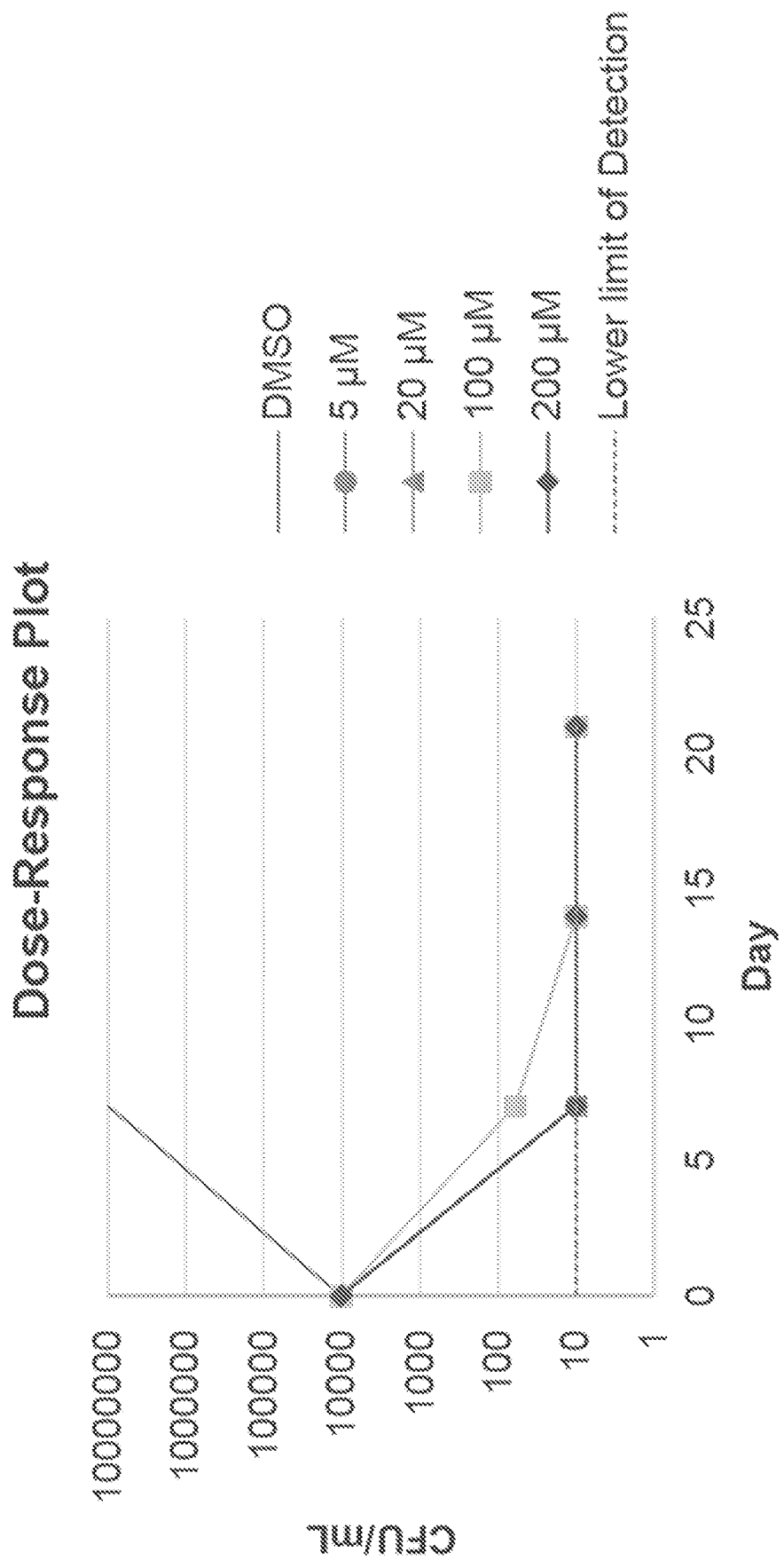
FIG. 9: The bactericidal activity of 4{3,3,0} assessed against Mtb H37Rv grown in aerobic conditions in 7H9-Tw-OADC medium. Viable cell counts are measured over 3 weeks of exposure to determine the rate of kill.

The bactericidal activity of 4{3,3,0} was assessed against Mtb H37Rv grown in aerobic conditions in 7H9-Tw-OADC medium. Viable cell counts were measured over 3 weeks of exposure to determine the rate of kill. Compounds were tested at fixed concentrations, as no MIC data were available at the time of the experiment. Concentration of 200, 100, 20, and 5 µM 4{3,3,0} were used. The MBC was found to be <5 µM (FIG. 9).

The cytotoxicity of 4{3,3,0} towards eukaryotic cells was determined using the THP-1 human monoocytic cell line. THP-1 cells were differentiated into macrophage-like cells using phorbol 12-myristate 13-acetate (PMA) and incubated with compounds for 3 day after which time cell viability was measured. For 4{3,3,0}, the $IC_{50}$=6.2 µM, which represents the concentration of compound causing a 50% loss in viability. The intracellular activity of 4{3,3,0} was measured using THP-1 cells infected with an autoluminescent Mtb strain derived from Mtb H37Rv. THP-1 cells were again differentiated into macrophage-like cells using PMA and infected with bacteria. Infected cells were exposed to compounds for 72 hours. Viable bacterial counts were measured using luminescence as a measure of growth. The result is shown in Table 1 (FIG. 4A) and is reported as an $IC_{50}$=5.6 µM, which compares to and $IC_{50}$=0.24 µM for INH.

The activity of 4{3,3,0} against five resistant isolates of Mtb strains was assessed under aerobic conditions by determining the MIC. Strains tested were two isoniazid resistant strains (INH-R1 and INH-R2), two rifampicin resistant strains (RIF-R1 and RIF-R2), and a fluoroquinolone resistant strain (FQ-R1). The assay was based on measurement of growth in liquid medium of each strain where the readout wais OD. INH-R1 was derived from H37Rv and is a katG mutant (Y155*=truncation). INH-R2 is strain ATCC 35822. RIF-R1 was derived from H37Rv and is an rpoB mutant (S522L). RIF-R2 is strain ATCC 35828. FQ-R1 is a fluoroquinolone-resistant strain derived from H37Rv and is a gyrB mutant (D94N). The MICs of control antibiotics (RIF, INH, and Levofloxacin) are shown in FIG. 12. Compound 4{3,3,0} showed potent activity MIC=0.20-0.44 µM against the five resistance isolates tested (Table 2). Control data for INH, RIF, and Levofloxacin is also reported (Table 2) for comparison.

Effect of 4{3,3,0} on Mycolic Acid Synthesis

To assess the inhibitory effect of 4{3,3,0} on mycolic acid biosynthesis, Mtb cultures exposed to different concentrations of 4{3,3,0} were metabolically labeled with [1,2-14C] acetate and the levels of TMM, TDM, and mAG-attached mycolates were determined following TLC analysis and autoradiography. The experiments reveealed that 4{3,3,0} strongly inhibits the synthesis of all forms of mycolic acids in the cell envelope.

Structure activity relationships (SAR)

The structures of FRT and 5PT compounds were divided into IV, $R^2$, and $R^3$ for FRTs, and $R^2$ and $R^3$ for 5PT, respectively (FIG. 7). The most significant relation was the introduction of $COC_6F_5$ at the $R^2$ position, which resulted in a sharp increase in potency. It could be seen that 4{4,3,0} (MIC=12.5 µg/mL) was significantly more potent than the non-fluoronated homolog 4{4,2,0}, which showed no activity.

The significant finding of this Example is the observation that a NEt group in an aliphatic ring at the $R^1$ position of compound 4{3,3,0} showed 40-fold increase in potency compared to compound 4{4,3,0} using the MABA. Without wishing to be bound by theory, it is believed that the R=NEt group is isosteric with compounds related to 1 (FIG. 1). Another observation was that replacement of the NEt with a bulky groups like N-Boc at $R^1$ had a detrimental effect, making compound 4{2,3,0} inactive even with a $COC_6F_6$ substituent at the $R^2$.

The activity requirement for the ethyl ester at $R^3$ position is less well defined. There was slight activity observed for 4{3,4,3} (MIC=200 µg/mL), which bears an $R^3$ benzamide moiety, in comparison to 4{3,4,0} (MIC>100 µg/mL), which bears an $R_3$ ethoxy moiety. This $R^3$ substitution was not prepared with an $R^2$=$COC_6F_5$ group, but, rather, the 3,5-trifluoromethylbenzamide. Thus, the fact that any activity at all was observed is somewhat surprising as it indicates that compounds with further improvements in potency are obtainable. In other compounds, substituting the ethyl ester with an amide at $R_3$ can result in a significant increase in MIC. The structural similarity of 4{3,3,0} to certain known Pks13 inhibitors indicates the compound may inhibit Pks13. The 5PT compounds all showed poor to no potency, as all the MICs were ≥100 µg/mL. This result indicates that six membered ring attached to thiophene is important for growth inhibition activity, as even compound 4{5,3,0} with an $R^2$ 2-(perfluorobenzamido) group showed an MIC>100 µg/mL.

Compound 4{3,3,0} was selected for further evaluation using Mtb H37Rv grown under aerobic conditions using a fluorescent reporter strain Mtb H37Rv. This strain has been fully characterized and is equivalent to the parental strain in microbiological phenotypes and virulence. The activity under aerobic conditions was confirmed and found to be 0.23 µM. The MBC of 4{3,3,0} was then assessed and found to be below 5 µM, which indicates that 4{3,3,0} is bactericidal. The antimicrobial activity of 4{3,3,0} against Mtb H37Rv grown under hypoxic conditions was assessed using a LORA. The purpose of the latter assay was to evaluate 4{3,3,0} on Mtb placed in a state of nonreplicating persistence (NRP). Bacteria were first adapted to low oxygen conditions and then exposed to 4{3,3,0} under hypoxia; this was followed by a period of outgrowth in aerobic conditions and growth is measured using luminescence. The $MIC_{50}$=0.27 µM and $MIC_{90}$=15 µM under LORA conditions indicated limited activity under low oxygen conditions (the $MIC_{90}$ is 65 times higher than under aerobic conditions). However, this data provides insight into the mechanism of action. It is known that agents targeting the cell wall of Mtb (eg, INH, ethambutol, and others) show greatly reduced activity against NRP Mtb, whereas drugs hitting other cellular targets have a range of activities. This result is therefore considered validation that 4{3,3,0} targets cell wall biosynthesis.

Mtb can escape the action of antibiotics by hiding inside of macrophages. Therefore, both the cytotoxicity of 4{3,3,0} and activity against human macrophages infected with Mtb were evaluated. The first assay revealed an $IC_{50}$=6.2 µM for macrophage viability. This value is 27 times higher than the MIC, and provides a starting point for optimizing the therapeutic window of the compound class. Importantly, 4{3,3,0} was active on Mtb infected macrophages showing an $IC_{90}$=9.75 µM. The data indicates a loss of activity in comparison to INH, which does not lose activity (based on $IC_{90}$ values) in Mtb infected macrophages. This data indicates compound permeability may be further improved.

Multidrug-resistant tuberculosis (MDR-TB) is a growing problem and is due to a resistance to INH and RIF, two of the most powerful antituberculosis drugs. Fluoroquinolones (FQs) have emerged as the most important drugs in second-line treatment of MDR-TB. However, extensively drug-resistant TB (XDR-TB) has emerged and is defined as MDR-TB with additional resistance to fluoroquinolones and at least one of the injectable drugs amikacin, capreomycin, and kanamycin. New antitubercular agents should have activity against major and emerging drug-resistant strains of Mtb. The panels of resistance strains evaluated includes INHR1, which contains a mutation in the catalase-peroxidase enzyme KatG protein which activates the prodrug INH to its active form. The RIF-R1 strain contains a S522L mutation in the rpoB gene. Mutations in that region of the selected region of the gene are responsible for most rifamycin resistance in Mtb. To cover XDR-TB, the panel contained FQ-R1, which has an amino acid substitution within the GyrB subunit of DNA gyrase. The results of these studies showed that 4{3,3,0} is highly active against Mtb strains resistant to these three classes of antitubercular agents.

Conclusions

In these Examples, a 2AT compound with excellent activity, 4{3,3,0} MIC=0.23 µM, which inhibits mycolic acid biosynthesis in Mtb, was prepared and tested. This compound is the most potent 2AT yet discovered. The 2AT library was screened against Ag85C, however, no significant activity was observed below 100 µg/mL. Based on structural similarities with other compounds, 4{3,3,0} is believed to be a Pks13 inhibitor, or to target an earlier enzyme in the mycolic acid biosynthetic pathway. The loss of antibacterial activity under NRP culture conditions indicates that the compounds are targeting mycolic acid biosynthesis. Importantly, the compounds are active against laboratory generated and reference INH, RIF, and FQ resistant Mtb strains. This indicates the compounds are active against MDR and XDR strains of Mtb. Compound 4{3,3,0} was active at concentrations below concentrations that effect the viability of human macrophage-like cells; however, the reduced activity in Mtb infected macrophage-like cells indicates the physical properties may be further improved.

Materials and Methods

All starting materials were purchased from Acros Organics or Sigma Aldrich. Unless specified, all the reactions were performed under nitrogen atmosphere. Reactions were monitored by thin-layer chromatography (TLC, silica gel 60 F254) and spots were observed by UV-lamp. All solvents used for reactions were purchased from Sigma Aldrich and Fisher Scientific, which were purified and dried by distillation and other standard procedures. Solvents for flash column chromatography were used as purchased. Purification of compounds was performed by flash chromatography on silica gel (porosity 60 Å, 230-400 mesh) from Sorbent Technologies. $^1$H NMR, $^{13}$C NMR, G-COSY, and HMQC spectra were carried out using a Bruker Avance III 600 spectrometer in Fourier transformation mode. $^1$H-NMR and $^{13}$C-NMR were referenced to residual $CDCl_3$ peak at 7.27 ppm, and 77.16 ppm, respectively. High resolution mass spectroscopy (HRMS) was performed on a micro mass Q-TOF2 instrument.

General Procedure for Synthesis of 2-aminothiophene-3-carboxylate (Thiophene Cores: 3{1,0,0}, 3{2,0,0}, 0.3{4,0,0}, and 3{5,0,0})

The ethyl cyanoacetate (0.53 g, 4.71 mmol), sulfur (0.18 g, 5.68 mmol), and α-methylene carbonyl compound (1.0 g, 4.28 mmol) were suspended in EtOH (10.0 mL). Diethylamine (0.62 g, 8.57 mmol) was added and the mixture was heated to 70° C. for 3 h. After the reaction was complete, EtOH was evaporated under reduced pressure resulting in a brown solid, which was dissolved in $CH_2Cl_2$. The $CH_2Cl_2$ layer was washed with sat. $NH_4Cl$ (20.0 mL), deionized $H_2O$ (20.0 mL), and sat. NaCl (20.0 mL). After drying with anhydrous $NaSO_4$ and filtration, the solvent was evaporated and the crude product was purified by crystallization from cold MeOH to obtain a lime yellow product. Yield: 79% (1.21 g); silica gel TLC Rf=0.50 (40% ethyl acetate in hexanes).

General Procedure for 2-aminothophene-3-carboxylate formation with 1-ethylpiperidin-4-one 3{3,0,0}

The ethyl cyanoacetate (4.89 g, 43.24 mmol), sulfur (1.66 g, 51.10 mmol), and 1-ethylpiperidine (5.0 g, 39.31 mmol) were suspended in EtOH (50.0 mL). Diethylamine (5.74 g, 78.62 mmol) was added and the mixture was heated to 70° C. for 12 h. After the reaction was complete, the EtOH was evaporated under reduced pressure to afford a brown solid. To the brown solid was added diethyl ether (30.0 mL) followed by sonication for 5 mins. The ether layer was decanted and this process was repeated twice to remove unreacted starting material. The solid compound was dissolved in ethyl acetate and filtered. The filtrate was concentrated under reduced pressure and crystallized from cold MeOH to obtain brown crystals. Yield: 75% (7.52 g); silica gel TLC Rf=0.50 (7% methanol in dichloromethane).

General Procedure for 2-amidothiophene-3-carboxylate compounds (Compounds Labeled with 4{a,b,c} where a=thiophene cores, b=ACs, and C=AAs, FIG. 6)

Compound 3{3,0,0} (115.0 mg, 0.452 mmol), was dissolved in dry $CH_2Cl_2$ (1.0 mL) and cooled to 0° C. N,N-(dimethylamino)pyridine (22.10 mg, 0.180 mmol), and $Et_3N$ (137.0 mg, 1.350 mmol) were added to the solution followed by the dropwise addition of acid chloride (135.6 mg, 0.580 mmol). The resulting solution was allowed to warm to room temperature and allowed to stir for 12 h. After the reaction was complete the $CH_2Cl_2$ was evaporated under reduced pressure to obtain a crude solid which was purified by flash column chromatography on silica gel (methanol:$CH_2Cl_2$) to obtain a lime yellow product 4{3,3,0}. Yield: 45% (101.19 mg); silica gel TLC Rf=0.38 (10% methanol in $CH_2C_{12}$).

General Procedure for Deprotection of ethyl 2-aminothiophene-3-carboxylate ester Cores (Compounds 5{1,0,0} to 5{5,0,0} (Exception Compound 5{3,0,0}))

The ethyl ester compounds (1.0 g, 2.77 mmol) were dissolved in THF:$H_2O$:MeOH (3:1:1) to obtain a clear solution. LiOH (0.349 g, 8.33 mmol) was added to the solution and then the solution was heated to 70° C. and maintained at that temperature for 12 h. The solution was concentrated to obtain a solid and then the solid was taken up in water and extracted with $Et_2O$ (20.0 mL) 3 times. The aqueous layer was acidified to pH ~3-4 using 6N HCl. The acidified $H_2O$ layer was extracted with EtOAc (20.0 mL×3). The combined EtOAc extracts were dried over anhydrous $Na_2SO_4$, filtered and concentrated to obtain a solid which was crystallized from $CH_2Cl_2$ and hexanes to obtain a crystalline brown-yellow product 5{1,0,0}. Yield: 69% (687.7 mg); silica gel TLC Rf=0.26 (40% ethyl acetate in hexanes).

General Procedure for 3-carboxamides Formation (Compound Labeled with 6{a,b,c})

A solution of carboxylic acid (2-amino-6-ethyl-4,5,6,7-tetrahydrothieno[2,3-c]pyridine-3-carboxylic acid, (5{3,0,0} 400 mg, 1.77 mmol) dissolved in $CH_2Cl_2$ (3.6 mL) was cooled to 0° C. A solution of the appropriate alkylamine (p-tolylmethanamine, 236 mg, 1.95 mmol), and 1-(3-dimethylaminopropyl)-3-ethylcarbodiimide hydrochloride (339 mg, 1.77 mmol), 1-hydroxybenzotriazole hydrate (271 mg, 1.77 mmol), and N,N-(dimethylamino)pyridine (361 mg, 1.77 mmol) dissolved in $CH_2Cl_2$ (3.6 mL) was added. The solution was allowed to warm to room temperature and stirred for 18 h. The solution was diluted with $CH_2Cl_2$ (15.0 mL), washed with brine (20.0 mL), and dried over anhydrous $Na_2SO_4$, and concentrated to obtain a crude solid. The product was purified by flash column chromatography (methanol:$CH_2Cl_2$) to obtain a light brown product 6{3,0,3}. Yield: 40% (235.6 mg); silica gel TLC Rf=0.41 (9% methanol in DCM).

Exception Synthesis of Compound 4{3,4,3}

The product 6{3,0,3} obtained by using above general procedure was further reacted with 3,5-bis(trifluoromethyl) benzoyl chloride using general procedure for 2-amidothiophene-3-carboxylate compounds to yield product 4{3,4,3}.

6-(Tert-butyl) 3-ethyl 2-benzamido-4,7-dihydrothieno[2,3-c]pyridine-3,6(5H)-dicarboxylate (4{2,2,0})

Yield: 23% (61.5 mg); silica gel TLC Rf=0.73 (7% methanol in $CH_2C_{12}$); $^1$H-NMR (600 MHz, $CDCl_3$): δ 12.30 (s, 1H, H-10), 8.03 (m, 2H, H-22,25), 7.59 (m, 1H, H-24), 7.54 (m, 2H, H-23,25) 4.55 (s, 2H, H-8), 4.40 (q, 2H, 3J15,16 7.15 Hz, H-15), 3.68 (t, 2H, 3J6,5 5.69 Hz, H-6), 2.92 (s, 2H, H-5), 1.50 (s, 9H, H-20,29,30), 1.43 (t, 3H, 3J16,15 7.15 Hz, H-16); $^{13}$C-NMR (150 MHz, $CDCl_3$): δ 166.66 (C-2), 163.62 (C-11), 154.66 (C-17), 148.94 (C-13), 132.69 (C-24), 130.08 (C-4), 129.01 (C-25, 23), 127.50 (C-26, 22), 123.62 (C-9), 111.50 (C-3), 80.17 (C-19), 60.90 (C-15), 42.89 (C-8), 40.60 (C-6), 28.47 (C-30, 29, 20), 26.58 (C-5), 14.36 (C-16); mass spectrum (HRMS), m/z=453.1358 (M+23)+ $C_{22}H_{26}N_2NaO_5S$ requires 453.1458 (M+23)+.

6-(Tert-butyl) 3-ethyl 2-(perfluorobenzamido)-4,7-dihydrothieno[2,3-c]pyridine-3,6(5H)-dicarboxylate (4{2,3,0})

Yield: 82% (263.0 g); silica gel TLC Rf=0.89 (7% methanol in $CH_2C_{12}$); $^1$H-NMR (600 MHz, $CDCl_3$): δ 12.55 (s, 1H, H-10), 4.56 (s, 2H, H-8), 4.33 (q, 2H, 3J15,16 7.15 Hz, H-15), 3.66 (t, 2H, 3J6,5 5.5 Hz, H-6), 2.92 (t, 2H, H-5), 1.49 (s, 9H, H-30,29,20), 1.32 (t, 3H, 3J16,15 7.15 Hz, H-16); $^{13}$C-NMR (150 MHz, $CDCl_3$): δ 160.76 (C-2), 159.62 (C-11), 154.44 (C-17), 143.44 (1J24,F 251.99 Hz, C-24), 143.17 (1J26,22-F 259.69 Hz, C-26, 22), 137.65 (1J25,23,F 256.39 Hz, C-25,23), 136.94 (C-13), 135.38 (C-21), 130.72 (C-4), 125.29 (C-9), 110.67 (C-3), 80.75 (C-19), 61.86 (C-15), 42.61 (C-8), 40.05 (C-6), 28.50 (C-30, 29, 20), 26.53 (C-5) 13.87 (C-16); mass spectrum (HRMS), m/z=521.1091 (M+H)+$C_{22}H_{21}F_5N_2O_5S$ requires 521.1091 (M+H)+.

6-(Tert-butyl) 3-ethyl 2-(3,5-bis(trifluoromethyl) benzamido)-4,7-dihydrothieno[2,3-c]pyridine-3,6 (5H)-dicarboxylate (4{2,4,0})

Yield: 39% (134.0 g); silica gel TLC Rf=0.82 (7% methanol in $CH_2C_{12}$); $^1$H-NMR (600 MHz, $CDCl_3$): δ 12.56 (s, 1H, H-10), 8.45 (s, 2H, H-22, 26), 8.11 (s, 1H, H-24), 4.57 (s, 2H, H-8), 4.43 (q, 2H, 3J15,16 7.15 Hz, H-15), 3.70 (t, 2H, 3J6,5 5.69 Hz, H-6), 2.94 (t, 2H, H-5), 1.51 (s, 9H, H-30, 33, 34), 1.43 (t, 3H, 3J16,15 7.15 Hz, H-16); 13C-NMR (150 MHz, $CDCl_3$): δ 166.59 (C-2), 160.61 (C-11), 154.61 (C-17), 147.66 (C-13), 134.55 (C-21), 132.59 (C-28, 29), 127.71 (C-22,26), 126.01 (C-24), 123.70 (C-9), 121.89 (C-25,23), 112.64 (C-3), 80.28 (C-29), 61.28 (C-15), 42.67 (C-8), 40.59 (C-6), 28.46 (C-34, 33, 30), 26.54 (C-5), 14.32 (C-16); mass spectrum (HRMS), m/z=589.1216 (M+Na)+ $C_{24}H_{24}F_6N_2NaO_5S$ requires 589.1202 (M+23)+.

Ethyl 2-benzamido-6-ethyl-4,5,6,7-tetrahydrothieno [2,3-c]pyridine-3-carboxylate (4{3,2,0})

Yield: 35% (39.6 mg); silica gel TLC Rf=0.35 (10% methanol in $CH_2C_{12}$); $^1$H-NMR (600 MHz, $CDCl_3$): δ 12.27 (s, 1H, H-10), 8.01 (m, 2H, H-20,24), 7.58 (m, 1H, H-22), 7.52 (m, 2H, H-21,23), 4.39 (q, 2H, 3J17,18 7.15 Hz, H-17), 3.63 (s, 2H, H-8), 2.97 (t, 2H, 3J5,6 5.87 Hz, H-5), 2.80 (t, 3J6,5 5.63 Hz, 2H, H-6), 2.66 (q, 2H, 3J15,16 6.97 Hz, H-15), 1.40 (t, 3H, 3J18,17 7.15 Hz, H-18), 1.20 (t, 3H 3J16,15 7.34 Hz, H-16); 13C-NMR (150 MHz, CDCl$_3$): δ 166.86 (C-2), 163.63 (C-11), 148.69 (C-13), 132.69 (C-19), 132.38 (C-22), 129.75 (C-4), 129.07 (C-23,21), 127.58 (C-24,20), 124.36 (C-9), 111.58 (C-3), 60.86 (C-17), 51.69 (C-15), 51.10 (C-8), 50.24 (C-6), 26.94 (C-5), 14.46 (C-18), 12.56 (C-16); mass spectrum (HRMS), m/z=359.1418 (M+H)+. C$_{19}$H$_{23}$N$_2$O$_3$S requires 359.1424 (M+H)+.

Ethyl 6-ethyl-2-(perfluorobenzamido)-4,5,6,7-tetrahydrothieno[2,3-c]pyridine-3-carboxylate (4{3,3,0})

Yield: 16% (34.0 mg); silica gel TLC Rf=0.38 (10% methanol in CH$_2$C$_{12}$); $^1$H-NMR (600 MHz, CDCl$_3$): δ 12.02 (s, 1H, H-10), 4.36 (q, 2H, 3J17,18 7.15 Hz, H-17), 3.65 (s, 2H, H-8), 2.97 (t, 2H, H-5) 2.82 (t, 2H, H-6), 2.68 (q, 2H, 3J15,16 6.79 Hz, H-15), 1.38 (t, 3H, 3J18,17 7.15 Hz, H-18), 1.22 (t, 3H, 3J16,15 7.15 Hz, H-16); $^{13}$C-NMR (150 MHz, CDCl$_3$): δ 166.39 (C-2), 154.13 (C-11), 146.35 (C-13), 145.14 (1J22,F 256.39 Hz, C-22), 143.27 (md, 1J22,F 259.69 Hz, C-20,24), 137.99 (md, 1J22,F 255.29 Hz, C-23, 21), 130.13 (C-4), 125.47 (C-9), 112.97 (C-3), 109.77 (C-19), 81.18 (C-17), 51.65 (C-15), 50.96 (C-8), 50.10 (C-6), 26.78 (C-5), 14.37 (C-18), 12.48 (C-16); mass spectrum (HRMS), m/z=449.0971 (M+H)+C$_{19}$H$_{18}$F$_5$N$_2$O$_3$S requires 449.0953 M+H)+.

Figure 15:
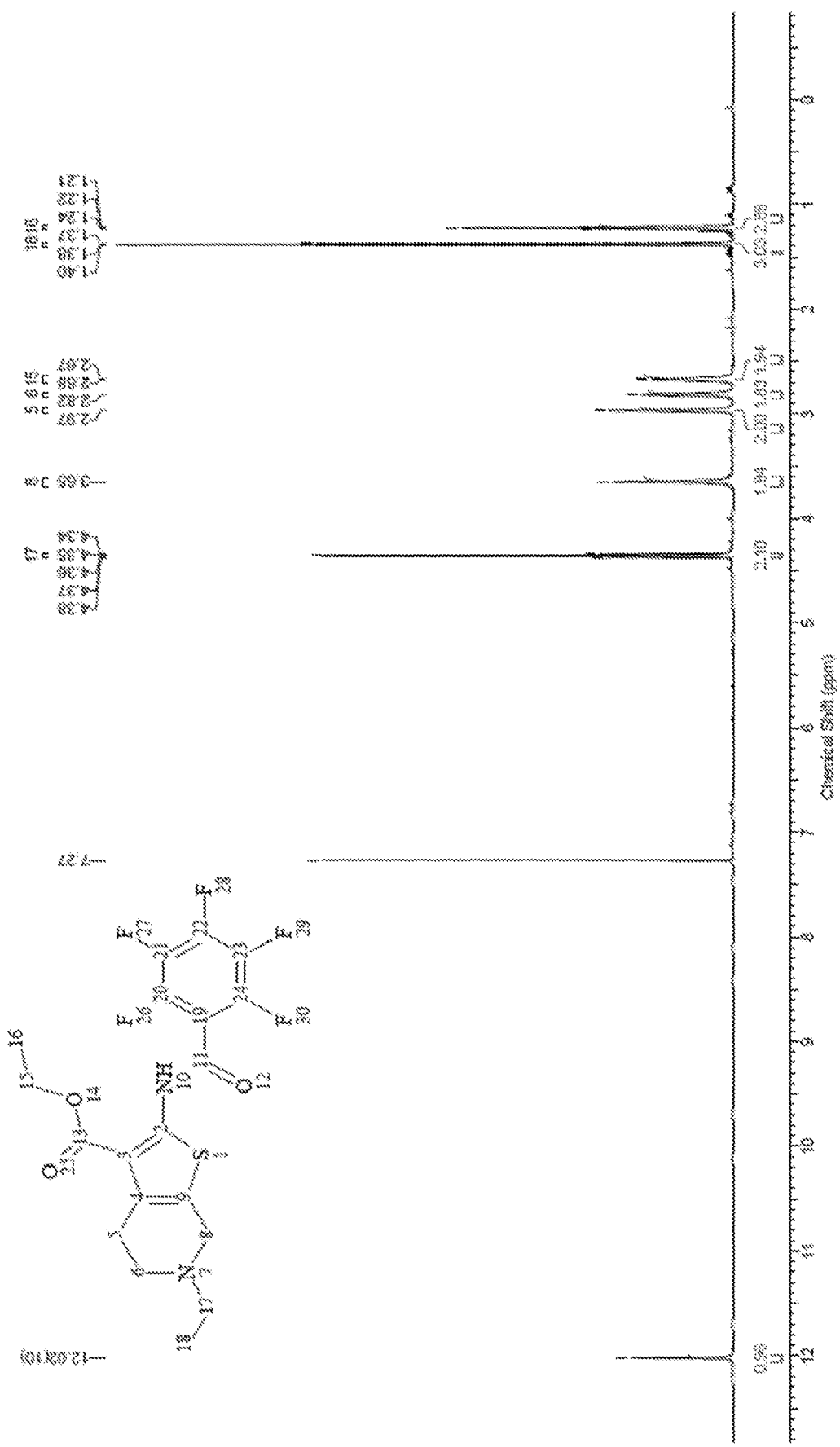
FIG. 15: $^1$H-NMR of compound ethyl 6-ethyl-2-(perfluorobenzamido)-4,5,6,7-tetrahydrothieno[2,3-c]pyridine-3-carboxylate (4{3,3,0}).
Figure 16:
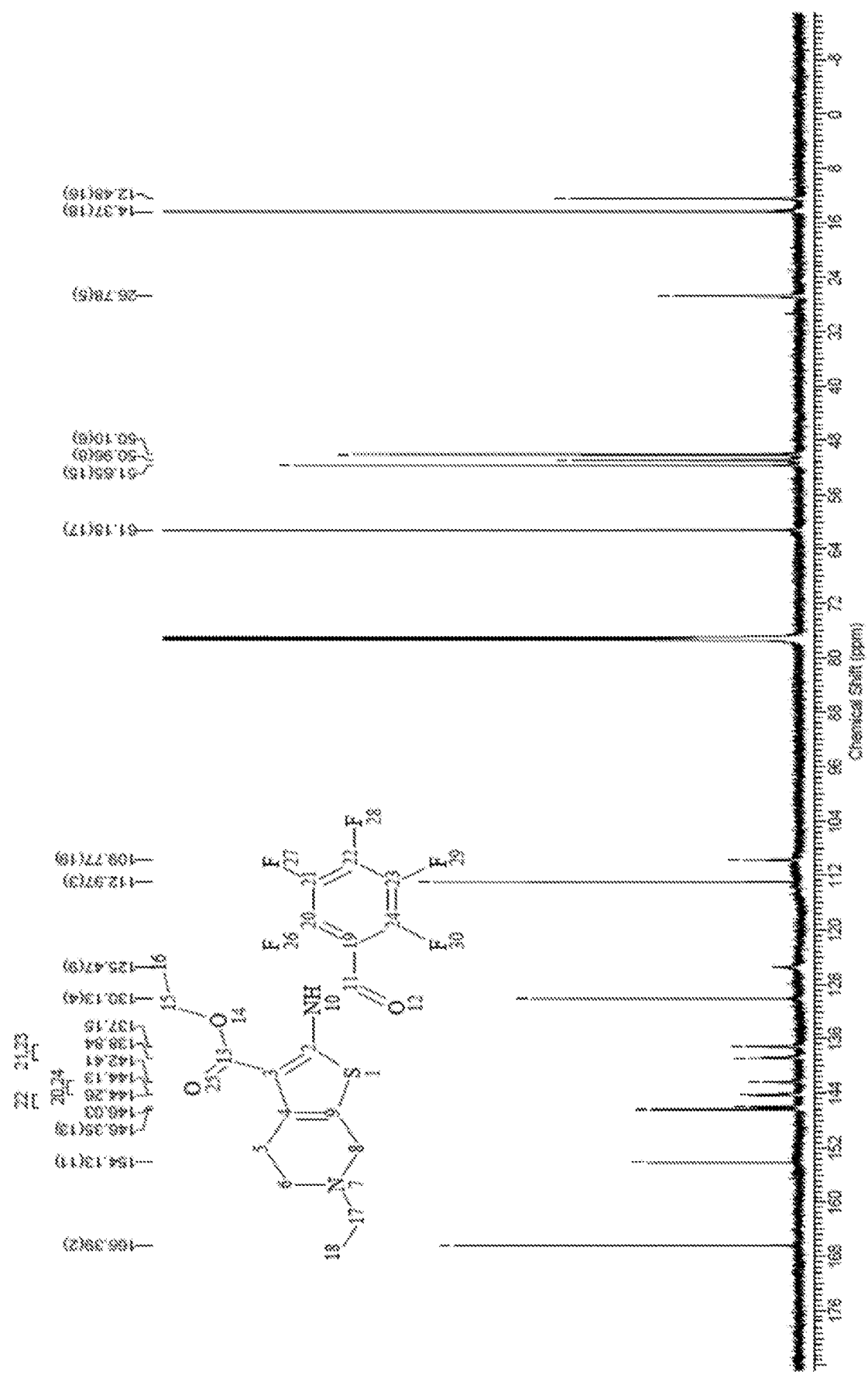
FIG. 16: $^{13}$C-NMR of compound ethyl 6-ethyl-2-(perfluorobenzamido)-4,5,6,7-tetrahydrothieno[2,3-c]pyridine-3-carboxylate (4{3,3,0}).

FIG. 15 shows the $^1$H-NMR spectrum of compound 4{3,3,0}, and FIG. 16 shows the $^{13}$C-NMR spectrum of compound 4{3,3,0}.

Ethyl 2-(3,5-bis(trifluoromethyl)benzamido)-6-ethyl-4,5,6,7-tetrahydrothieno[2,3-c]pyridine-3-carboxylate (4{3,4,0})

Yield: 43% (168.9 mg); silica gel TLC Rf=0.41 (10% methanol in CH$_2$C$_{12}$); $^1$H-NMR (600 MHz, CDCl$_3$): δ 12.53 (s, 1H, H-10), 8.45 (s, 2H, H-20, 24), 8.10 (s, 2H, H-22), 4.43 (q, 2H, 3J17,18 7.15 Hz, H-17), 3.76 (s, 2H, H-8), 3.05 (t, 2H, H-5) 2.92 (t, 2H, H-6), 2.77 (q, 2H, H-15), 1.42 (t, 3H, 3J18,17 7.15 Hz, H-18), 1.29 (t, 3H, H-16); $^{13}$C-NMR (150 MHz, CDCl$_3$): δ 166.67 (C-2), 160.73 (C-11), 147.67 (C-13), 134.69 (C-19), 132.70 (C-28, 29), 120.01 (C-4), 127.83 (C-20, 24), 126.10 (C-22), 123.83 (C-9), 122.02 (C-23, 21) 112.67 (C-3), 61.37 (C-15), 51.55 (C-15), 50.69 (C-8), 49.96 (C-6), 26.14 (C-5), 14.45 (C-18), 12.13 (C-16); mass spectrum (HRMS), m/z=517.0994 (M+H)+ C$_{21}$H$_{20}$F$_6$N$_2$O$_3$S requires 517.0991 (M+H)+.

2-(3,5-Bis(trifluoromethyl)benzamido)-6-ethyl-N-(4-methylbenzyl)-4,5,6,7-tetrahydrothieno[2,3-c]pyridine-3-carboxamide (4{3,4,3})

Yield: 22% (18.0 mg); silica gel TLC Rf=0.55 (10% methanol in CH$_2$C$_{12}$); $^1$H-NMR (600 MHz, CDCl$_3$): δ 13.65 (s, 1H, H-10), 8.47 (s, 2H, H-22,18), 8.08 (s, 1H, H-20), 7.23 (d, 2H, J33,35 6 Hz, H-33,28), 7.19 (d, 2H, J35,33 6 Hz, H-35,29), 6.23 (s, 1H, H-23), 4.63 (d, 2H, J26,23 5 Hz, H-26), 3.71 (s, 2H, H-8), 2.87 (m, 4H, H-5,6), 2.70 (q, 2H, J15,16 6 Hz, H-15), 2.36 (s, 3H, H-34), 1.23 (t, 3H, J16,15 6 Hz, H-16); $^{13}$C-NMR (150 MHz, CDCl$_3$): δ 166.20 (C-2), 160.74 (C-13), 145.91 (C-11), 136.03 (C-30), 134.67 (C-17, 27), 132.52 (C-19, 21), 129.75 (C-35, 29) 127.78 (C-22, 18), 126.13 (C-4), 125.84 (C-20), 123.90 120.29 (C-9), 114.65 (C-3), 51.74 (C-15), 51.10 (C-8), 49.93 (C-6), 43.64 (C-26), 26.96 (C-5), 21.27 (C-34), 12.35 (C-16); mass spectrum (HRMS), m/z=592.1467 (M+23)+ C$_{27}$H$_{25}$F$_6$N$_3$NaO$_2$S requires 592.1464 (M+23)+.

Ethyl 2-(perfluorobenzamido)-4,5,6,7-tetrahydrobenzo[b]thiophene-3-carboxylate (4{4,3,0})

Yield: 50.5% (188.0 mg); silica gel TLC Rf=0.86 (7% methanol in CH$_2$C$_{12}$); $^1$H-NMR (600 MHz, CDCl$_3$): δ 12.05 (s, 1H, H-10), 4.35 (q, 2H, 3J15,16 7.14 Hz, H-15), 2.80 (t, 2H, 3J8,7 6.06 Hz H-8), 2.70 (t, 2H, 3J5,6 5.94 Hz, H-5), 1.85-1.78 (m, 4H, H-6,7), 1.80 (t, 3H, 3J16,15 7.1,4 H-16); $^{13}$C-NMR (150 MHz, CDCl$_3$): δ 166.76 (C-2), 153.97 (C-11), 145.11 (md, 1J20,F 253.09 Hz, C-20), 145.81 (C-13), 143.14 (md, 1J18,22,F 259.69 Hz, C-18, 22), 137.98 (md, 1J19,21,F 254.19 Hz, C-19, 21), 131.57 (C-4), 128.43 (C-9), 113.47 (C-17), 110.10 (C-3), 61.03 (C-15), 26.48 (C-8), 24.56 (C-5), 23.04 (C-7), 22.88 (C-6), 14.39 (C-16); mass spectrum (HRMS), m/z=420.0690 (M+H)+ C$_{18}$H$_{14}$F$_5$NO$_3$S requires 420.0687 (M+H)+.

Ethyl 2-(3,5-bis(trifluoromethyl)benzaimdo)-4,5,6,7-tetrahydrobenzo[b]thiophene-3-carboxylate (4{4,4,0})

Yield: 14.5% (60.0 mg); silica gel TLC Rf=0.86 (7% methanol in CH$_2$C$_{12}$); $^1$H-NMR (600 MHz, CDCl$_3$): δ 12.58 (s, 1H, H-10), 8.44 (s, 2H, H-18,22), 8.08 (s, 1H, H-20), 4.40 (q, 2H, 3J15,16 7.14 Hz, H-15), 2.82 (t, 2H, 3J8,7 6.06 Hz, H-8), 2.71 (t, 2H, 3J5,6 5.82 Hz, H-5), 1.84-1.81 (m, 4H, H-6, 7), 1.42 (t, 3H, 3J16,15 7.14, H-16); $^{13}$C-NMR (150 MHz, CDCl$_3$): δ 167.11 (C-2), 160.52 (C-11), 146.88 (C-13), 135.03 (C-17), 132.71 (q, 2C, 1JC,F 132C-26, 27), 131.60 (C-4), 128.23 (C-9), 127.50 (d, 2C, 3JC,F 12.06C-22, 18), 125.89 (m, C-20), 123.87 (C-19), 122.06 (C-21), 113.21 (C-3), 61.10 (C-15), 26.49 (C-8), 24.60 (C-5), 23.06 (C-7), 22.88 (C-6), 14.44 (C$_{16}$); mass spectrum (HRMS), m/z=466.0833 (M+H)+C$_{20}$H$_{17}$F$_6$NO$_3$S requires 466.0906 (M+H)+.

Ethyl 2-(perfluorobenzamido)-5-phenylthiophene-3-carboxylate (4{5,3,0})

Yield: 45% (161 mg); silica gel TLC Rf=0. (30% ethyl acetate in hexanes); $^1$H-NMR (600 MHz, CDCl$_3$): δ 11.81 (s, 1H, H-6), 7.62 (dd, 2H, 3J14/18, 15/17 8.44 Hz, 3J14/18, 16 1.28 Hz, H-14, 18), 7.48 (s, 1H, H-4), 7.41 (m, 2H, H-15, 17), 7.32 (m, 1H, H-16), 4.41 (q, 2H, 3J11,12 7.15 Hz, H-11), 1.43 (t, 3H, 3J12,11 7.15 Hz, H-12); $^{13}$C-NMR (150 MHz, CDCl$_3$): δ 165.65 (C-2), 154.28 (C-7), 146.21 (C-9), 145.29 (d, 1JC,F 256.39 Hz, C-22), 143.68 (d, 1JC,F 260.79 Hz, C-24, 20), 138.05 (d, 1JC,F 255.29 Hz, C-21, 23), 135.34 (C-13), 133.45 (C-5), 129.19 (C-15, 17), 127.97 (C-16), 125.73 (C-14, 18), 119.51 (C-14), 115.59 (C-3), 109.44 (C-19), 61.10 (C-11), 14.46 (C-12); mass spectrum (HRMS), m/z=464.0352 (M+H)+ C$_{20}$H$_{12}$F$_5$NO$_3$S requires 464.0350 (M+H)+.

Ethyl 2-(3,5-bis(trifluoromethyl)benzamido)-5-phenylthiophene-3-carboxylate (4{5,4,0})

Yield: 67% (66.8 mg); silica gel TLC Rf=0. (30% ethyl acetate in hexanes); $^1$H-NMR (600 MHz, CDCl$_3$): δ 12.27 (s, 1H, H-6), 8.47 (s, 2H, H-24, 20), 8.12 (s, 2H, H-22), 7.64 (dd, 2H, 3J14/18, 15/17 8.25 Hz, 3J14/18, 16 1.28 Hz, H-14, 18), 7.50 (s, 1H, H-4), 7.42 (m, 2H, H-15, 17), 7.32 (m, 1H, H-16), 4.46 (q, 2H, 3J11,12 7.15 Hz, H-11), 1.46 (t, 3H, 3J12,11 7.15 Hz, H-12); $^{13}$C-NMR (150 MHz, CDCl$_3$): 166.06 (C-2), 160.75 (C-7), 147.32 (C-9), 135.18 (C-19), 134.55 (C-13), 133.55 (C-5), 133.22-132.54 (q, 2JC,F 34.11 Hz, C-23, 21), 129.20 (C-17, 15), 127.95 (C-16), 127.84 (3JC,F 3.30 Hz, C-24, 20), 126.21 (C-22), 125.73 (C-14, 18), 122.92 (d, 1JC,F 272.90 Hz, C-28, 29), 119.56 (C-4), 115.37 (C-3), 61.49 (C-11), 14.53 (C-12); mass spectrum (HRMS), m/z=488.0756 (M+H)+ C$_{22}$H$_{15}$F$_6$NO$_3$S requires 488.0750 (M+23)+.

2-Amino-6-((benzyloxy)carbonyl)-4,5,6,7-tetrahydrothieno[2,3-c]pyridine-3-carboxylic acid (5{1,0,0})

Yield: 69% (617.0 mg); silica gel TLC Rf=0.55 (7% methanol in CH$_2$C$_{12}$); $^1$H-NMR (600 MHz, CDCl$_3$): δ 7.37 (m, 4H, H-18, 17, 21, 20), 7.32-7.31 (m, 1H, H-19), 5.10 (s, 2H, H-15), 4.31 (m, 2H, H-8), 3.59 (s, 2H, H-6), 2.68 (s, 2H, H-5); 13C-NMR (150 MHz, CDCl$_3$): δ 166.4 (C-2), 163.51 (C-11), 154.51 (C-13), 136.86 (C-9), 130.75 (C-4), 128.43 (C-18, 20), 127.86 (C-21, 17), 127.55 (C-19), 111.56 (C-3), 42.47 (C-15), 41.13 (C-8), 40.73 (C-6), 26.77 (C-5); mass spectrum (HRMS), m/z=355.0732 (M+23)+C$_{16}$H$_{16}$N$_2$O$_4$S requires 355.0723 (M+23)+.

2-Amino-6-ethyl-4,5,6,7-tetrahydrothieno[2,3-c]pyridine-3-carboxylic acid (5{3,0,0})

The ethyl ester compound 3{3,0,0} (1.18 g, 4.64 mmol) was dissolved in 10.0 mL of THF:H$_2$O:MeOH (3:1:1) to obtain a clear solution. LiOH (0.779 g, 18.58 mmol) was added to the solution and the solution was heated to 70° C. and maintained at that temperature for 12 h. The solution was concentrated to obtain a solid. The solid was taken in Et$_2$O (20.0 mL) and the solution was subjected to sonication for 5 mins. The Et$_2$O layer was decanted and this process was repeated two times. The solid obtained was dissolved in EtOAc and the mixture was filtered to remove LiOH. The filtrate was concentrated and the solid was crystallized from methanol to a pure brownish-yellow product 5{3,0,0}. Yield: 66% (883.1 mg); silica gel TLC Rf=0.14 (10% methanol in CH$_2$C$_{12}$); $^1$H-NMR (150 MHz, DMSO-d6): δ 6.80 (s, 1H, H-10), 3.25 (s, 2H, H-8), 2.75 (m, 2H, H-6), 2.52 (m, 2H, H-5), 2.43 (q, 2H, J13,14 6 Hz, H-13), 1.03 (t, 3H, J14,13 6 Hz, H-14); $^{13}$C-NMR (150 MHz, DMSO-d$_6$): δ 171.23 (C-2), 157.27 (C-11), 133.51 (C-9), 112.59 (C-4), 111.66 (C-3), 51.86 (C-8), 51.48 (C-6), 51.05 (C-13), 28.25 (C-5), 12.95 (C-14); mass spectrum (ESI), m/z=249.07 (M+23)+ C$_{10}$H$_{14}$N$_2$O$_2$S requires 249.06 (M+23)+.

2-Amino-N-butyl-6-ethyl-4,5,6,7-tetrahydrothieno[2,3-c]pyridine-3-carboxamide (6{3,0,1})

Yield: 59% (140.0 mg); silica gel TLC Rf=0.59 (7% methanol in CH$_2$C$_{12}$); $^1$H-NMR (600 MHz, CDCl$_3$): δ 5.96 (s, 2H, H-10), 5.59 (s, 1H, H-15), 3.51 (s, 2H, H-8), 3.36 (q, 2H, H-16), 2.81 (m, 4H, H-5, 6), 2.65 (q, 2H, 3J13,14 7.14 Hz, H-13), 1.54 (quin, 2H, 3J17,16,18 7.14 Hz, H-17), 1.38 (sex, 2H, 3J18,17,19 7.5 Hz H-18), 1.20 (t, 3H, 3J14,13 7.14 Hz H-14), 0.94 (t, 3H, 3J19,18 7.5 Hz, H-19); 13C-NMR (150 MHz, CDCl3): δ 166.88 (C-2), 166.66 (C-11), 147.65 (C-13), 130.65 (C-4), 126.59 (C-9), 111.23 (C-3), 60.46 (C-15), 26.39 (C-8), 24.36 (C-5), 23.74 (C-17), 23.00 (C-7), 22.88 (C-6), 14.34 (C-16); mass spectrum (HRMS), m/z=282.1647 (M+H)+ C$_{14}$H$_{24}$N$_3$O$_3$S requires 282.1635 (M+23)+.

2-Amino-N-benzyl-6-ethyl-4,5,6,7-tetrahydrothieno[2,3-c]pyridine-3-carboxamide (6{3,0,2})

Yield: 59% (140.0 mg); silica gel TLC Rf=0.57 (7% methanol in CH$_2$C$_{12}$); $^1$H-NMR (600 MHz, CDCl$_3$): δ 7.36-7.28 (m, 5H, H-18, 19, 20, 21, 22), 6.04 (s, 2H, H-10), 5.91 (s, 1H, H-15), 4.59 (d, 2H, 3J16,15 5.58 Hz, H-16), 3.46 (s, 2H, H-8), 2.74 (s, 4H, H-6, 5), 2.58 (q, 2H, 3J13,14 7.14, H-13), 1.16 (t, 3H, 3J14,13 7.14, H-14); 13C-NMR (150 MHz, CDCl$_3$): δ 166.26 (C-2), 159.70 (C-11), 138.69 (C-9), 128.76 (C-21, 19), 127.45 (C-18, 20, 22, 4), 116.34 (C-17), 108.52 (C-3), 51.56 (C-16), 51.27 (C-8), 50.08 (C-6), 43.20 (C-13), 27.73 (C-5), 12.58 (C-14); mass spectrum (HRMS), m/z=316.1486 (M+H)+C$_{17}$H$_{21}$N$_3$OS requires 316.1478 (M+23)+.

2-Amino-6-ethyl-N-(4-methylbenzyl)-4,5,6,7-tetrahydrothieno[2,3-c]pyridine-3-carboxamide (6{3,0,3})

Yield: 40% (235.6 mg); silica gel TLC Rf=0.55 (7% methanol in CH$_2$C$_{12}$); $^1$H-NMR (600 MHz, CDCl$_3$): 0.20 (m, 2H, H-21,19), 7.16 (m, 2H, H-22,18), 6.03 (s, 2H, H-10), 5.87 (s, 1H, H-15), 4.53 (d, 2H, J16,15 6 Hz, H-16), 3.50 (s, 2H, H8), 2.75 (m, 4H, H-5,6), 2.61 (q, 2H, J13,14 6 Hz H-13), 2.35 (s, 3H, H-23), 1.17 (t, 2H, J14,13 6 Hz H-14); 13C-NMR (150 MHz, CDCl$_3$): δ166.19 (C-11), 159.63 (C-2), 137.08 (C-20, 9), 135.57 (C-17), 129.43 (C-21, 19), 127.49 (C-22, 18), 116.01 (C-4), 51.52 (C-8), 51.17 (C-6), 50.02 (C-13), 43.03 (C-16), 27.54 (C-23), 21.13 (C-5), 12.47 (C-14); mass spectrum (HRMS), m/z=352.1460 (M+23)+ C$_{18}$H$_{23}$N$_3$OS requires 352.1460 (M+23)+.

2-Amino-6-ethyl-N-(2-methoxybenzyl)-4,5,6,7-tetrahydrothieno[2,3-c]pyridine-3-carboxamide (6{3,0,4})

Yield: 59% (140.0 mg); silica gel TLC Rf=0.55 (10% methanol in CH$_2$C$_{12}$); $^1$H-NMR (600 MHz, CDCl$_3$): δ 7.30-7.25 (m, 2H, H-20, 19), 6.92 (t, 1H, 3J21,20 7.44 Hz, H-21), 6.87 (d, 1H, 3J22,21 8.22H-22), 6.29 (s, 1H, H-15), 6.01 (s, 2H, H-10), 4.54 (d, 2H, 3J16,15 5.88 Hz, H-16), 3.87 (s, 3H, H-24), 3.47 (s, 2H, H-8), 2.76 (s, 4H, H-6, 5), 2.61 (q, 2H, 3J13,14 7.14 Hz, H-13), 1.18 (t, 3H, 3J14,13 7.14 Hz, H-14); $^{13}$C-NMR (150 MHz, CDCl$_3$): δ 165.96 (C-2), 159.32 (C-11), 157.55 (C-13), 129.66 (C-4), 128.76 (C-9), 127.60 (C-22), 126.66 (C-20), 120.76 (C-21), 110.20 (C-3), 108.52 (C-19), 55.28 (C-24), 51.59 (C-16), 51.07 (C-8), 50.20 (C-6), 39.34 (C-13), 27.54 (C-5), 12.38 (C-14); mass spectrum (HRMS), m/z=346.1587 (M+H)+ C$_{18}$H$_{24}$N$_3$O$_2$S requires 346.1584 (M+H)+.

N-(Adamantan-1-yl)-2-amino-6-ethyl-4,5,6,7-tetrahydrothieno[2,3-c]pyridine-3-carboxamide (6{3,0,5})

Yield: 59% (140.0 mg); silica gel TLC Rf=0.7 (10% methanol in CH$_2$C$_{12}$); $^1$H-NMR (600 MHz, CDCl$_3$): δ 5.84 (s, 2H, H-10), 5.37 (s, 1H, H-15), 3.50 (s, 2H, H-8), 2.78 (d, 2H, 3J6,5 4.8 Hz, H-6), 2.75 (d, 2H, 3J5,6 4.8 Hz, H-5), 2.63 (q, 2H, 3J13,14 7.14 Hz, H-13), 2.09-2.06 (m, 10H, H-17, 22, 21, 18, 23, 20), 1.70-1.68 (m, 5H, H-19, 24, 25), 1.86 (t, 3H, 3J14,13 7.14H-14); $^{13}$C-NMR (150 MHz, CDCl$_3$): 165.61 (C-2), 158.42 (C-11), 127.51 (C-4), 115.70 (C-9), 109.95 (C-3), 51.99 (C-13), 51.50 (C-8), 51.09 (C-6), 50.08 (C-16), 42.18 (C-17, 21, 22), 36.43 (C-19, 24, 25), 29.49

2-Amino-N-butyl-4,5,6,7-tetrahydrobenzo[b]thiophene-3-carboxamide (6{4,0,1})

Yield: 16.13% (45.0 mg); silica gel TLC Rf=0.45 (30% ethyl acetate in hexanes); $^1$H-NMR (600 MHz, CDCl$_3$): δ 5.66 (s, 1H, H-13), 3.36 (m, 2H, H-14), 2.60 (m, 2H, H-8), 2.53 (m, 2H, H-5), 1.80 (m, 4H, H-6,7), 1.54 (m, 2H, H-15), 1.38 (sex, 2H, 3J16,17 7.38 Hz, H-16), 0.94 (t, 3H, 3J17,16 7.38H-17); 13C-NMR (150 MHz, CDCl$_3$): δ 166.53 (C-2), 158.53 (C-11), 128.80 (C-9), 118.90 (C-4), 108.9 (C-3), 38.92 (C-14), 31.88 (C-15), 27.18 (C-8), 24.53 (C-5), 22.99 (C-7), 22.90 (C-6), 20.29 (C-16), 13.81 (C-17); mass spectrum (HRMS), m/z=275.1194 (M+23)+ C$_{13}$H$_{20}$N$_2$OS requires 275.1194 (M+23)+.

2-Amino-N-(4-methylbenzyl)-4,5,6,7-tetrahydrobenzo[b]thiophene-3-carboxamide (6{4,0,3})

Yield: 25% (83.0 mg); silica gel TLC Rf=0.46 (7% methanol in CH$_2$C$_{12}$); $^1$H-NMR (600 MHz, CDCl$_3$): δ 7.22 (d, 2H, 3J17,16 7.98 Hz, H-17, 19), 7.15 (d, 2H, 3J16,17 7.86 Hz, H-16, 20), 5.95 (s, 1H, H-13), 4.54 (d, 2H, 3J14,13 5.46 Hz, H-14), 2.58 (m, 2H, H-8), 2.54 (m, 2H, H-5), 2.34 (s, 3H, H-21), 1.77 (m, 4H, H-6, 7); $^{13}$C-NMR (150 MHz, CDCl$_3$): δ166.38 (C-2), 158.62 (C-11), 137.03 (C-9), 135.65 (C-18), 129.40 (C-19, 17), 128.82 (C-5), 127.56 (C-16, 20), 119.21 (C-4), 108.90 (C-3), 43.04 (C-14), 27.21 (C-8), 24.55 (C-5), 22.92 (C-7), 22.85 (C-6), 21.12 (C-21); mass spectrum (HRMS), m/z=301.1377 (M+H)+ C$_{17}$H$_{21}$N$_2$OS requires 301.1369 (M+H)+.

2-Amino-N-(2-methoxybenzyl)-4,5,6,7-tetrahydrobenzo[b]thiophene-3-carboxamide (6{4,0,4})

Yield: 12% (40.0 mg); silica gel TLC Rf=0.35 (30% ethyl acetate-hexanes); $^1$H-NMR (600 MHz, CDCl$_3$): δ 7.31-7.25 (m, 2H, H-17,20), 6.94-6.88 (m, 2H, H-19,18), 6.36 (s, 1H, H-13), 4.55 (d, 2H, 3J14,13 5.58 Hz, H-14), 3.88 (s, 3H, H-22), 2.60 (m, 2H, H-5), 2.53 (m, 2H, H-8), 1.79 (m, 4H, H-6,7); $^{13}$C-NMR (150 MHz, CDCl$_3$): δ 166.19 (C-2), 158.75 (C-11), 157.53 (C-16), 129.67 (C-9), 128.95 (C-20), 128.71 (C-18), 126.75 (C-15), 120.77 (C-4), 118.73 (C-19), 110.17 (C-17), 108.92 (C-3), 55.20 (C-22), 39.25 (C-14), 27.01 (C-8), 24.54 (C-5), 23.04 (C-7), 22.92 (C-6); mass spectrum (HRMS), m/z=317.1316 (M+H)+ C$_{17}$H$_{21}$N$_2$O$_2$S requires 317.1316 (M+H)+.

N-(Adamantan-1-yl)-2-amino-4,5,6,7-tetrahydrobenzo[b]thiophene-3-carboxamide (6{4,0,5})

Yield: 13% (45.0 mg); silica gel TLC Rf=0.53 (30% ethyl acetate-hexanes); $^1$H-NMR (600 MHz, CDCl$_3$): δ 5.43 (s, 1H, H-13), 2.58 (m, 2H, H-8), 2.53 (m, 2H, H-5), 2.05 (m, 9H, H-15, 16, 18, 19, 20, 21), 1.78 (m, 4H, H-6, 7), 1.70 (m, 6H, H-17, 22, 23); $^{13}$C-NMR (150 MHz, CDCl$_3$): δ 165.89 (C-2), 157.87 (C-11), 128.84 (C-9), 118.95 (C-4), 110.31 (C-3), 51.94 (C-14), 42.19 (C-15, 19, 20), 36.47 (17, 23, 22), 29.52 (C-16, 18, 21), 27.32 (C-8), 24.57 (C-5), 23.09 (C-7), 22.94 (C-6); mass spectrum (HRMS), m/z=331.1843 (M+H)+ C$_{19}$H$_{27}$N$_2$OS requires 331.1839 (M+23)+.

2-Amino-N-benzyl-5-phenylthiophene-3-carboxamide (6{5,0,2})

Yield: 59% (166.4 mg); silica gel TLC Rf=0.33 (30% ethyl acetate in hexanes); $^1$H-NMR (600 MHz, CDCl$_3$): δ 7.41 (dd, 2H, 3J10/14, 11/13 8.25 Hz, 3J10/14, 12 1.28 Hz, H-10, 14), 7.37 (m, 4H, H-21, 19, 22, 18), 7.32 (m, 3H, H-12, 11, 13), 7.21 (m, 1H, H-20), 6.95 (s, 1H, H-4), 6.04 (s, 1H, H-15), 4.60 (d, 2H, 3J16,15NH 5.69 Hz, H-16); $^{13}$C-NMR (150 MHz, CDCl$_3$): δ 165.73 (C-2), 160.65 (C-7), 138.68 (C-5), 133.99 (C-17), 128.99 (C-11, 13), 128.90 (C-21, 19), 127.97 (C-10, 14), 127.66 (C-12), 126.81 (C-20), 124.79 (C-22, 18), 118.08 (C-4), 109.56 (C-3), 43.42 (C-16); mass spectrum (HRMS), m/z=331.0876 (M+23)+ C$_{18}$H$_{16}$N$_2$OS requires 331.0876 (M+23)+.

2-Amino-N-(4-methylbenzyl)-5-phenylthiophene-3-carboxamide (6{5,0,3})

Yield: 57% (167 mg); silica gel TLC Rf=0.35 (30% ethyl acetate in hexanes); $^1$H-NMR (600 MHz, CDCl$_3$): δ 7.41 (dd, 2H, 3J10/14, 11/13 8.44 Hz, 3J10/14, 12 1.10 Hz, H-10, 14), 7.32 (m, 2H, H-11, 13), 7.27 (d, 2H, H-22, 18), 7.22 (m, 1H, H-12), 7.19 (d, 2H, H-19, 21), 6.92 (s, 1H, H-4), 2.36 (s, 3H, H-23); $^{13}$C-NMR (150 MHz, CDCl$_3$): δ165.55 (C-7), 160.45 (C-2), 137.31 (C-5), 135.47 (C-20), 133.89 (C-17), 129.46 (C-11, 13), 128.87 (C-21, 19), 127.92 (C-9), 125.40 (C-12), 124.66 (C-10, 14), 117.94 (C-4), 117.94 (C-4), 109.51 (C-3) 43.11 (C-16), 21.14 (C-23); mass spectrum (HRMS), m/z=323.1213 (M+H)+C$_{19}$H$_{18}$N$_2$OS requires 323.1227 (M+23)+.

2-Amino-N-(2-methoxybenzyl)-5-phenylthiophene-3-carboxamide (6{5,0,4})

Yield: 68% (210.9 mg); silica gel TLC Rf=0.3 (30% ethyl acetate in hexanes); $^1$H-NMR (600 MHz, CDCl$_3$): δ 7.41 (dd, 2H, 3J10/14, 11/13 8.44 Hz, 3J10/14, 12 1.10 Hz, H-10, 14), 7.35-7.31 (m, 3H, H-11, 12, 13), 7.29 (m, 1H, H-18), 7.21 (m, 1H, H-19), 6.97-6.94 (m, 2H, H-20, 4), 6.92 (d, 1H, 3J21,20 8.25 Hz, H-21), 6.29 (s, 1H, H-15), 4.59 (d, 2H, 3J16,15NH 2.75 Hz, H-16), 3.90 (s, 3H, H-23); $^{13}$C-NMR (150 MHz, CDCl$_3$): δ 165.53 (C-7), 157.73 (C-2), 133.99 (C-22), 129.88 (C-9), 129.02 (C-5), 128.99 (C-11, 13), 126.89 (C-12), 126.48 (C-17, 19), 124.88 (C-10, 14), 120.88 (C-18, 20) 118.21 (C-4), 111.13 (C-21) 110.54 (C-3), 55.56 (C-16), 39.24 (C-23); mass spectrum (HRMS), m/z=339.1159 (M+H)+C$_{19}$H$_{18}$N$_2$O$_2$S requires 339.1162 (M+H)+.

N-(adamantan-1-yl)-2-amino-5-phenylthiophene-3-carboxamide (6{5,0,5})

Yield: 44% (140.4 mg); silica gel TLC Rf=0.62 (30% ethyl acetate in hexanes); $^1$H-NMR (600 MHz, CDCl$_3$): δ 7.44 (dd, 2H, 1/10/14, 11/13 8.44 Hz, 3J10/14, 12 1.28 Hz, H-10, 14), 7.33 (m, 3H, H-13, 11), 7.22 (m, 1H, H-12), 6.90 (s, 1H, H-4), 2.16 (s, 9H, H-23, 20, 21, 18, 17, 22), 1.76 (m, 6H, H-25, 19, 24); $^{13}$C-NMR (150 MHz, CDCl$_3$): δ165.44 (C-7), 158.84 (C-2), 134.07 (C-5), 128.97 (C-11, 13), 126.81 (C-12), 125.82 (C-9), 124.85 (C-10, 14), 118.39 (C-4), 111.64 (C-3), 52.27 (C-16), 42.16 (C-20, 1, 22, 17), 36.53 (C-25, 19, 24), 29.65 (18, 23); mass spectrum (HRMS), m/z=353.1697 (M+H)+ C$_{21}$H$_{25}$N$_2$OS requires 353.1682 (M+H)+.

In Vitro Mtb Alamar Blue Assay (MABA)

Mtb H37Rv is a drug sensitive laboratory reference strain used in the MIC studies. The bacteria were grown at 37° C. in Difco™ 7H9 Middlebrook liquid media (BD Biosciences, 271310) supplemented with 10% Middlebrook OADC Enrichment, 0.05% Tween (G-Biosciences, 786-519), and 0.2% Glycerol. A modified 96-well microplate Alamar Blue assay (MABA) was used to establish MIC values. Briefly, compounds were solubilized in DMSO and were two-fold serially diluted in 7H9 media. Bacteria were grown to mid-log growth, diluted and added to the wells with compounds. Cell and media controls were included in each plate. The plates were incubated at 37° for 6 days when Alamar blue was added to each well and then the plate was incubated overnight. On day seven, the last well that showed no sign of growth and remained blue was considered the MIC for that compound. Standard calculations were used to calculate the $IC_{50}$ for the compounds.

In Vitro Dual Readout MIC Assay

The MIC of compound was determined by measuring bacterial growth after 5 d in the presence of test compounds. Compounds were prepared as 10-point two-fold serial dilutions in DMSO and diluted into 7H9-Tw-OADC medium in 96-well plates with a final DMSO concentration of 2%. The highest concentration of compound was 200 µM where compounds were soluble in DMSO at 10 mM. Each plate included assay controls for background (medium/DMSO only, no bacterial cells), zero growth (100 µM rifampicin), and maximum growth (DMSO only), as well as a rifampicin dose response curve. Plates were inoculated with *M. tuberculosis* and incubated for 5 days; growth was measured by $OD_{590}$. To calculate the MIC, the 10-point dose response curve was plotted as % growth and fitted to the Gompertz model using GraphPad Prism 5. The MIC was defined as the minimum concentration at which growth was completely inhibited and was calculated from the inflection point of the fitted curve to the lower asymptote (zero growth). In addition, dose response curves were generated using the Levenberg-Marquardt algorithm, and the concentrations that resulted in 50% and 90% inhibition of growth were determined ($IC_{50}$ and $IC_{90}$, respectively)

Minimum Bactericidal Concentration (MBC)

Mtb was grown aerobically to logarithmic phase and inoculated into liquid 7H9-Tw-OADC medium containing four different compound concentrations with a final maximum concentration of 2% DMSO. Compounds were tested at fixed concentrations, as no MIC data were available at the time. (200 100, 20, and 5 µM). Cultures were exposed to compounds for 21 days and cell viability measured by enumerating colony forming units on agar plates on day 0, 7, 14, and 21. MBC was defined as the minimum concentration required to achieve a 2-log kill in 21 days. For compounds with >1-log kill, an assessment of time- and/or concentration-dependence was determined from the kill kinetics. DMSO was used as a positive control for growth.

Intracellular Activity and Cytotoxicity

The cytotoxicity of compounds was determined by measuring THP-1 cell viability after 3 days in the presence of test compounds. Compounds were prepared as 10-point three-fold serial dilutions in DMSO. The highest concentration of compound tested was 50 µM where compounds were soluble in DMSO at 10 mM. THP-1 cells were cultured in complete RPMI and differentiated into macrophage-like cells using 80 nM PMA overnight at 37° C., 5% $CO_2$. Cells were inoculated into assay plates and cultured for 24 h before compound dilutions were added to a final DMSO concentration of 0.5%. Each run included staurosporine as a control. Assay plates were incubated for 3 days at 37° C., 5% $CO_2$; growth was measured using the CellTiter-Glo® Luminescent Cell Viability Assay (Promega) which uses ATP as an indicator of cell viability. Relative luminescent units (RLU) were measured using a Biotek Synergy 4 plate reader. The dose response curve was fitted using the Levenberg-Marquardt algorithm. The $IC_{50}$ was defined as the compound concentration that produced 50% inhibition of growth.

The activity of compounds against intracellular bacteria was determined by measuring viability in infected THP-1 cell after 3 days in the presence of test compounds. Compounds were prepared as 10-point three-fold serial dilutions in DMSO. The highest concentration of compound tested was 50 µM where compounds were soluble in DMSO at 10 mM. THP-1 cells were cultured in RPMI 1640 complete medium and differentiated into macrophagelike cells using 80 nM PMA overnight at 37° C., 5% $CO_2$. THP-1 cells were infected with a luminescent strain of H37Rv (which constitutively expresses luxABCDE) at a multiplicity of infection of 1 and incubated overnight at 37° C., 5% $CO_2$. Infected cells were recovered using Accutase/EDTA solution, washed twice with PBS to remove extracellular bacteria and seeded into assay pates. Compound dilutions were added to a final DMSO concentration of 0.5%. Assay plates were incubated for 72 h at 37° C., 5% $CO_2$. Each run included isoniazid as a control.

Relative luminescent units (RLU) were measured using a Biotek Synergy 2 plate reader. The dose response curve was fitted using the Levenberg-Marquardt algorithm. The $IC_{50}$ and $IC_{90}$ were defined as the compound concentrations that produced 50% and 90% inhibition of growth respectively.

Effect of 4{3,3,0} on Lipid Synthesis

Mtb H37Rv mc26206 grown in 7H9-OADC-0.05% Tyloxapol supplemented with 0.2% casaminoacid, 48 µg/mL pantothenate and 50 µg/mL L-leucine (OD600=0.5) was treated with either no drug (control) or 0.4 µg/ml 4{3,3,0}, 1 µg/ml 4{3,3,0}, 2 µg/ml 4{3,3,0}, or 4 µg/ml 4{3,3,0} for 16 h. [1,2-14C]-acetate was addded to the culture at the same time as the inhibitor. Total lipids were extracted from bacterial cells, and mycolic acid methyl esters (MAMEs) and fatty acid methyl esters (FAMEs) were prepared. Total lipids, FAMEs, and MAMEs were analyzed by TLC and revealed by autoradiography. The MIC of 4{3,3,0} against Mtb H37Rv mc26206 grown in 7H9-OADC-Tyloxapol medium was determined as 0.4 µg/ml (visual scanning for growth).

Comparison of 4{3,3,0} and a Selenylamide

Compound 4{3,3,0} was evaluated in comparison to a selenylamide (structure shown in FIG. 10A). FIG. 10A is a summary of MIC under aerobic conditions for compound 4{3,3,0} and the selenylamide. The antimicrobial activity of the compounds against Mtb H37Rv grown under aerobic conditions was assessed by determining the MIC as described above. The MIC data in FIG. 10A was obtained following the in vitro dual readout MIC assay protocol described above, using 20-point two-fold serial dilutions.

To determine the MIC under low oxygen, the antimicrobial activity of compounds against MTb H37Rv grown under hypoxic conditions was assessed using the low oxygen recovery assay (LORA). Bacteria were first adapted to low oxygen conditions and then exposed to compounds under hypoxia; this was followed by a period of outgrowth in aerobic conditions and growth is measured using luminescence.

Although the MICs of the two chemotypes exhibit modest activity against Mtb under low oxygen growth conditions, the results are a validation of the cell wall biosynthesis targets. It has been shown that both Isoniazid and Ethambutol show a significant MICs decreases (>128 µM) against Mtb during low oxygen growth.

To determine the minimum bactericidal concentration, test compounds were prepared as 20-point two-fold serial dilutions in DMSO and diluted into DTA medium in 96-well plates with a final DMSO concentration of 2%. The highest concentration of compound was 200 µM, where compounds were soluble in DMSO at 10 mM. Control compounds were prepared as two-fold serial dilutions in DMSO and diluted into DTA medium in 96-well plates with a final DMSO concentration of 2%.

Mtb constitutively expressing the luxABCDE operon was inoculated into DTA medium in gas-impermeable glass tubes and incubated for 18 days to generate hypoxic conditions (Wayne model of hypoxia). At this point, bacteria were in a nonreplicating state (NRP stage 2) induced by oxygen depletion. Oxygen-deprived bacteria were inoculated into compound assay plates and incubated under anaerobic conditions for 10 days followed by incubation under aerobic conditions (outgrowth) for 28 h. Growth was measured by luminescence.

Oxygen-deprived bacteria were also inoculated into compound assay plates and incubated under aerobic conditions for 5 days. Growth was measured by luminescence. Rifampicin was included in each plate and metronidazole was included in each run as positive controls for aerobic and anaerobic killing of Mtb, respectively.

Figure 10B:
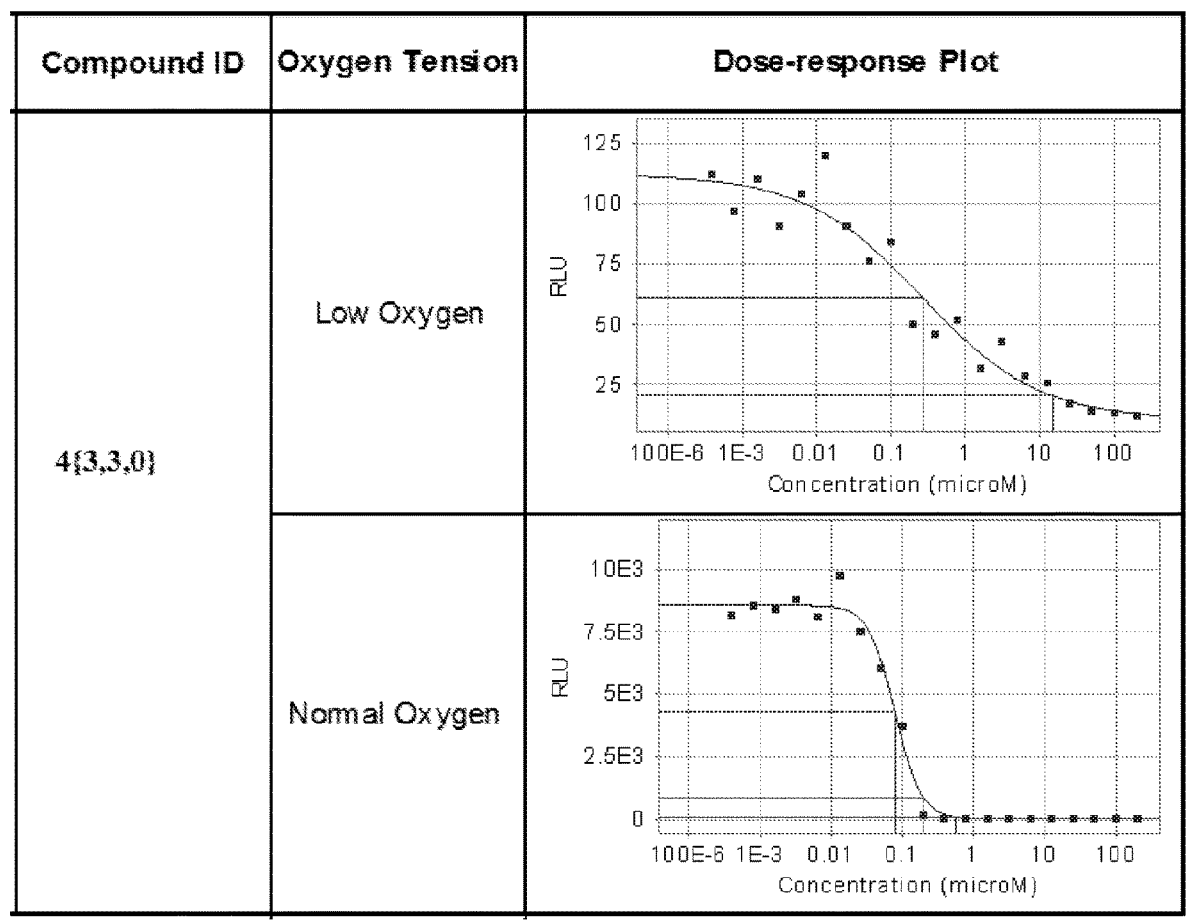
Figure 10C:
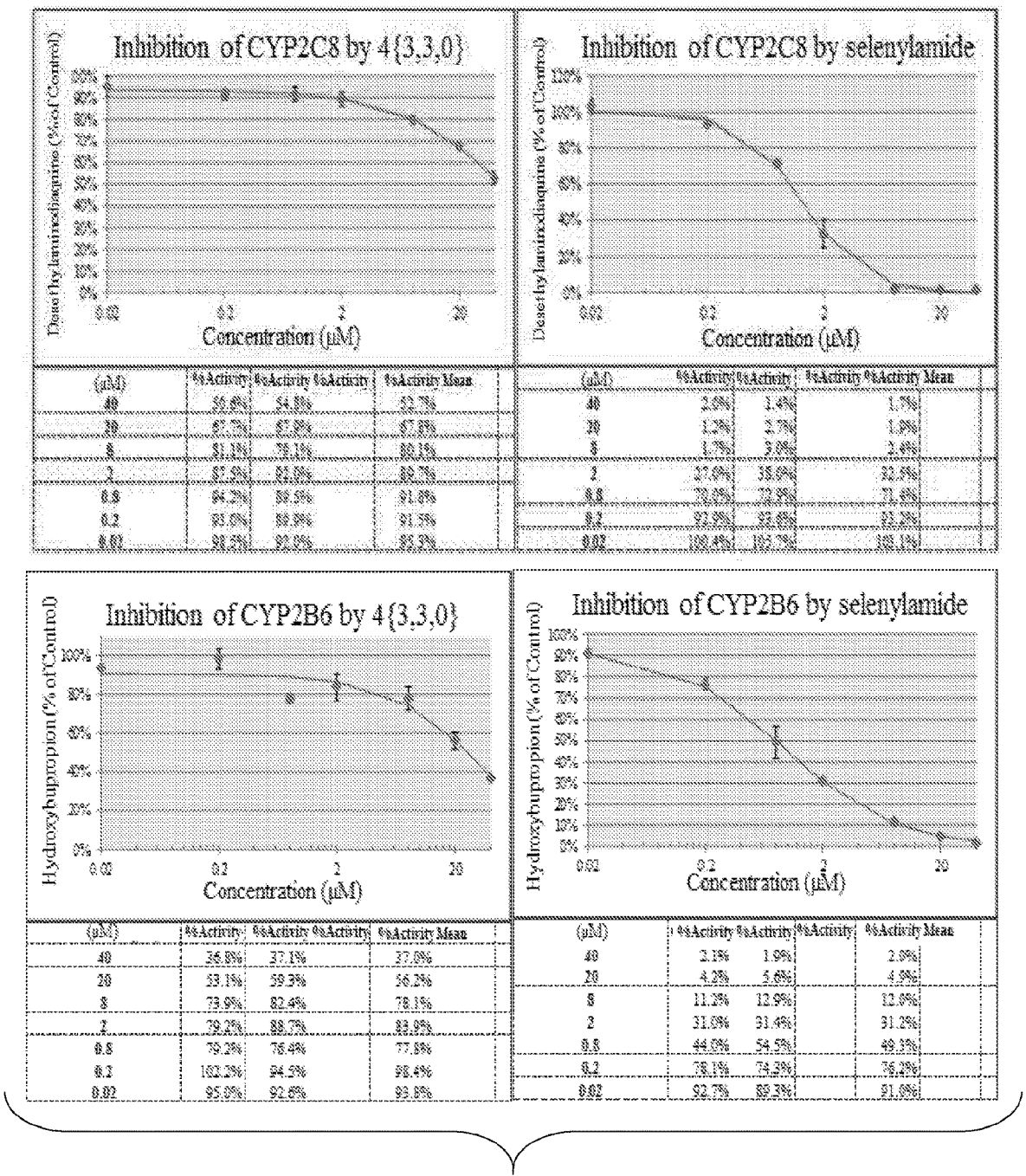
Figure 10D:
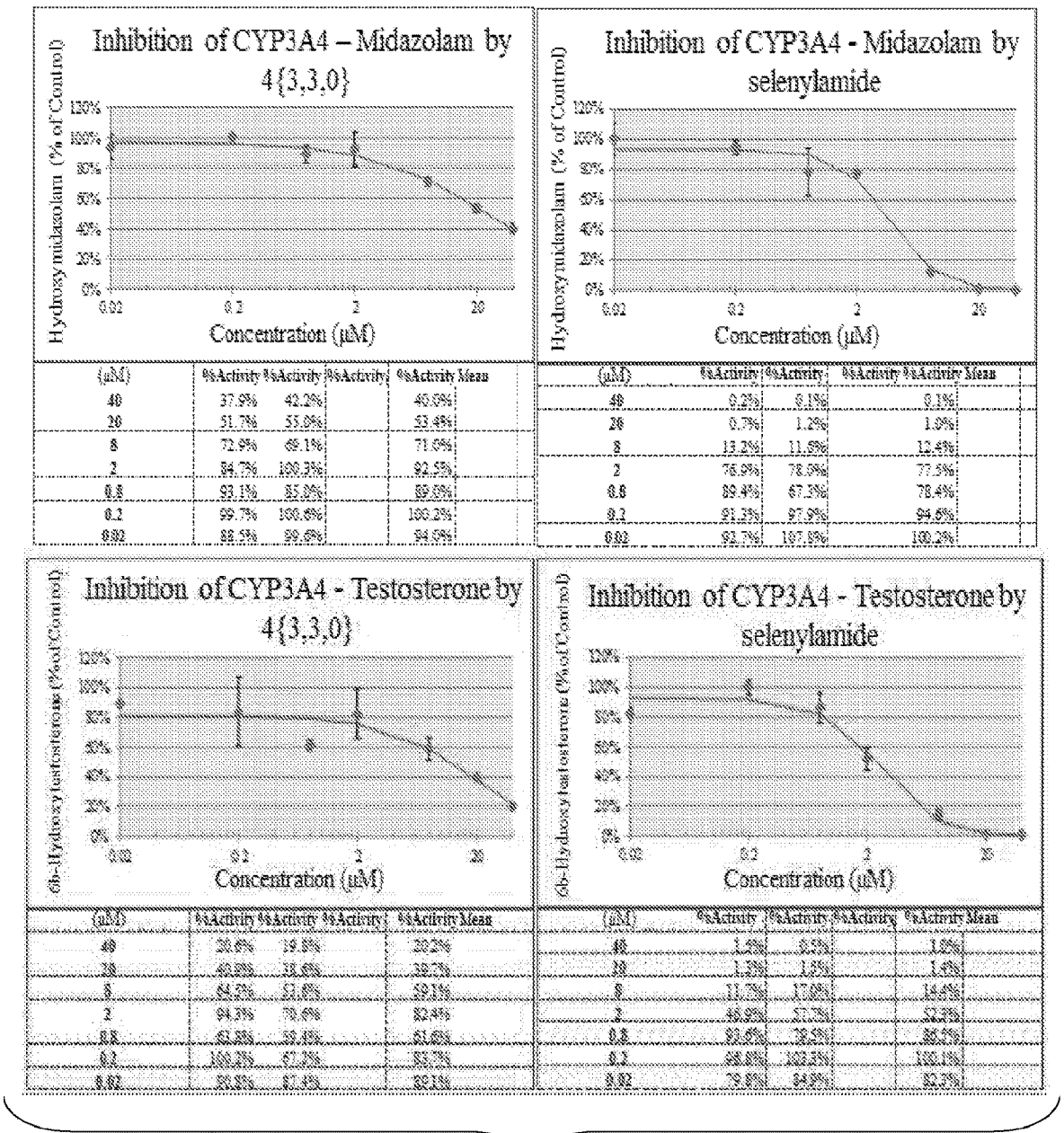
Figure 10E:
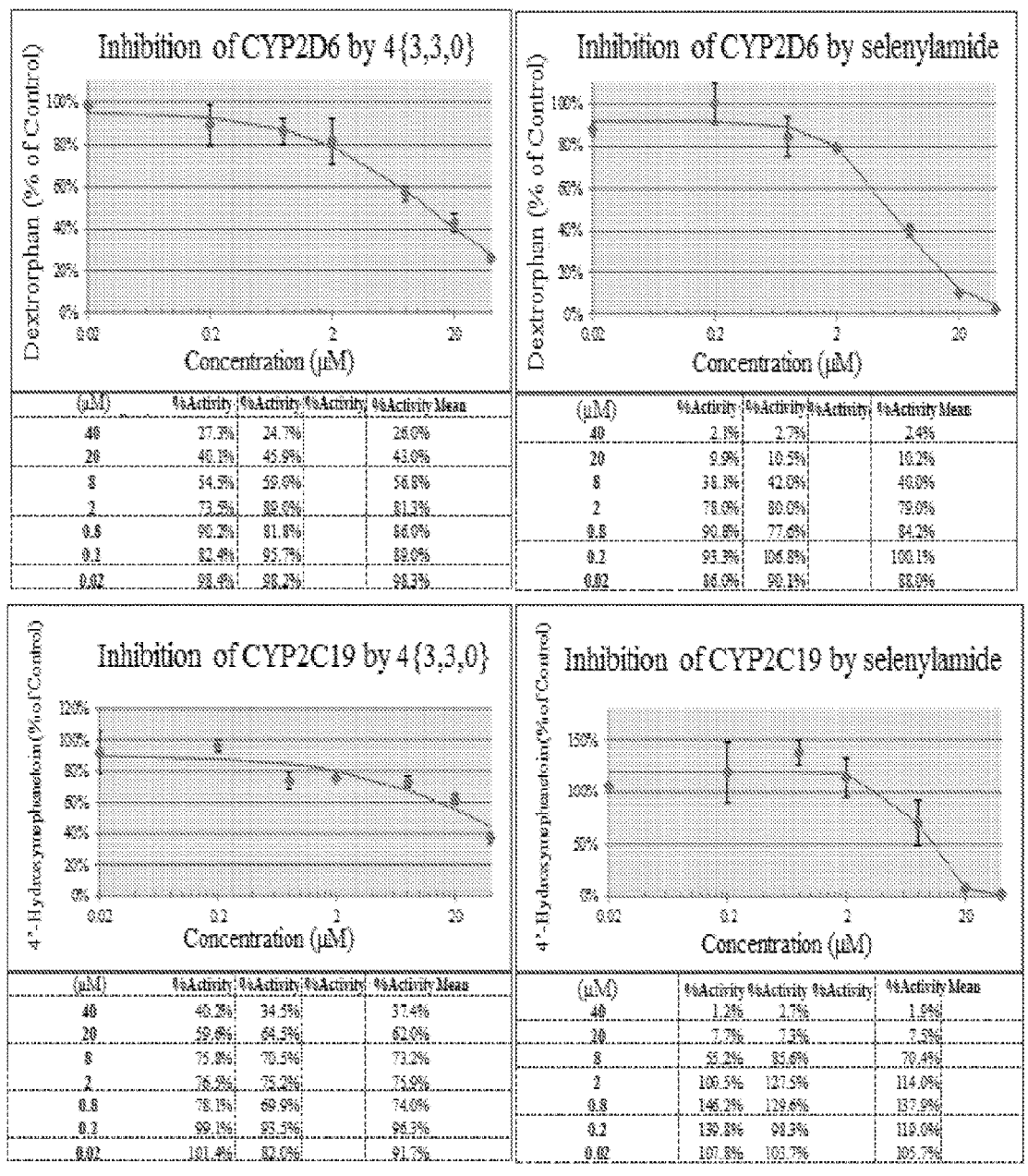
Figure 10F:
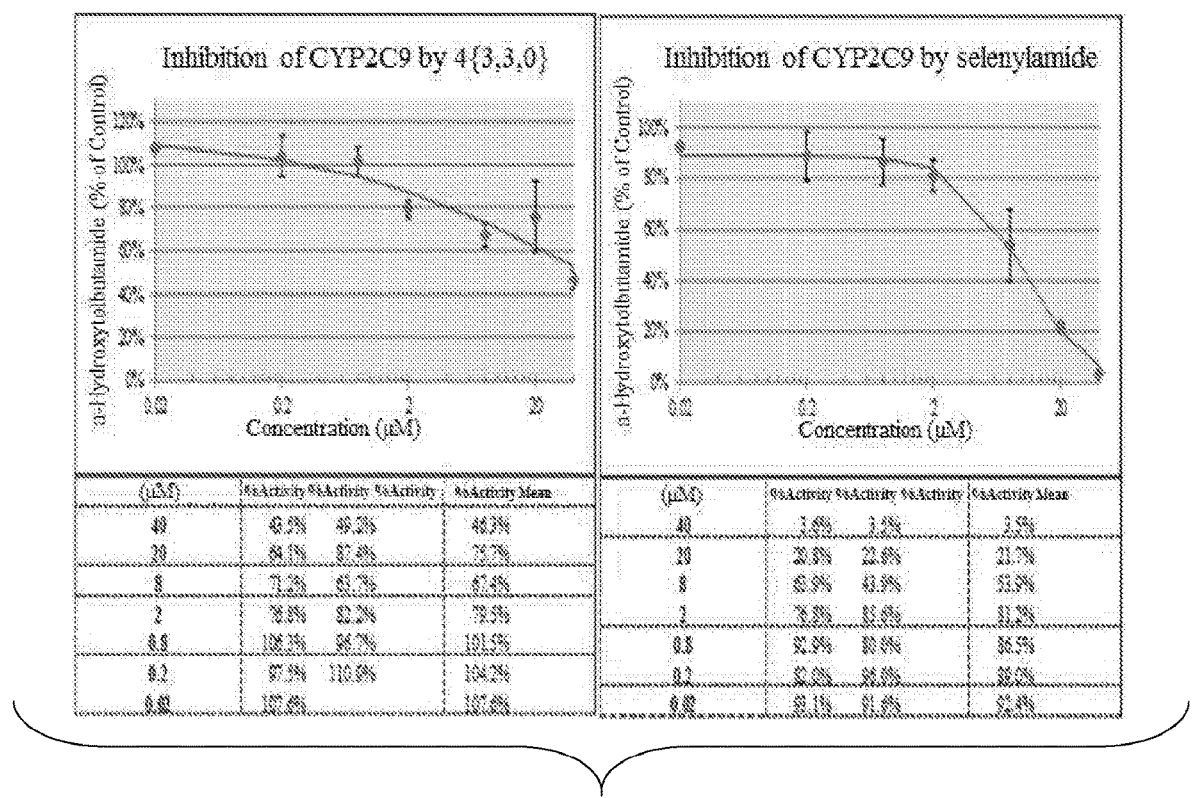

The bactericidal activity of compounds was assessed against Mtb H37Rv grown in aerobic conditions in 7H9-Tw-OADC medium. Viable cell counts were measured over 3 weeks of exposure to determine the rate of kill. Mtb was grown aerobically to logarithmic phase and inoculated into liquid medium containing four different compound concentrations with a final maximum concentration of 2% DMSO. Compounds were tested at fixed concentrations, as no MIC data were available (200, 100, 20, and 5 µM). Cultures were exposed to compounds for 21 days and cell viability measured by enumerating colony forming units on agar plates on day 0, 7, 14, and 21. MBC was defined as the minimum concentration required to achieve a 2-log kill in 21 days. For compounds with >1-log kill, an assessment of time- and/or concentration-dependence was determined from the kill kinetics. DMSO was used as a positive control for growth. FIG. 10B shows the dose-response curves of compound 4{3,3,0} under low and normal oxygen.

FIG. 10A also shows the intracellular activity and cytotoxicity. The cytotoxicity of compounds towards eukaryotic cells was determined using the THP-1 human monoocytic cell line, as described above.

FIG. 11 shows a comparison of the MIC of compound 4{3,3,0} (discussed above, shown in Table 1, FIG. 4A), and that of the selenylamide against *Mycobacterium tuberculosis*.

The MIC of compounds against other Mycobacteria was determined by measuring bacterial growth after 5 d in the presence of test compounds. Compounds were prepared as 10-point two-fold serial dilutions in DMSO and diluted into 7H9-Tw-OADC medium in 96-well plates with a final DMSO concentration of 2%. The highest concentration of compound was 200 µM, where compounds were soluble in DMSO at 10 mM. Each plate included assay controls for background (medium/DMSO only, no bacterial cells), zero growth (100 µM rifampicin), and maximum growth (DMSO only), as well as a rifampicin dose response curve. Plates were inoculated with Mtb and incubated for 5 days; growth was measured by $OD_{590}$. To calculate the MIC, the 10-point dose response curve was plotted as % growth and fitted to the Gompertz model using GraphPad Prism 5. The MIC was defined as the minimum concentration at which growth was completely inhibited and was calculated from the inflection point of the fitted curve to the lower asymptote (zero growth). In addition, dose response curves were generated using the Levenberg-Marquardt algorithm, and the concentrations that resulted in 50% and 90% inhibition of growth ($IC_{50}$ and $IC_{90}$, respectively) were determined.

Figure 13B:
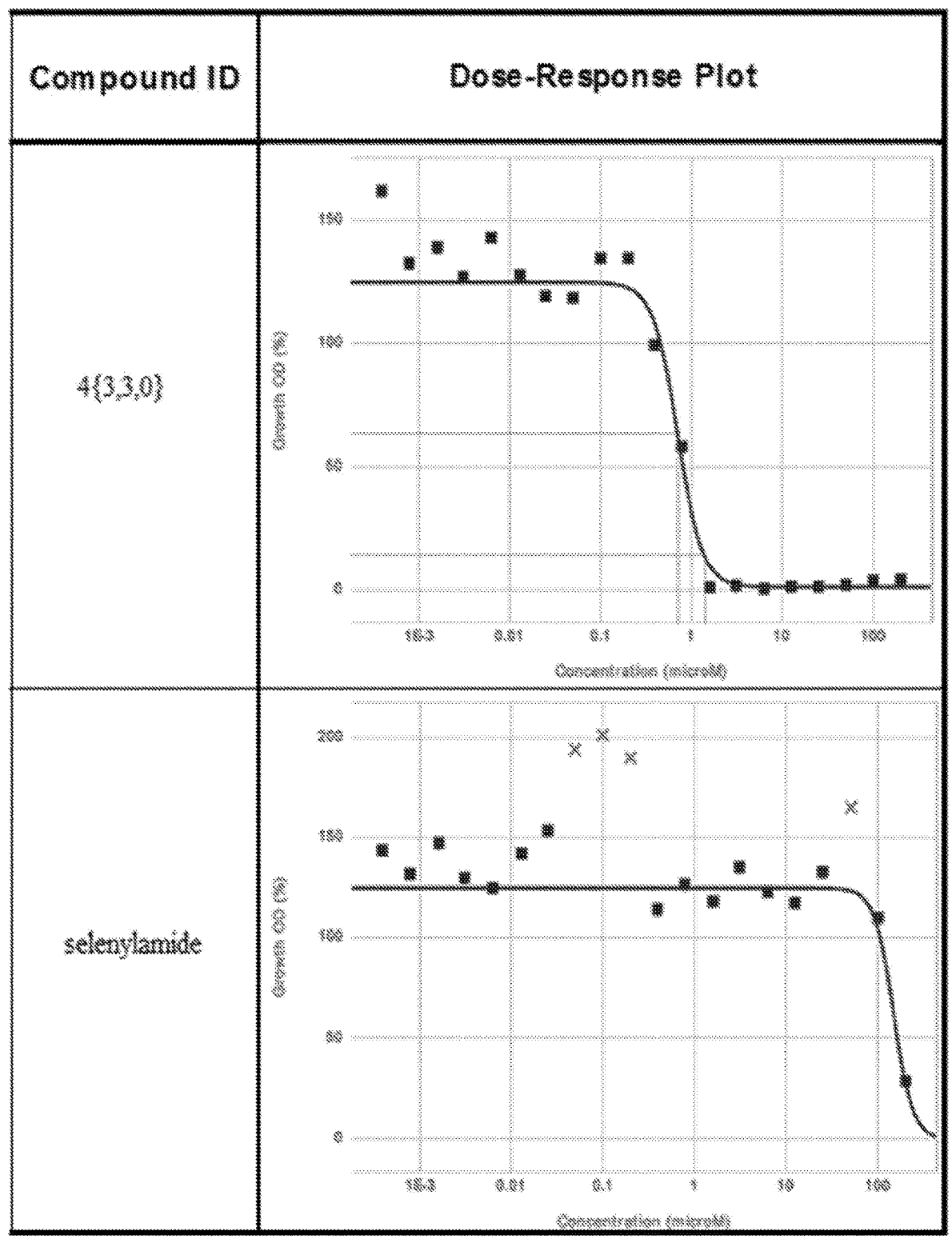
Figure 13C:
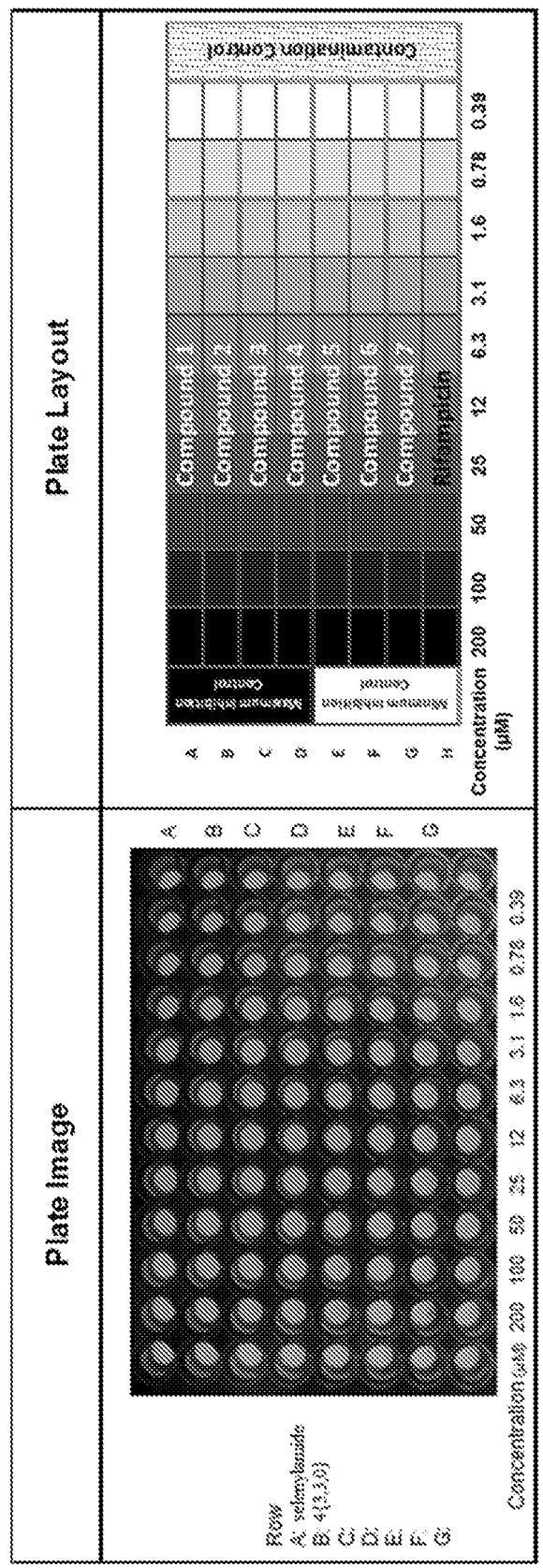

FIGS. 13A-13C show results from an evaluation of the MIC of compound 4{3,3,0} against other disease-relevant Mycobacteria. The activity of compounds against *Mycobacterium abscessus* and *Mycobacterium avium* was assessed under aerobic conditions by determining the minimum inhibitory concentration of compound (MIC). The strains were *M. abscessus* subsp. *bollettii* 103 and *M. avium* subsp. *avium* 2285 (S). The assay was based on measurement of growth in liquid medium of each strain where the readout is optical density (OD) or metabolic activity (using Alamar blue).

The MIC of compound against *Mycobacterium abscessus* and *Mycobacterium avium* was determined by measuring bacterial growth in the presence of test compounds. Compounds were prepared as 20-point two-fold serial dilutions in DMSO and diluted into 7H9-Tw-OADC medium in 96-well plates with a final DMSO concentration of 2%. The highest concentration of compound was 200 µM where compounds were soluble in DMSO at 10 mM. Each plate included assay controls for background (medium/DMSO only, no bacterial cells), zero growth (100 µM rifampicin) and maximum growth (DMSO only), as well as a rifampicin dose response curve.

For *Mycobacterium abscessus*, plates were inoculated with *M. abscessus* and incubated for 3 days at 37° C.; growth was measured by $OD_{590}$. The dose response curve (FIG. 13B) was plotted as % growth and fitted to the Gompertz model. The MIC was defined as the minimum concentration at which growth was completely inhibited and was calculated from the inflection point of the fitted curve to the lower asymptote (zero growth). In addition, dose response curves were generated using the Levenberg-Marquardt algorithm and the concentrations that resulted in 50% and 90% inhibition of growth were determined ($IC_{50}$ and $IC_{90}$, respectively). Rifampicin was included once in each run. MIC values were reported when the following quality control criteria were satisfied: for each place, either no growth in the background (un-inoculated) control wells, or $OD_{590}$>0.2 in maximum growth wells; for each compound curve, MIC values were reported if there were either 2 points with growth >75%, or 2 points with growth <75%. If no point reached 75% inhibition, the MIC was reported as >maximum concentration tested.

For *Mycobacterium avium*, plates were inoculated with *M. avium*, incubated for 5 days at 37° C., and Alamar blue was added to each well (10 µL of Alamar blue to 100 µL culuture) and incubated for 24 h at 37° C. Plates were visually inspected and the color recorded for each well. MIC was defined as the lowest concentration at which no metabolic activity was seen (blue well). MIC values were reported when the following quality control criteria were satisfied: for each plate, background (un-inoculated) control wells remain blue, maximum growth wells are pink, or inhibition control wells are blue; for each compound, MIC values were reported if there was a transition from pink to blue. If all wells were pink, the MIC was reported as >maximum concentration tested. FIG. 13C shows the plate image and plate layout from the *Mycobacterium avium* MIC evaluation.

As seen from FIG. 13A, the MIC of compound 4{3,3,0} against *Mycobacterium abscessus* was 1.11 µg/mL, which is better than the MIC of rifampicin against *Mycobacterium*

*abscessus*. FIG. 13B shows the dose-response curves for compound 4{3,3,0} and the tested selenylamide against *Mycobacterium abscessus*.

FIG. 14 shows a summary of pharmacokinetic data for compound 4{3,3,0} and selenylamide. The results are divided into six sections: compound formatting, plasma protein binding assay, Caco-2 permeability assay, cytochrome P450 inhibition assay, in vitro microsomal stability assay, and 3F HepG2 cytotoxicity. Plasma protein binding for each test compound was determined by equilibrium dialysis. Compounds were tested using a semi-permeable membrame which separates two compartments containing protein (human plasma) and buffer. Molecules can penetrate freely, but proteins cannot pass through the membrane. Test compounds were mixed with human plasma and applied to the device; after equilibration at 37° C. with PBS, the test compound in each compartment was quantified by LC-MS/MS.

Compounds were added to human plasma at a fixed concentration of 5 µM. The mixture was dialyzed in a RED device (Rapid Equilibrium Dialysis, Pierce) against PBS and incubated on an orbital shaker for 4 h at 37° C. Aliquots from plasma and PBS sides were collected; an equal volume of PBS was added to the plasma sample, and an equal volume of plasma was added to the PBS sample. Three volumes of methanol (containing the internal binding standard propranolol) were added to precipitate the proteins and release the compound. Each compound was tested in duplicate. Samples were centrifuged and the supernatant was recovered and analyzed by LC-MS/MS. Each experiment included warfarin as a high-binding control.

The Caco-2 permeability of test compounds was assessed using a Caco-2 cell monolayer. Compound permeability was measured in both directions. For A-B permeability, test compound was added to the apical side of the Caco-2 monolayer and the transport of compound to the basal side monitored. For B-A permeability, test compound was added to the basal side of the Caco-2 monolayer and the transport of the compound to the apical side monitored. Assays were run for 2 h in duplicate. The amount of compound present in each compartment is quantified by LC-MS/MS.

Caco-2 cells were trypsinized, resuspended in medium, and dispensed into a Millipore 96-well Caco-2 plate. The cells were allowed to grow and differentiate for three weeks, with feeding at 2-day intervals. For Apical to Basolateral (A→B) permeability, the compound was added to the apical (A) side and amount of permeation was determined on the basolateral (B) side; for Basolateral to Apical (B→A) permeability, the compound was added to the B side and the amount of permeation was determined on the A side. Each experiment included the control compounds atenolol (low permeability), propranolol (high permeability) and talinolol (P-gp efflux control).

Each compound was tested for inhibition of six cytochrome P450 enzyme isoforms—CYP2B6, CYP2C8, CYP2C9, CYP2C19, CYP2D6, and CYP3A4. For each assay, human liver microsomes were incubated with a probe substrate for each CYP isoform in the presence of compound. The formation of metabolites for each isoform was quantified by LC-MS/MS as a measure of enzyme activity. Enzyme activity was calculated and $IC_{50}$ generated. These results are depicted in FIGS. 10C-10F.

Compounds were prepared as a 7-point dilution series in acetonitrile:DMSO (9:1). The final DMSO content in the reaction mixture was equal in all solutions used within an assay, and was <0.2%. Samples were run in duplicate. Compounds were incubated with human liver microsomes in sample buffer containing 2 mM NADPH and probe substrate in a 200 µL assay final volume. Reactions were incubated at 37° C. for the optimal time (10-60 min) and terminated by addition of methanol containing internal standard (propranolol) for analytical quantification. Samples were incubated at 4° C. for 10 min and centrifuged at 4° C. for 10 min. The supernatant was removed and the probe substrate metabolite was analyzed by LC-MS/MS. A decrease in the formation of the metabolite compared to vehicle control was used to calculate an $IC_{50}$ value (the test concentration which produces 50% inhibition).

Compounds were tested for in vitro microsomal stability using pooled human liver S9 microsomes. Microsomes were incubated with the test compound at 37° C. in the presence of the co-factor NADPH; the reaction was terminated, the supernatant was recovered, and test compounds were quantified by LC-MS/MS. A fixed concentration of test compound was tested in duplicate at 5 time points and compound stability expressed as a function of time.

Figure 10G:
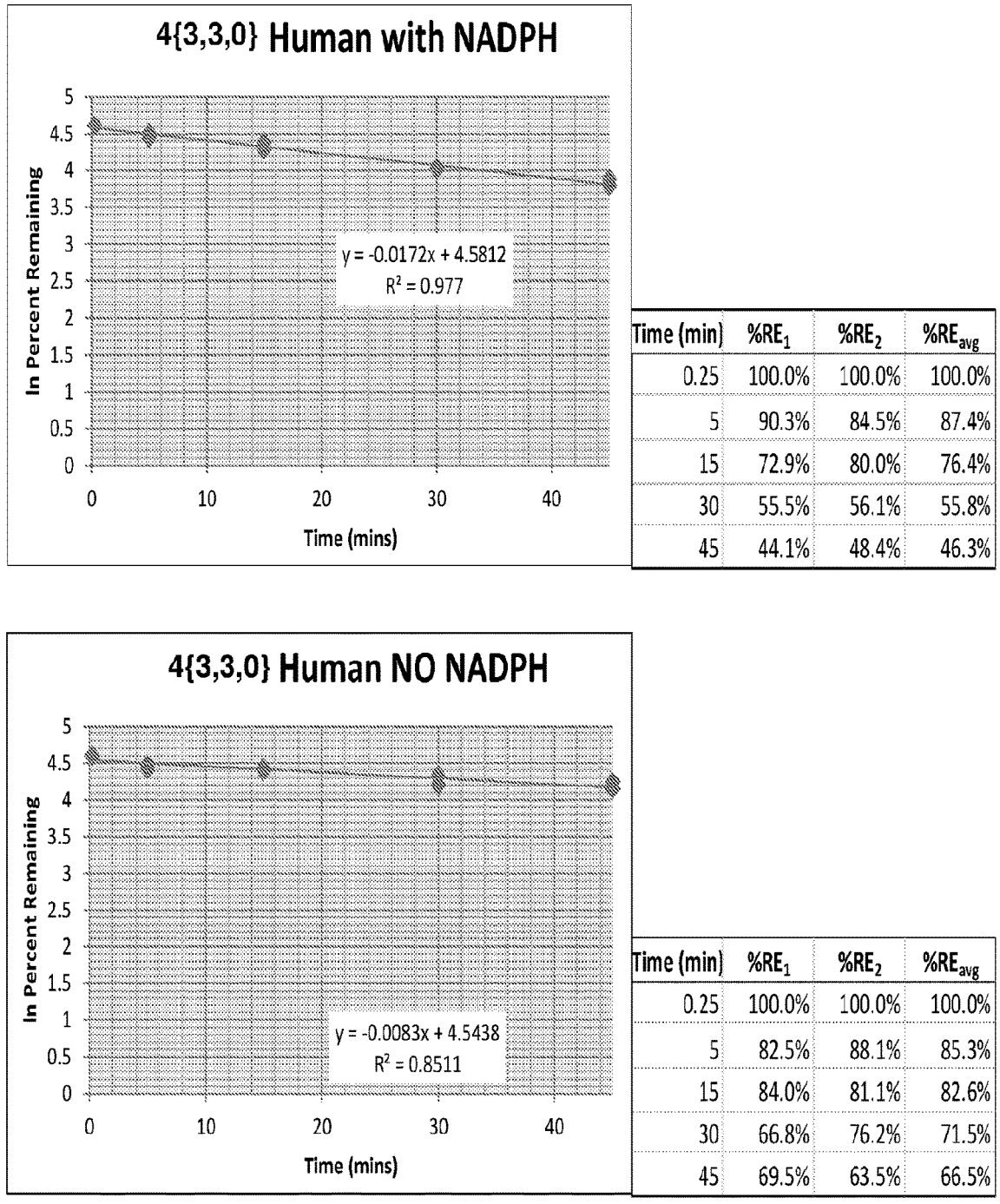

Compounds were incubated with human liver microsomes at 37° C. in duplicate. Each reaction contained 0.3 mg/mL human microsomal protein in assay buffer. Samples were removed at 0, 5, 15, 30, and 45 minutes, mixed with an equal volume of stop solution (containing propranolol as an internal standard), and incubated for >10 min at −20° C. An additional volume of water was added, samples were centrifuged to remove precipitated protein and the supernatants were analyzed by LC-MS/MS to quantitate the remaining parent compound. A control reaction omitting NADPH (control buffer) was performed for each compound to detect NADPH-free degradation. Verapamil and dextromethorphan were included as control compounds. These results for compound 4{3,3,0} are shown in FIG. 10G.

Figure 10H:
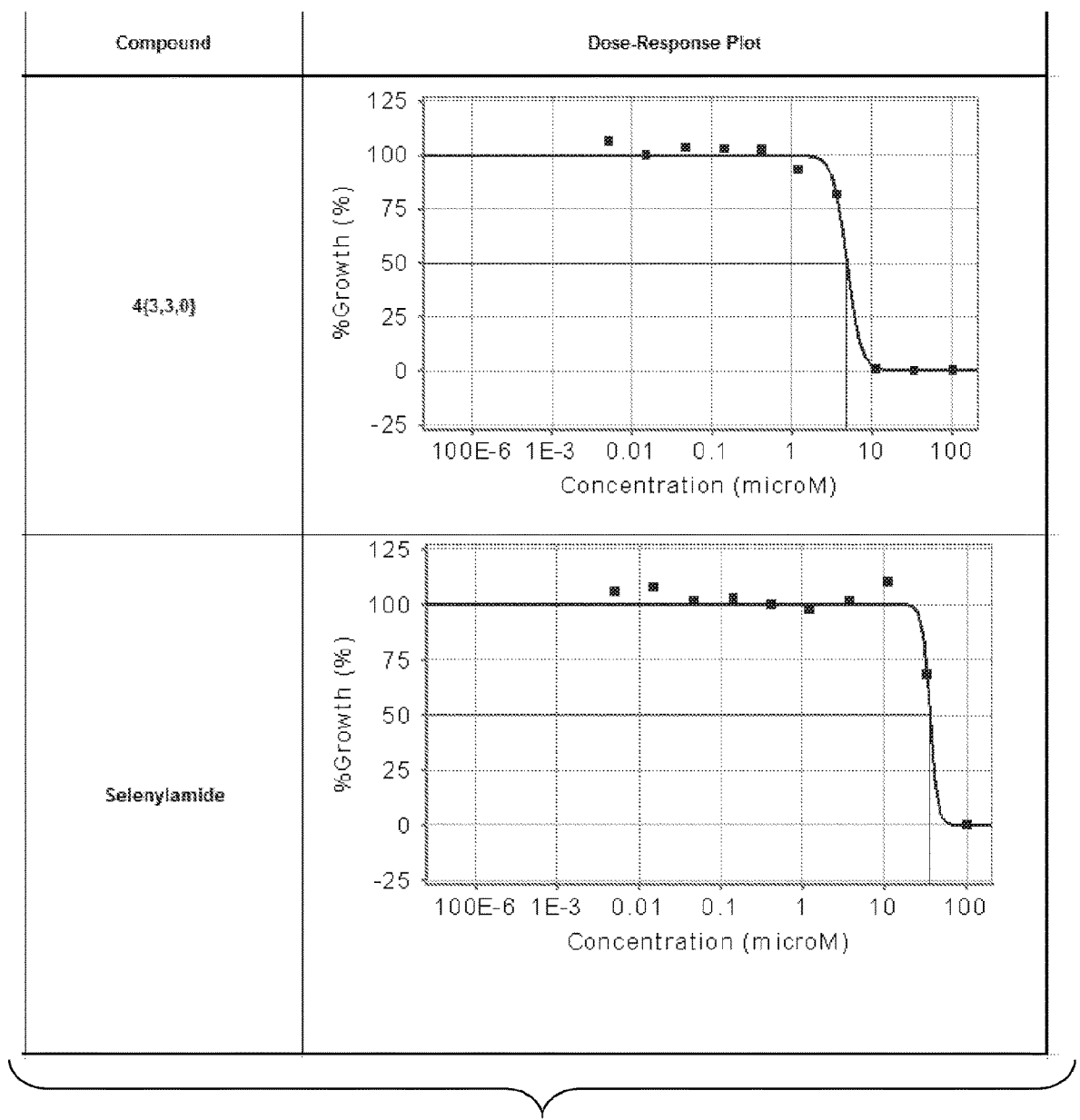
FIG. 10H shows the results of a HepG2 cytotoxicity assay for compound 4{3,3,0} and the selenylamide.

The cytotoxicity of compounds towards eukaryotic cells was determined using the human liver cells (HepG2). HepG2 cells are incubated with compounds for 72 hours and cell viability is measured. The $TC_{50}$ was determined as the concentration of compound causing a 50% loss in viability. The cytotoxicity of compounds was determined by measuring HepG2 cell viability growth after 3 d in the presence of test compounds. Compounds were prepared as 10-point three-fold serial dilutions in DMSO. The highest concentration of compound tested was 100 µM where compounds were soluble in DMSO at 10 mM. HepG2 cells were cultured in complete DMEM, inoculated into 384-well assay plates containing compounds and incubated for 24 h at 37° C., 5% $CO_2$. Compounds were added and cells were cultured for a further 72 h. The final DMSO concentration was 1%. Cell viability was determined using the CellTiter-Glo® Luminescent Cell Viability Assay (Promega) and measuring relative luminescent units (RLU). The dose response curve was fitted using the Levenberg-Marquardt algorithm. The $TC_{50}$ was defined as the compound concentration that produced 50% loss of cell viability. Each run included staurosporine as a control. These results are shown in FIG. 10H.

Evaluation of Compounds 506-509

FIG. 22 shows a summary of the results from subjecting compounds 506-509 to the same assays as described above for compound 4{3,3,0} and shown in FIG. 10A. FIG. 22 shows the MIC for compounds 506-509 against *M. tuberculosis* under aerobic conditions, the MIC for compounds 506-509 against *M. tuberculosis* under low oxygen conditions, the minimum bactericidal concentration of compounds 506-509, and the intracellular activity and cytotoxicity of compounds 506-509.

The antimicrobial activity of compounds 506-509 against *Mycobacterium tuberculosis* H37Rv grown under aerobic conditions was assessed by determining the minimum inhibitory concentration (MIC) of compound, i.e., the concentration required to prevent growth. The assay was based on measurement of growth in liquid medium of a fluorescent reporter strain of H37Rv where the readout is either optical density (OD) or fluorescence. The use of two readouts minimizes problems caused by compound precipitation or autofluoresence. A linear relationship between OD and fluorescence readout has been established justifying the use of fluorescence as a measure of bacterial growth. MICs generated from the OD are shown in the summary data. The strain has been fully characterized and is equivalent to the parental strain in microbiological phenotypes and virulence.

The MIC of compounds 506-509 was determined by measuring bacterial growth after 5 d in the presence of test compounds. Compounds were prepared as 20-point two-fold serial dilutions in DMSO and diluted into 7H9-Tw-OADC medium in 96-well plates with a final DMSO concentration of 2%. The highest concentration of compound was 200 µM where compounds were soluble in DMSO at 10 mM. For compounds with limited solubility, the highest concentration was 50× less than the stock concentration e.g. 100 µM for 5 mM DMSO stock, 20 µM for 1 mM DMSO stock. Each plate included assay controls for background (medium/DMSO only, no bacterial cells), zero growth (2 µM rifampicin), and maximum growth (DMSO only), as well as a rifampicin dose response curve. Plates were inoculated with M. tuberculosis and incubated for 5 days: growth was measured by $OD_{590}$ and fluorescence (Ex 560/Em 590) using a BioTek™ Synergy H4 plate reader. Growth was calculated separately for $OD_{590}$ and RFU. To calculate the MIC, the dose response curve was plotted as % growth and fitted to the Gompertz model using GraphPad Prism 6. The MIC was defined as the minimum concentration at which growth was completely inhibited and was calculated from the inflection point of the fitted curve to the lower asymptote. In addition dose response curves were generated using the Levenberg-Marquardt algorithm and the concentrations that resulted in 50% and 90% inhibition of growth were determined ($IC_{50}$ and $IC_{90}$ respectively).

The antimicrobial activity of compounds 506-509 against M. tuberculosis H37Rv grown under hypoxic conditions was assessed using the low oxygen recovery assay (LORA). Bacteria were first adapted to low oxygen conditions and then exposed to compounds under hypoxia; this was followed by a period of outgrowth in aerobic conditions and growth is measured using luminescence.

Test compounds were prepared as 20-point two-fold serial dilutions in DMSO and diluted into DTA medium in 96-well plates with a final DMSO concentration of 2%. The highest concentration of compound was 200 µM where compounds were soluble in DMSO at 10 mM. For compounds with limited solubility, the highest concentration was 50× less than the stock concentration, e.g., 100 µM for 5 mM DMSO stock, 20 µM for 1 mM DMSO stock. Control compounds were prepared as two-fold serial dilutions in DMSO and diluted into DTA medium in 96-well plates with a final DMSO concentration of 2%.

M. tuberculosis constitutively expressing the luxABCDE operon was inoculated into DTA medium in gas-impermeable glass tubes and incubated for 18 days to generate hypoxic conditions (Wayne model of hypoxia). At this point, bacteria were in a non-replicating state (NRP stage 2) induced by oxygen depletion.

Oxygen-deprived bacteria were inoculated into compound assay plates and incubated under anaerobic conditions for 10 days followed by incubation under aerobic conditions (outgrowth) for 28 h. Growth was measured by luminescence. Oxygen-deprived bacteria were also inoculated into compound assay plates and incubated under aerobic conditions for 6 days. Growth was measured by luminescence. Rifampicin was included in each plate and metronidazole was included in each run as positive controls for aerobic and anaerobic killing of M. tuberculosis, respectively.

Figure 23:
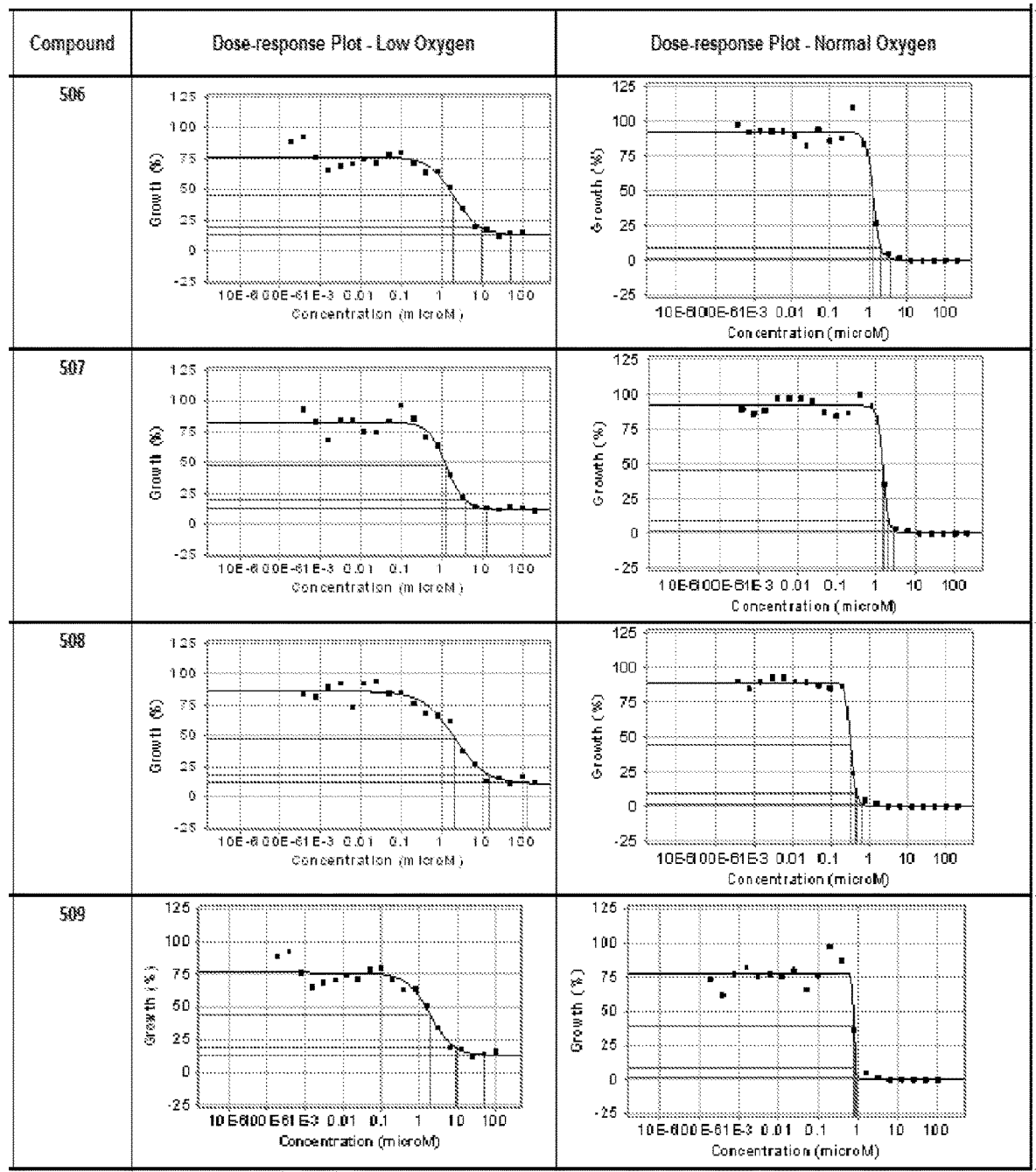
FIG. 23: Dose-response curves for compounds 506-509 against *M. tuberculosis* under low oxygen and normal oxygen conditions.

FIG. 23 shows the dose-response curves for compounds 506-509 under low oxygen and normal oxygen conditions.

The bactericidal activity of compounds was assessed against M. tuberculosis H37Rv grown in aerobic conditions in 7H9-Tw-OADC medium. Viable cell counts are measured over 3 weeks of exposure to determine the rate of kill.

M. tuberculosis was grown aerobically to logarithmic phase and inoculated into liquid medium containing four different compound concentrations with a final maximum concentration of 2% DMSO. For compounds with an MIC<20 µM (from Task Group 1 assay), the concentrations selected were 10×MIC, 5×MIC, 1×MIC, and 0.25×MIC. Cultures were exposed to compounds for 21 days and cell viability measured by enumerating colony forming units on agar plates on day 0, 7, 14 and 21.

MBC was defined as the minimum concentration required to achieve a 2-log kill in 21 days. For compounds with >1-log kill, an assessment of time- and/or concentration-dependence was determined from the kill kinetics. DMSO was used as a positive control for growth.

Figure 24:
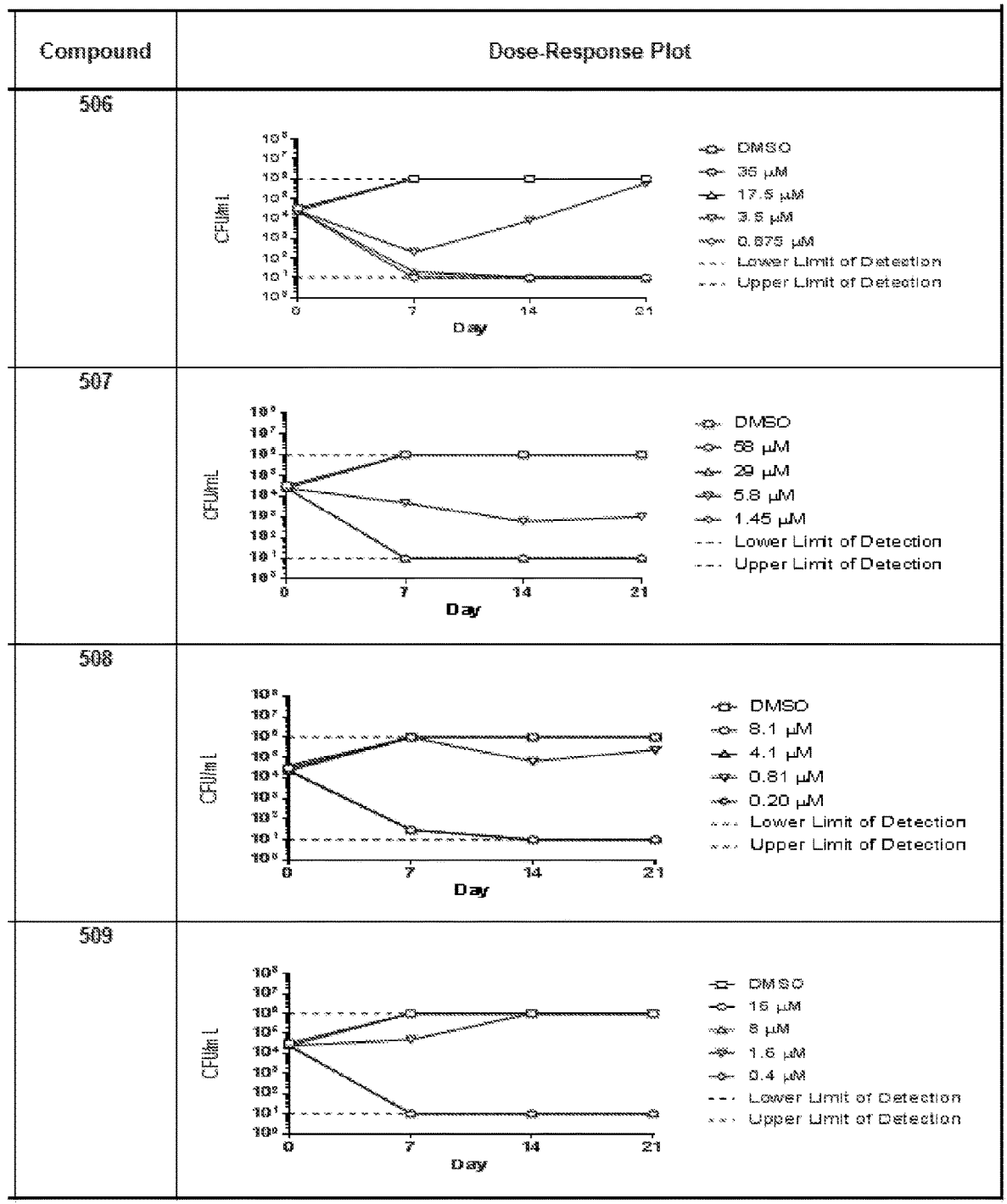
FIG. 24: Dose-response plots for determining the minimum bactericidal activity of compounds 506-509.

FIG. 24 shows the dose-response plots for determining the minimum bactericidal activity of compounds 506-509.

The cytotoxicity of compounds towards eukaryotic cells was determined using the THP-1 human monocytic cell line. THP-1 cells were differentiated into macrophage-like cells using PMA and incubated with compounds for 72 hours and cell viability is measured. The $IC_{50}$ was determined as the concentration of compound causing a 50% loss in viability.

The intracellular activity of compounds was measured using THP1 infected with M. tuberculosis. THP-1 cells are differentiated into macrophage-like cells using PMA and infected with bacteria. Infected cells are exposed to compounds for 72 hours. Viable bacterial counts were measured using luminescence as a measure of intracellular growth.

The cytotoxicity of compounds was determined by measuring THP-1 cell viability after 3 days in the presence of test compounds. Compounds were prepared as 10-point serial dilutions in DMSO. The highest concentration of compound tested was 50 µM where compounds were soluble in DMSO at 10 mM. For compounds with limited solubility, the highest concentration was 200× less than the stock concentration, e.g., 25 µM for 5 mM DMSO stock, 5 µM for 1 mM DMSO stock. THP-1 cells were cultured in complete RPMI and differentiated into macrophage-like cells using 80 nM PMA overnight at 37° C., 5% $CO_2$ Cells were inoculated into assay plates and cultured for 24 h before compound dilutions were added to a final DMSO concentration of 0.5%. Each run included staurosporine as a control. Assay plates were incubated for 3 days at 37° C., 5% $CO_2$; growth was measured using the CellTiter-Glo® Luminescent Cell Viability Assay (Promega) which uses ATP as an indicator of cell viability. Relative luminescent units (RLU) were measured using a Biotek Synergy 4 plate reader. The dose response curve was fitted using the Levenberg-Marquardt algorithm. The $IC_{50}$ was defined as the compound concentration that resulted in 50% viability.

The activity of compounds against intracellular bacteria was determined by measuring viability in infected THP-1 cell after 3 days in the presence of test compounds. Compounds were prepared as 10-point serial dilutions in DMSO. The highest concentration of compound tested was 50 µM where compounds were soluble in DMSO at 10 mM. For compounds with limited solubility, the highest concentration was 200× less than the stock concentration, e.g., 25 µM for 5 mM DMSO stock, 5 µM for 1 mM DMSO stock.

THP-1 cells were cultured in complete RPMI and differentiated into macrophage-like cells using 80 nM PMA overnight at 37° C., 5% $CO_2$ THP-1 cells were infected with a luminescent strain of H37Rv (which constitutively expresses luxABCDE) at a multiplicity of infection of 1 and incubated overnight at 37° C., 5% $CO_2$. Infected cells were recovered using Accutase/EDTA solution, washed twice with PBS to remove extracellular bacteria and seeded into assay pates. Compound dilutions were added to a final DMSO concentration of 0.5%. Assay plates were incubated for 72 h at 37° C., 5% $CO_2$. Each run included isoniazid as a control. Relative luminescent units (RLU) were measured using a Biotek Synergy 2 plate reader. The dose response curve was fitted using the Levenberg-Marquardt algorithm. The $IC_{50}$ and $IC_{90}$ were defined as the compound concentrations that produced 50% and 90% inhibition of bacterial growth respectively.

Figure 25:
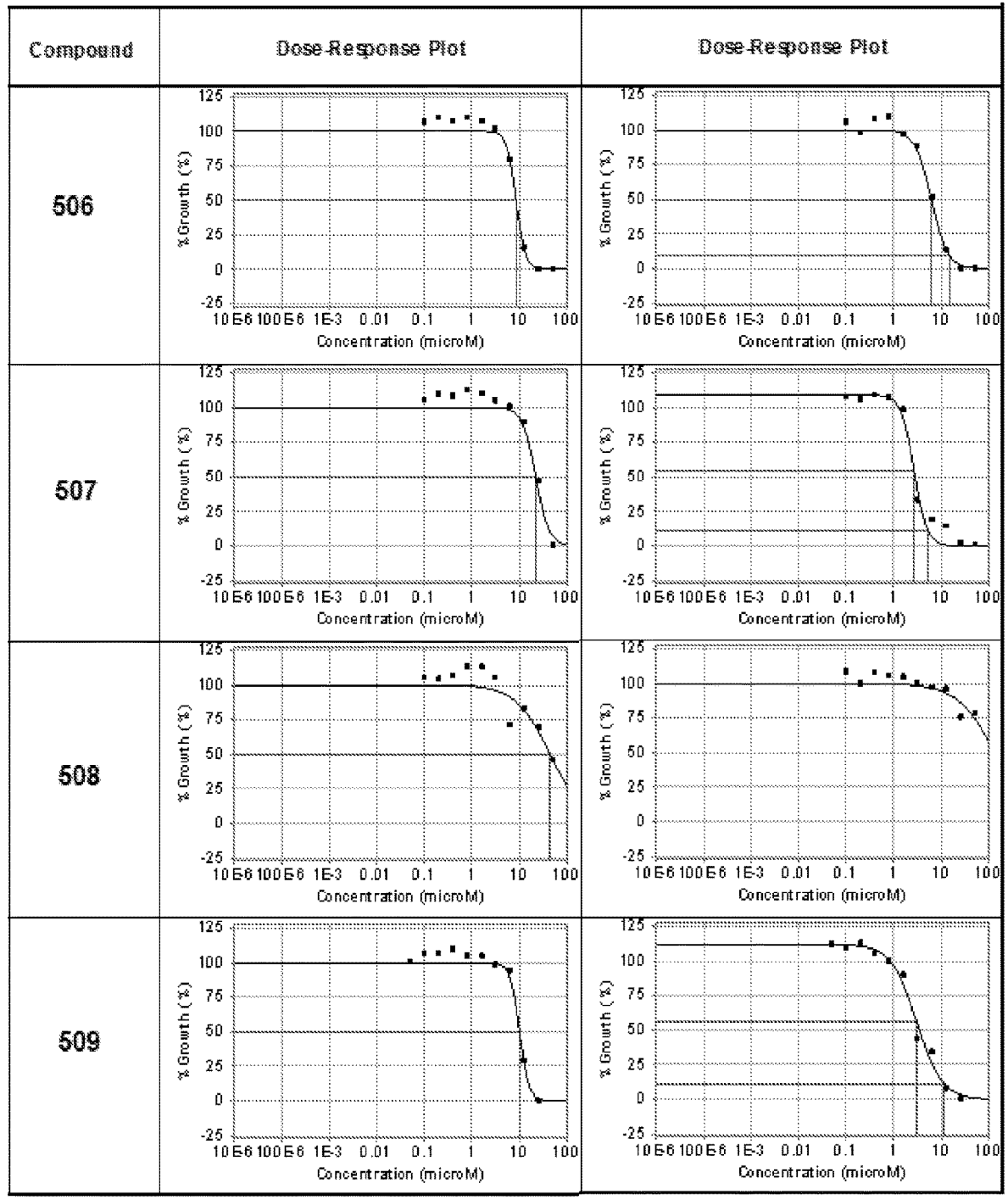
FIG. 25: Dose-response plots for compounds 506-509 in cytotoxicity assay (left) and intracellular activity assay (right).

FIG. 25 shows the dose-response curves for compounds 506-509 from the cytotoxicity assay (left) and the intracellular activity assay (right).

The activity of compounds 506-509 against five resistant isolates of *M. tuberculosis* strains was assessed under aerobic conditions by determining the minimum inhibitory concentration (MIC) of compound. Strains tested were two isoniazid resistant strains (INH-R1 and INH-R2), two rifampicin resistant strains (RIF-R1 and RIF-R2), and a fluoroquinolone resistant strain (FQ-R1). The assay was based on measurement of growth in liquid medium of each strain where the readout is optical density (OD).

INH-R1 was derived from H37Rv and is a katG mutant (Y155*=truncation). INH-R2 is strain ATCC35822. RIF-R1 was derived from H37Rv and is an rpoB mutant (S522L). RIF-R2 is strain ATCC35838. FQ-R1 is a fluoroquinolone-resistant strain derived from H37Rv and is a gyrA mutant (D94N)

The MIC of compound was determined by measuring bacterial growth after 5 d in the presence of test compounds. Compounds were prepared as 20-point two-fold serial dilutions in DMSO and diluted into 7H9-Tw-OADC medium in 96-well plates with a final DMSO concentration of 2%. The highest concentration of compound was 200 µM where compounds were soluble in DMSO at 10 mM. For compounds with limited solubility, the highest concentration was 50× less than the stock concentration e.g. 100 µM for 5 mM DMSO stock, 20 µM for 1 mM DMSO stock. Each plate included assay controls for background (medium/DMSO only, no bacterial cells), zero growth (2 µM rifampicin) and maximum growth (DMSO only), as well as a rifampicin dose response curve. Plates were inoculated with *M. tuberculosis* and incubated for 5 days; growth was measured by $OD_{590}$. To calculate the MIC, the dose response curve was plotted as % growth and fitted to the Gompertz model using GraphPad Prism 6. The MIC was defined as the minimum concentration at which growth was completely inhibited and was calculated from the inflection point of the fitted curve to the lower asymptote. In addition dose response curves were generated using the Levenberg-Marquardt algorithm and the concentrations that resulted in 50% and 90% inhibition of growth were determined ($IC_{50}$ and $IC_{90}$ respectively). FIG. 26 shows a summary of this data.

The activity of compounds 506-509 against *Mycobacterium abscessus* and *Mycobacterium avium* was assessed under aerobic conditions by determining the minimum inhibitory concentration of compound (MIC). The strains were *M. abscessus* subsp. *bollettii* 103 and *M. avium* subsp. *avium* 2285 (S). The assay was based on measurement of growth in liquid medium of each strain where the readout is optical density (OD) or metabolic activity (using Alamar blue).

The MIC of compound was determined by measuring bacterial growth in the presence of test compounds. Compounds were prepared as 20-point two-fold serial dilutions in DMSO and diluted into 7H9-Tw-OADC medium in 96-well plates with a final DMSO concentration of 2%. The highest concentration of compound was 200 µM where compounds were soluble in DMSO at 10 mM. For compounds with limited solubility, the highest concentration was 50× less than the stock concentration e.g. 100 µM for 5 mM DMSO stock, 20 µM for 1 mM DMSO stock. Each plate included assay controls for background (medium/DMSO only, no bacterial cells), 2 µM rifampicin, and maximum growth (DMSO only), as well as a rifampicin dose response curve.

For *Mycobacterium abscessus*, plates were inoculated with *M. abscessus* and incubated for 3 days at 37° C.; growth was measured by $OD_{590}$. To dose response curve was plotted as % growth and fitted to the Gompertz model. The MIC was defined as the minimum concentration at which growth was completely inhibited and was calculated from the inflection point of the fitted curve to the lower asymptote. In addition dose response curves were generated using the Levenberg-Marquardt algorithm and the concentrations that resulted in 50% and 90% inhibition of growth were determined ($IC_{50}$ and $IC_{90}$ respectively). Rifampicin was included once in each run.

For *Mycobacterium avium*, plates were inoculated with *M. avium*, incubated for 5 days at 37° C. and Alamar blue was added to each well (10 µL of Alamar blue to 100 µL culture) and incubated for 24 h at 37° C. Plates were visually inspected and the color recorded for each well. MIC was defined as the lowest concentration at which no metabolic activity was seen (blue well).

FIG. 27 shows a summary of the MICs for compounds 506-509 against *M. abscessus* and *M. avium*.

Evaluation of Compounds 510-512

Figure 29A:
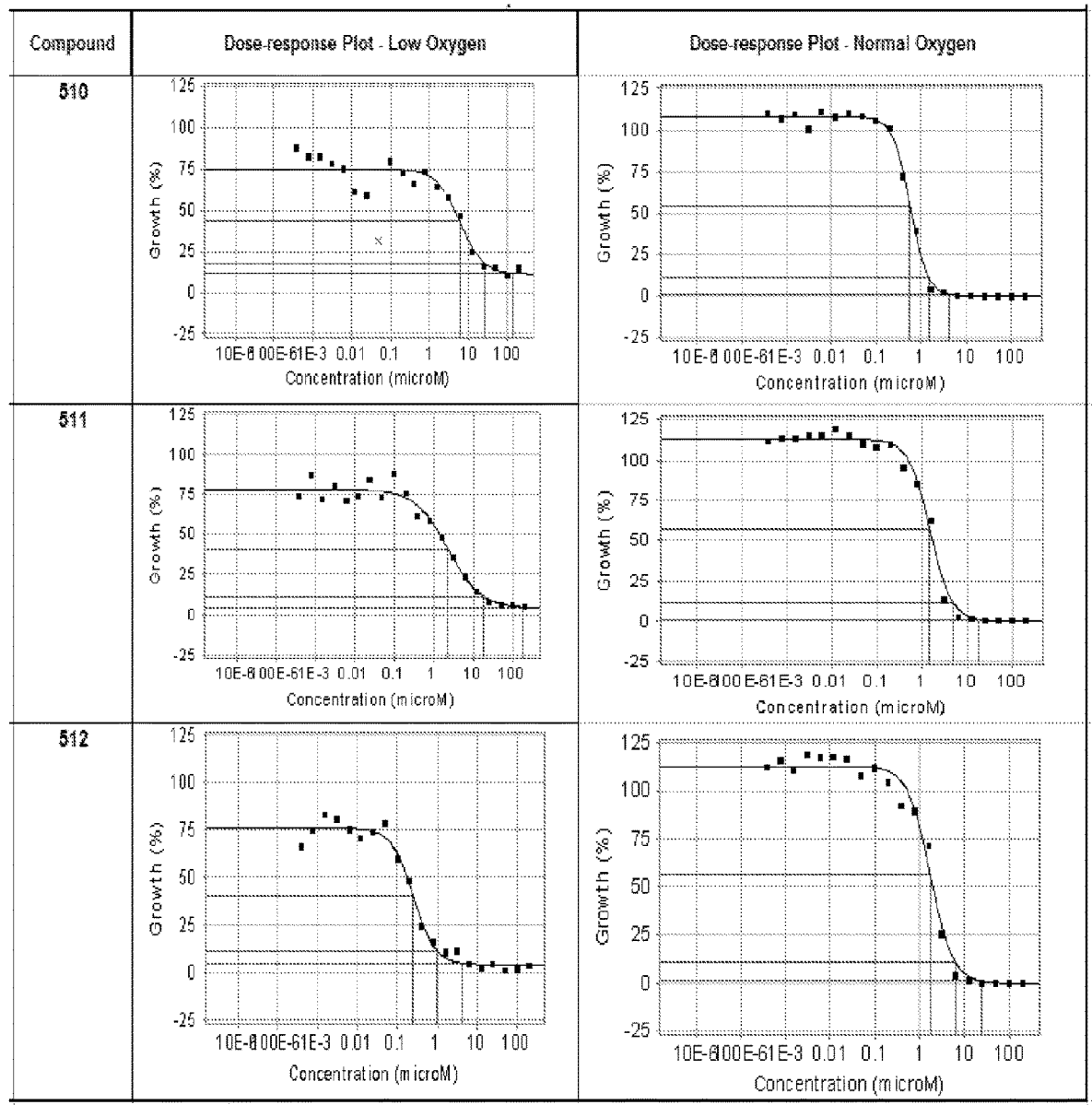
FIGS. 29A-29B: Dose-response plots for compounds 510-512 against *M. tuberculosis* under low oxygen and normal oxygen conditions (FIG. 29A), and the same plots for control compounds rifampicin and metronidazole (FIG. 29B).
Figure 29B:
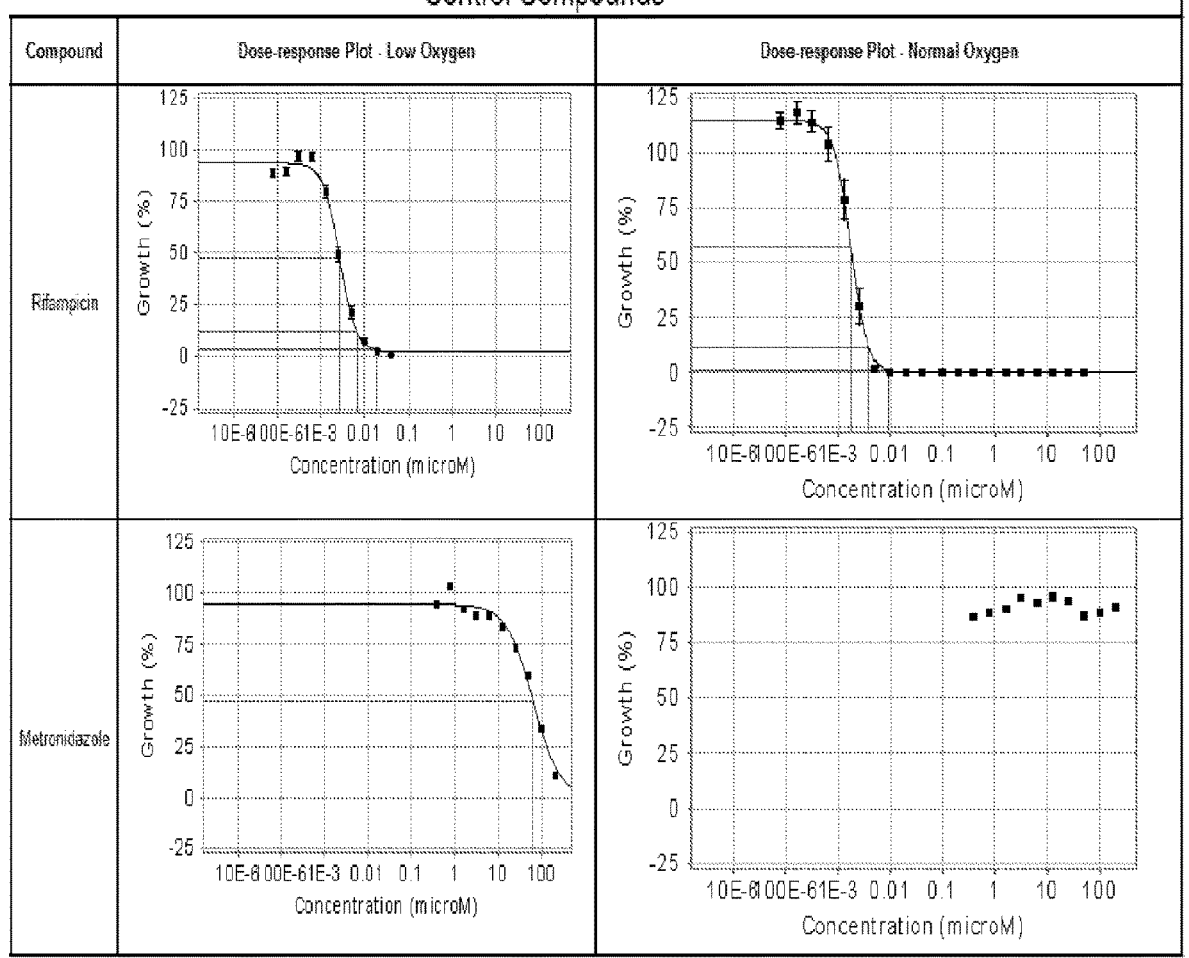
Figure 30:
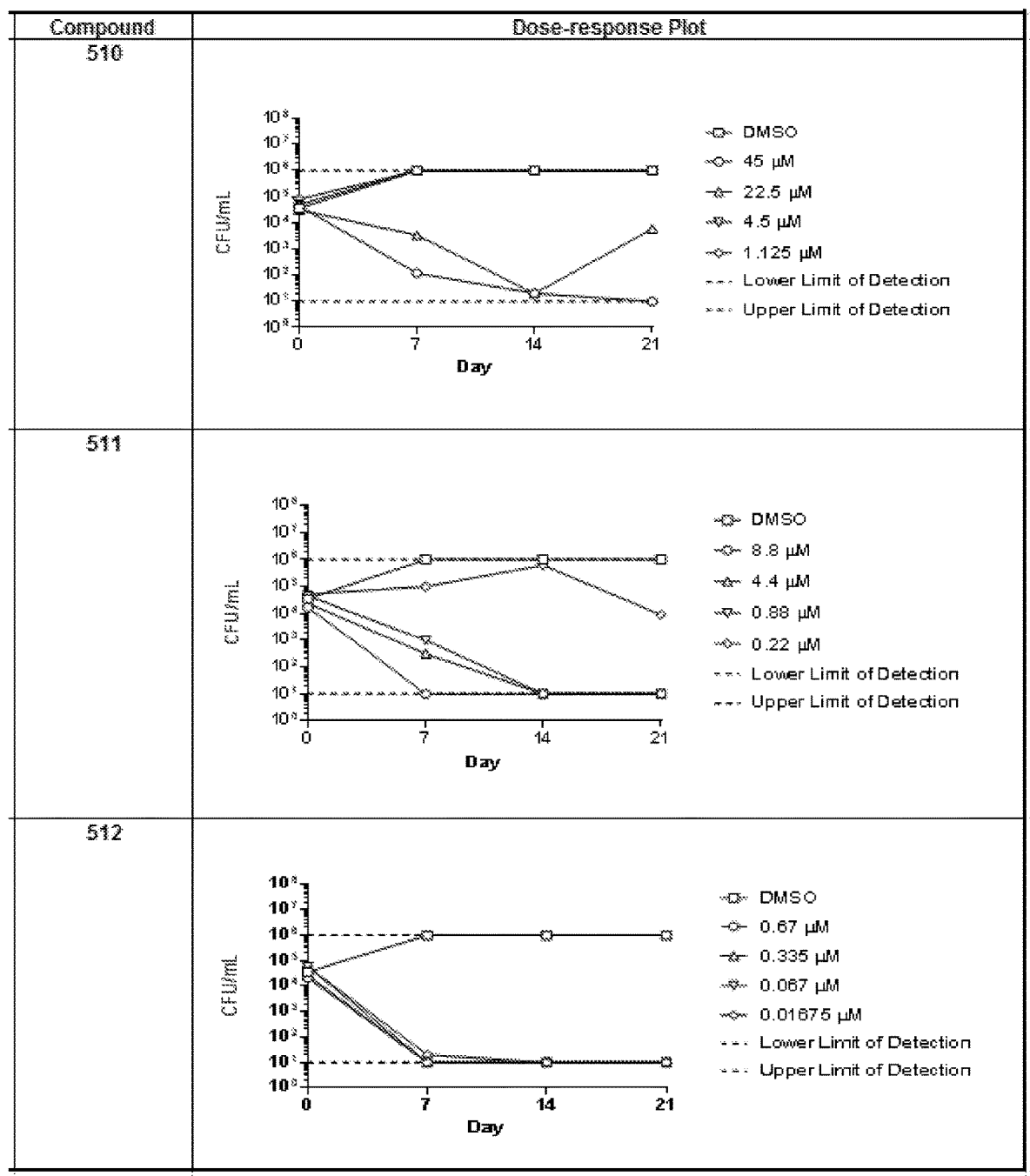
FIG. 30: Dose-response plots for determining the minimum bactericidial activity of compounds 510-512.
Figure 31A:
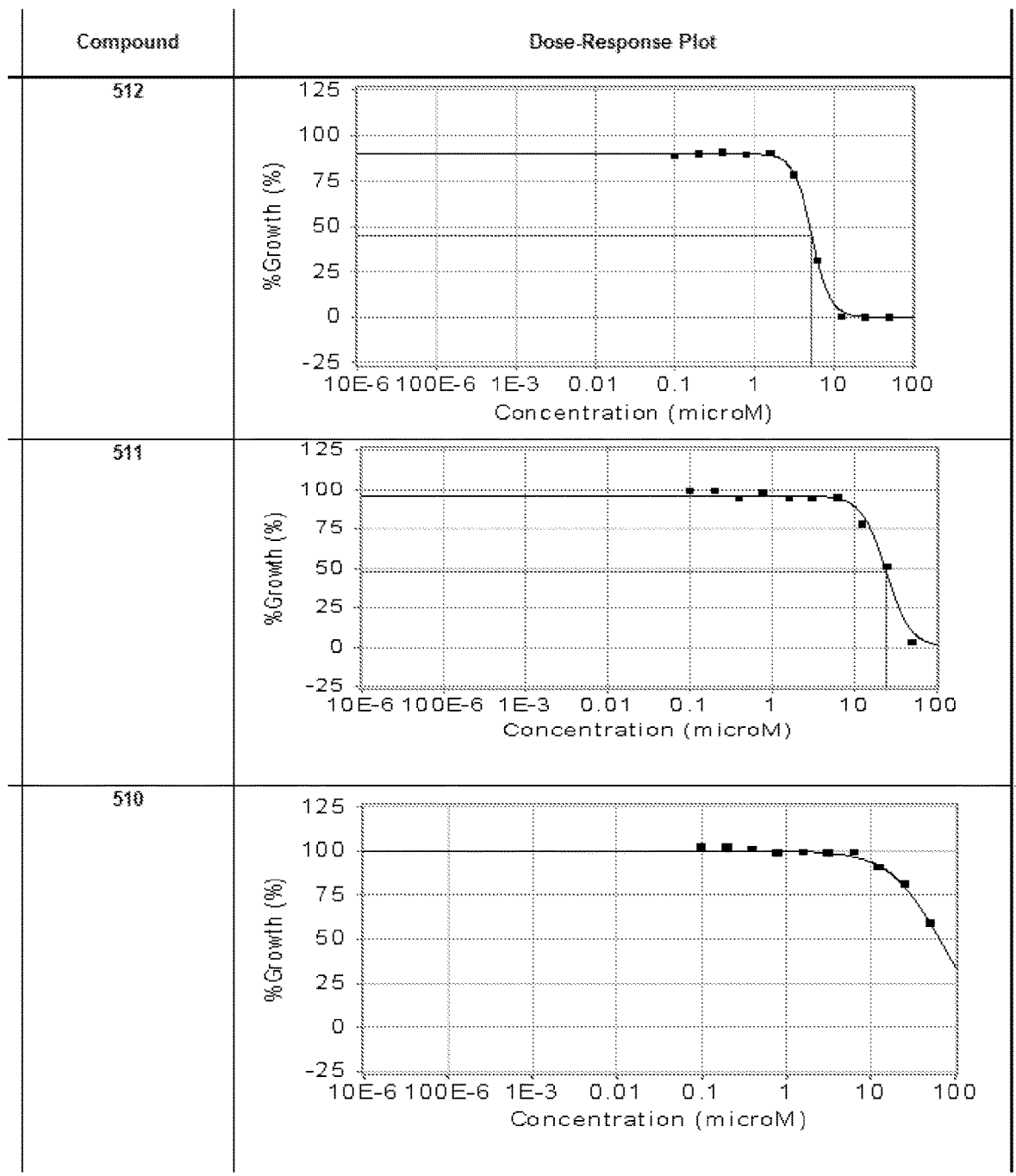
FIGS. 31A-31B: Dose-response plots for compounds 510-512 in cytotoxicity assay (FIG. 31A) and intracellular assay (FIG. 31B).
Figure 31B:
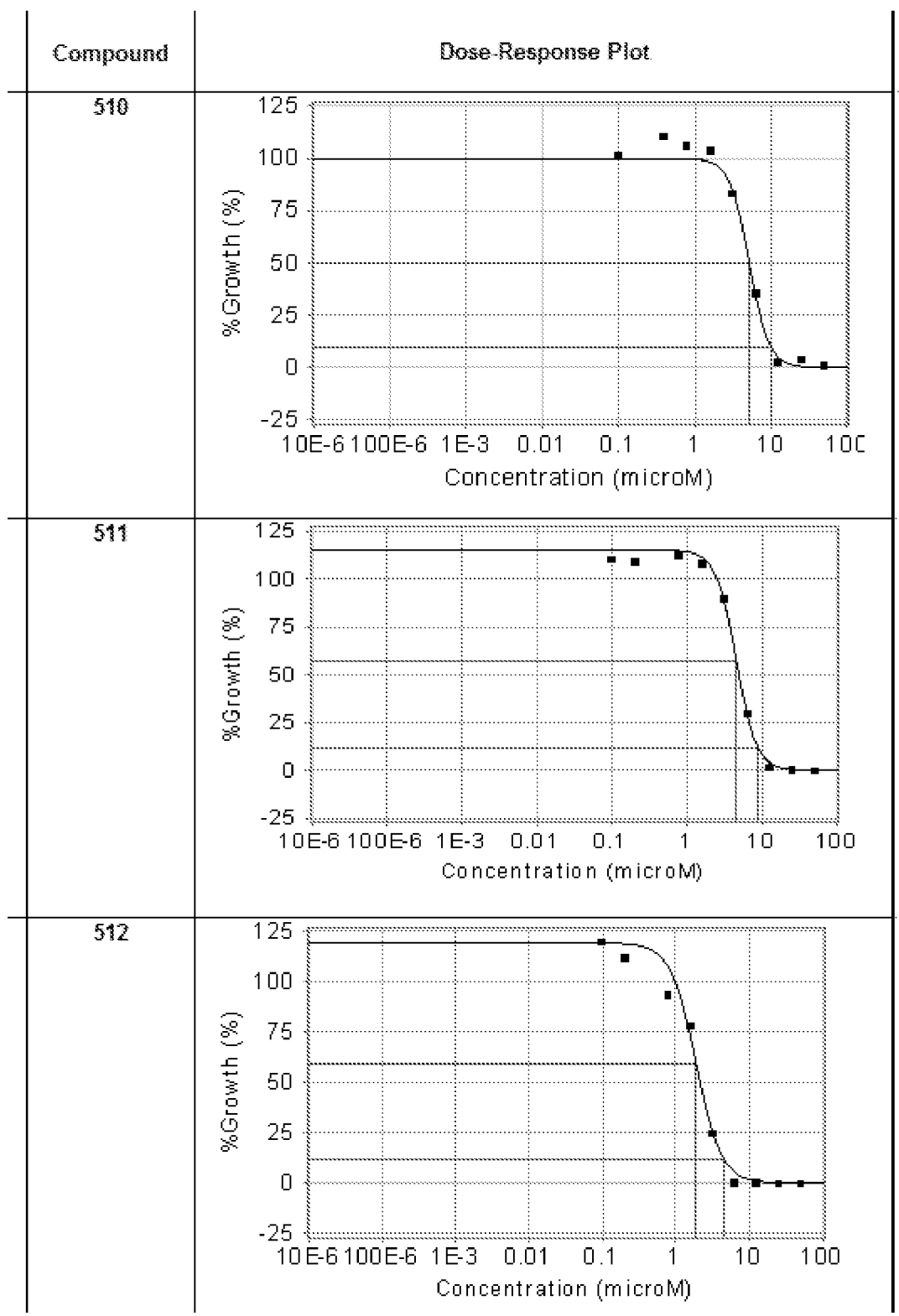

Compounds 510-512 were evaluated through the same procedures as described above for compounds 506-509. FIG. 28 shows a summary of this data for compounds 510-512. FIG. 29A shows the dose-response curves for compounds 510-512 against *M. tuberculosis* H37Rv under low oxygen (left) and normal oxygen (right) conditions, and FIG. 29B shows the same results for control compounds. FIG. 30 shows the dose-response plots for determining the minimum bactericidial activity of compounds 510-512. FIG. 31A shows the dose-response plots for compounds 510-512 in cytotoxicity assay. FIG. 31B shows the dose-response plots for compounds 510-512 in the intracellular assay. FIG. 32 shows a summary of the MICs against resistant isolates for compounds 510-512 and control compounds.

Evaluation of Compounds 513-515

Figure 34:
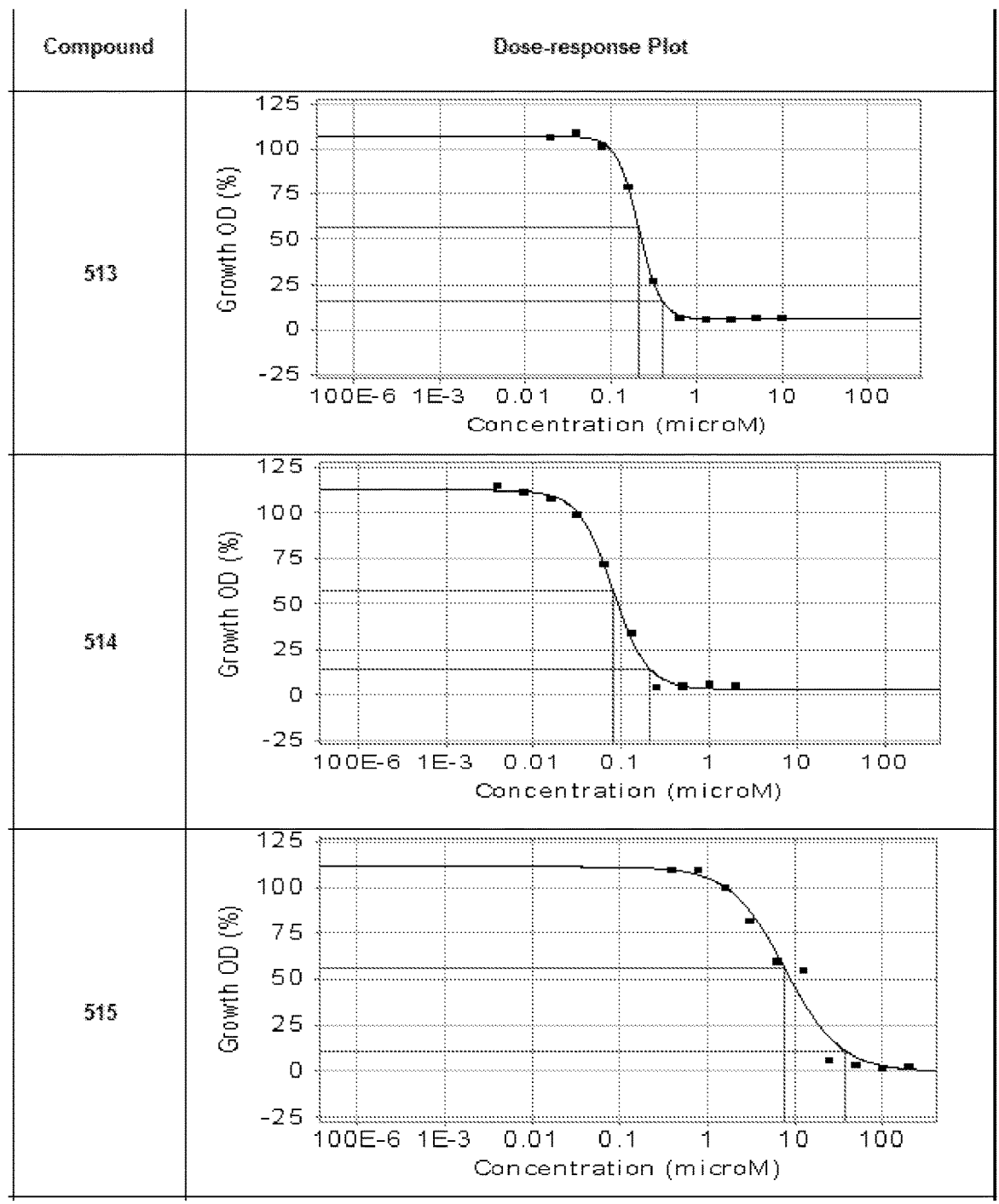
FIG. 34: Dose-response plots for compounds 513-515 against *M. tuberculosis* H37Rv grown under aerobic conditions.

Compounds 513-515 were evaluated through the same procedures as described above for compounds 506-509. FIG. 33 shows a summary of this data for compounds 513-515. FIG. 34 shows the dose-response plots for compounds 513-515 against *M. tuberculosis* H37Rv grown under aerobic conditions. FIG. 35 shows a summary of MIC data for compounds 513-515 against *M. abscessus* and *M.*

Figure 36:
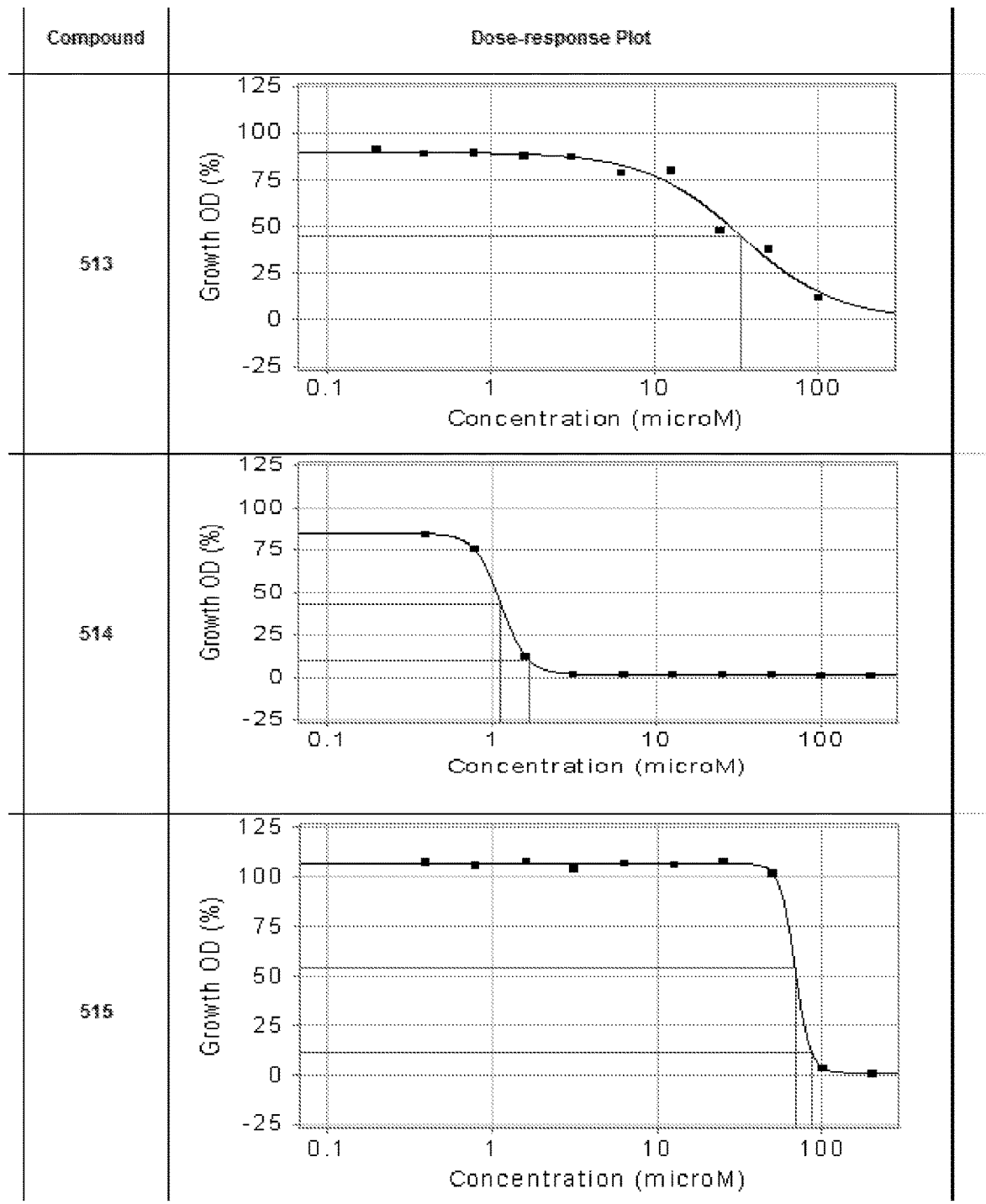
FIG. 36: Dose-response plots for compounds 513-515 against *M. abscessus*.
Figure 38:
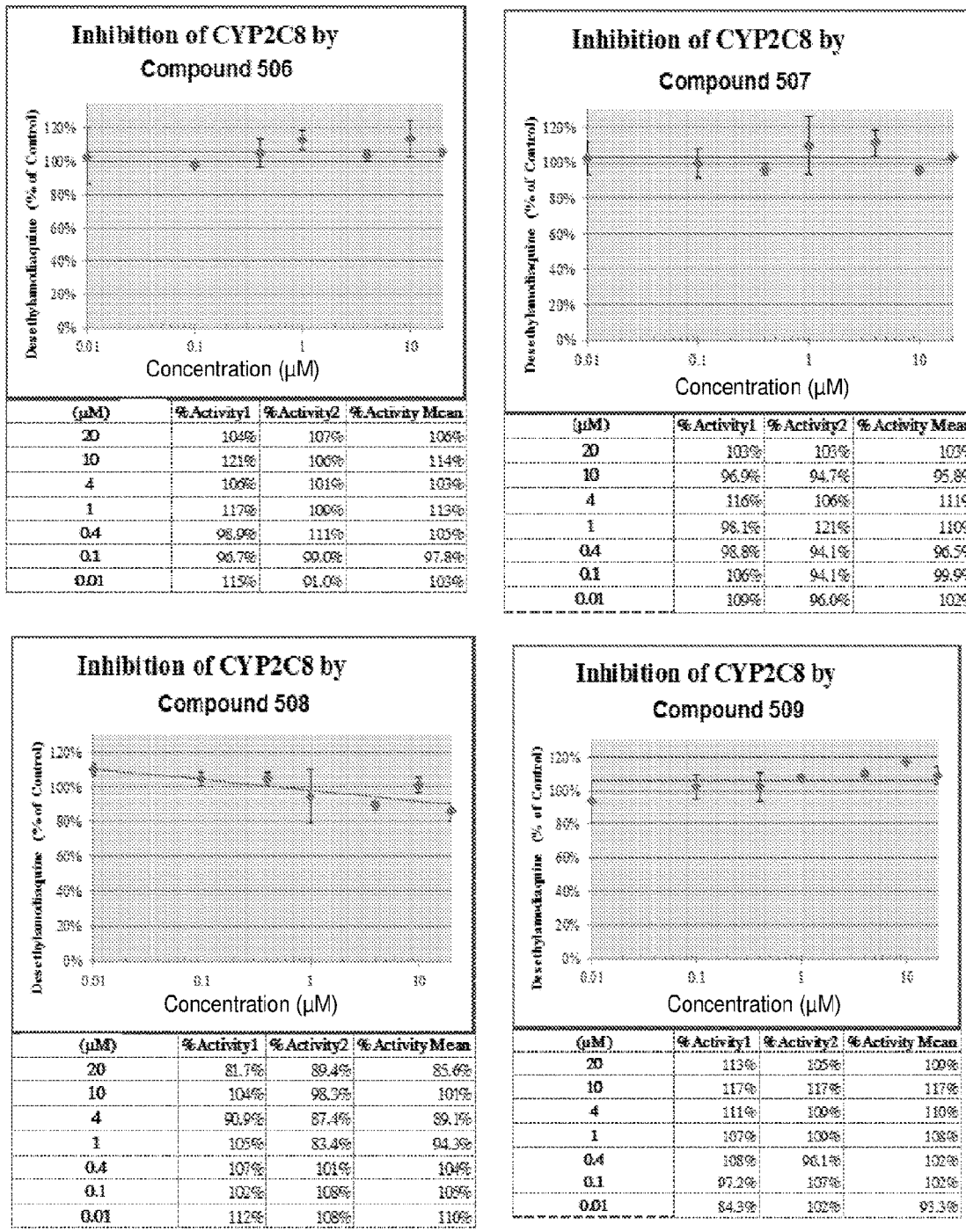
FIG. 38: Inhibition of CYP2C8 by compounds 506-509.
Figure 39:
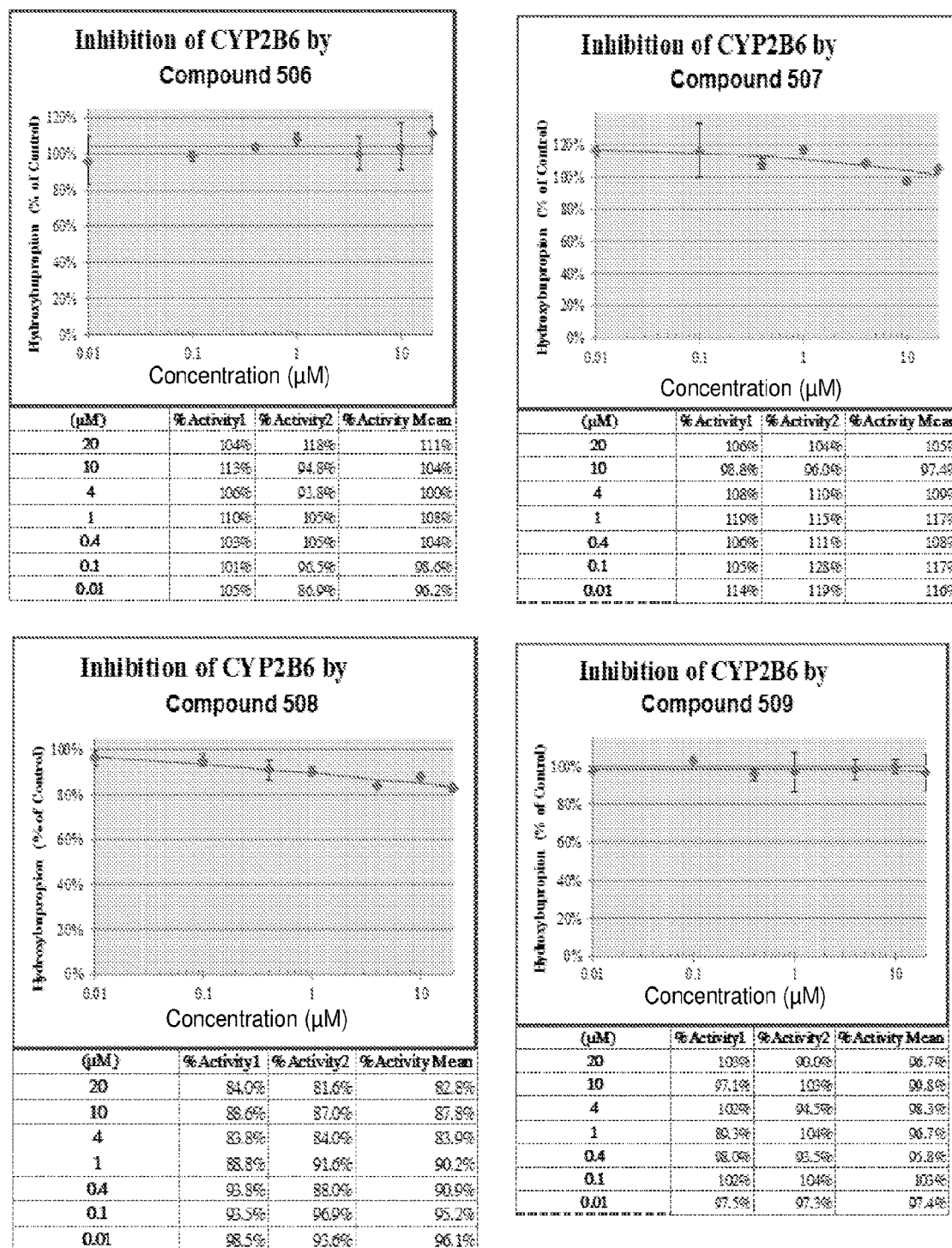
FIG. 39: Inhibition of CYP2B6 by compounds 506-509.
Figure 40:
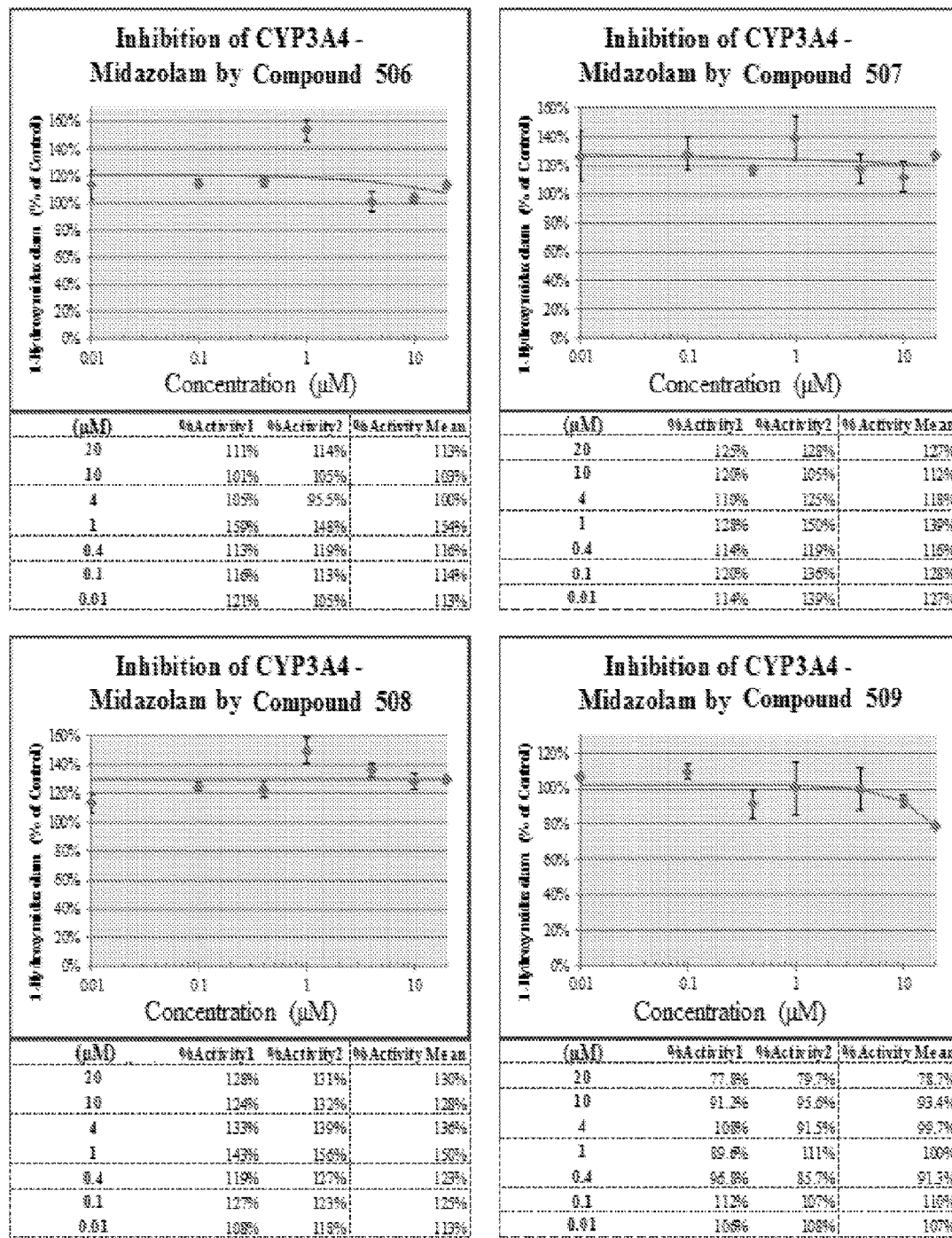
FIG. 40: Inhibition of CYP3A4—midazolam by compounds 506-509.
Figure 41:
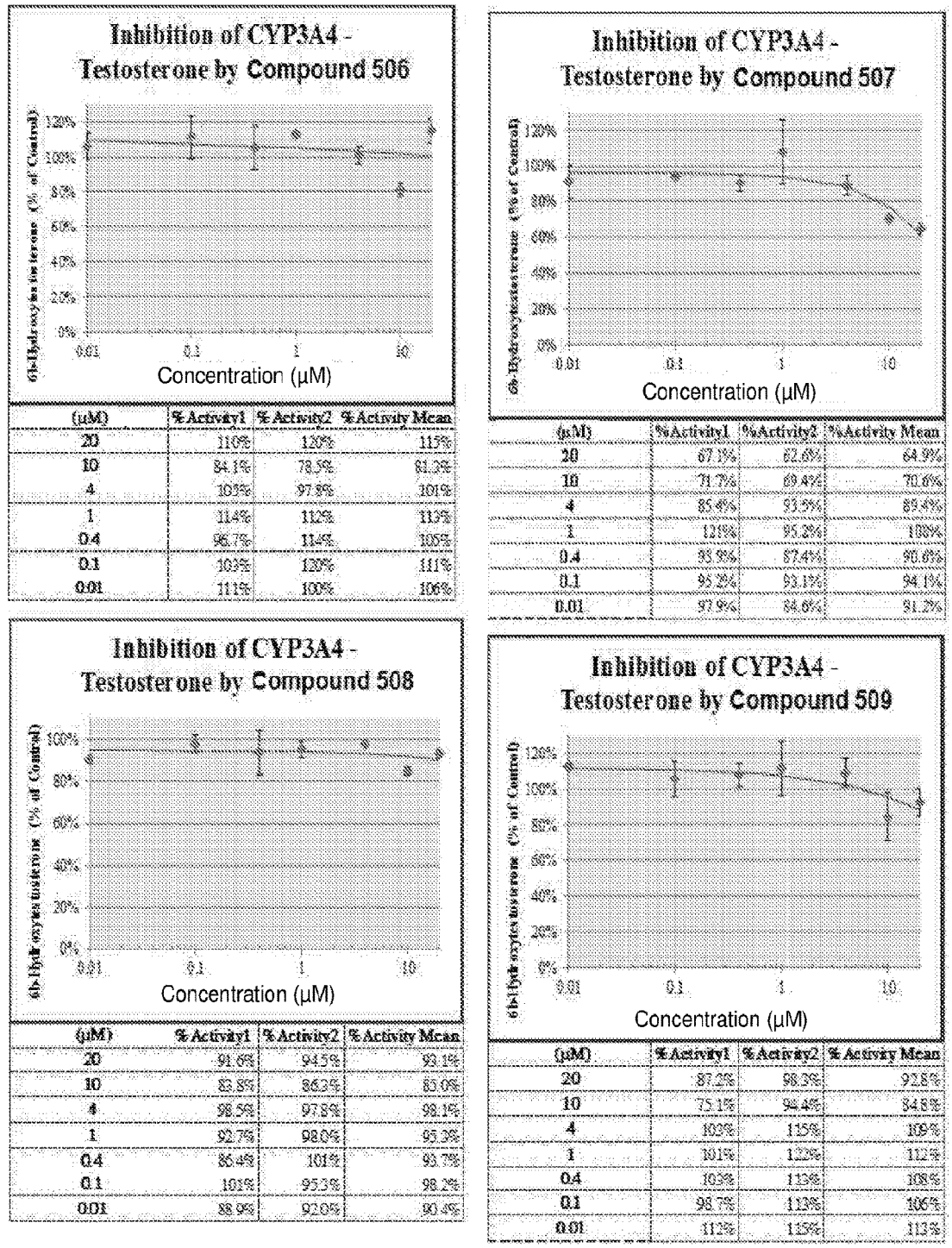
FIG. 41: Inhibition of CYP3A4—testosterone by compounds 506-509.
Figure 42:
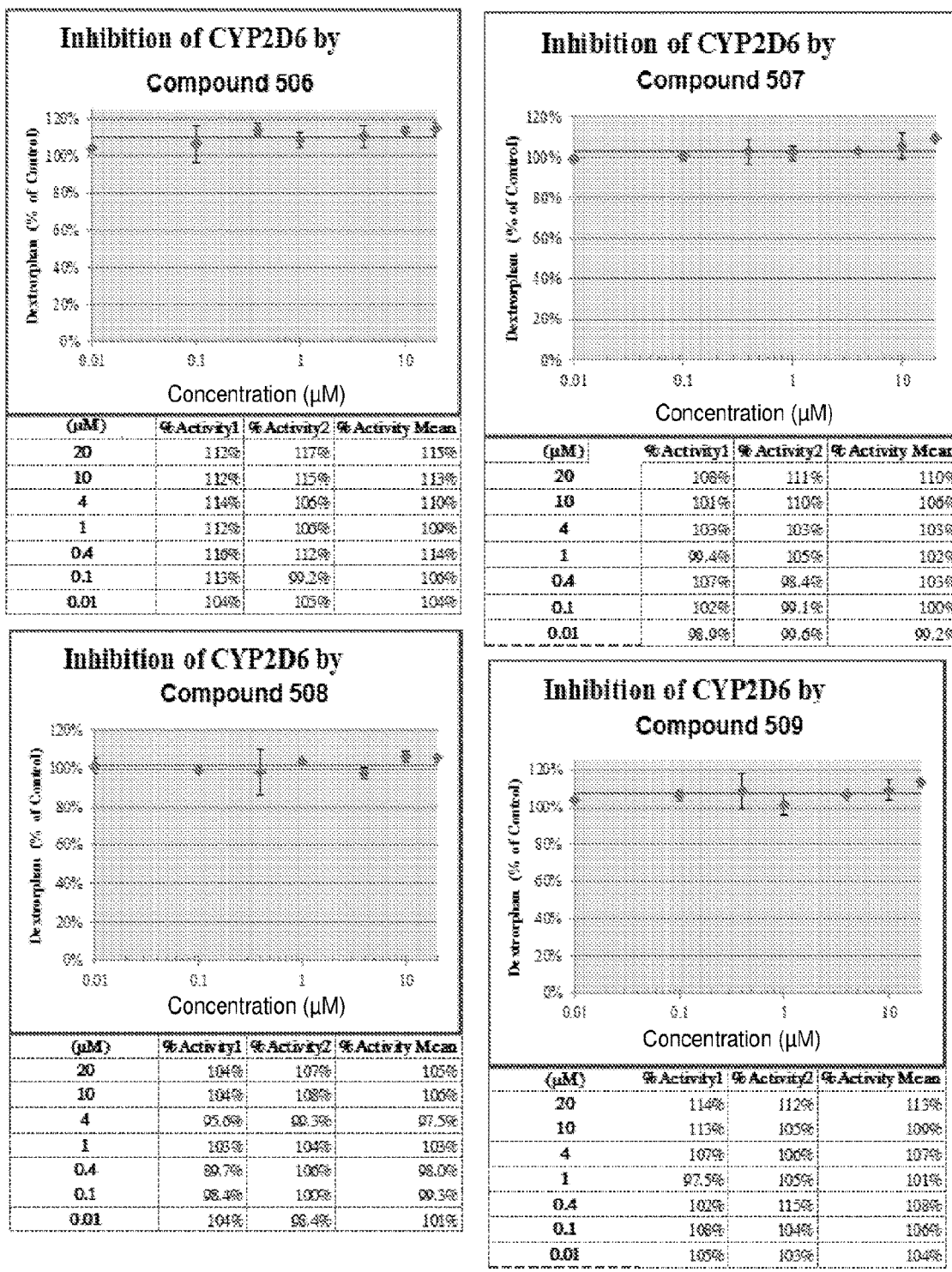
FIG. 42: Inhibition of CYP2D6 compounds 506-509.
Figure 43:
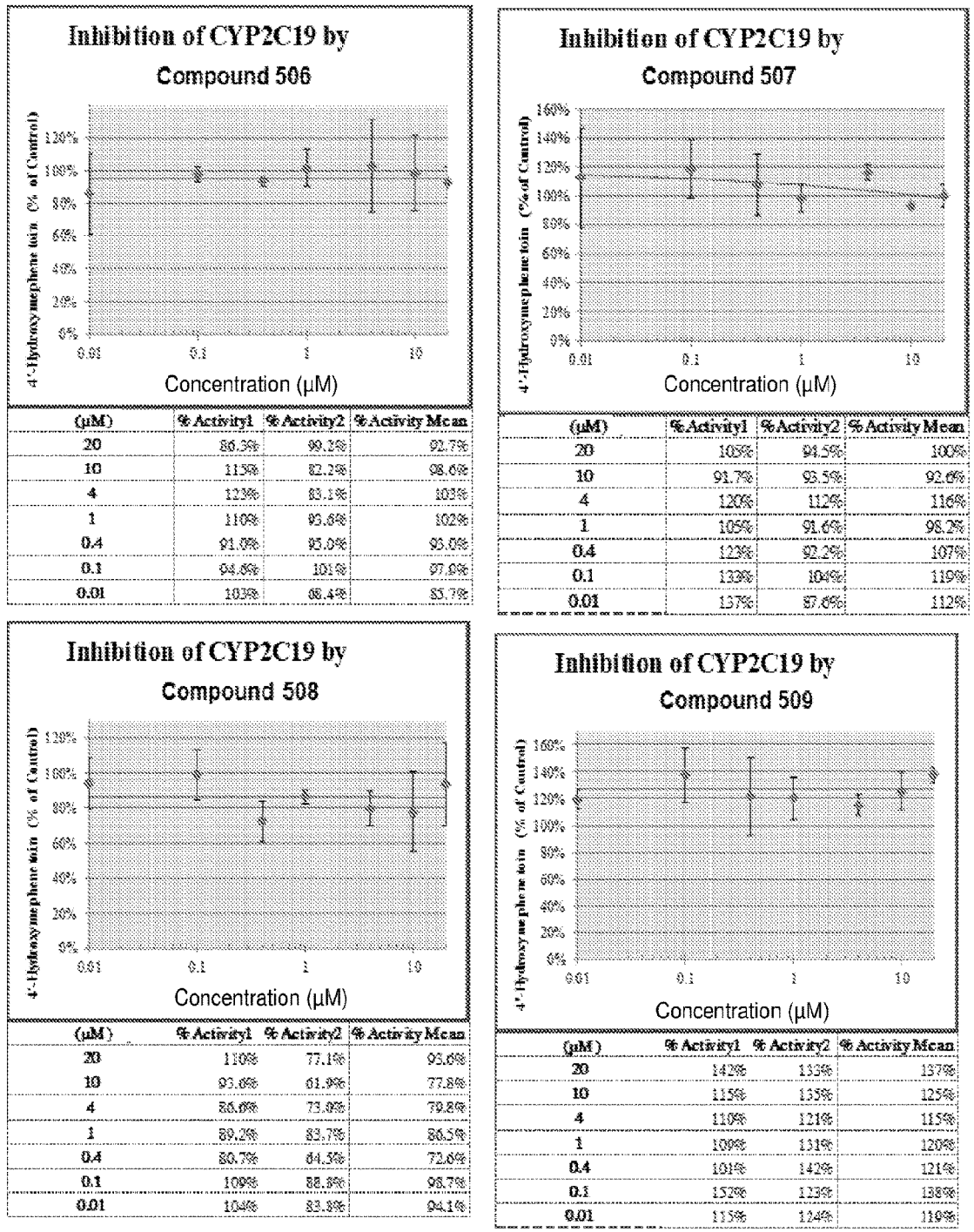
FIG. 43: Inhibition of CYP2C19 compounds 506-509.
Figure 44:
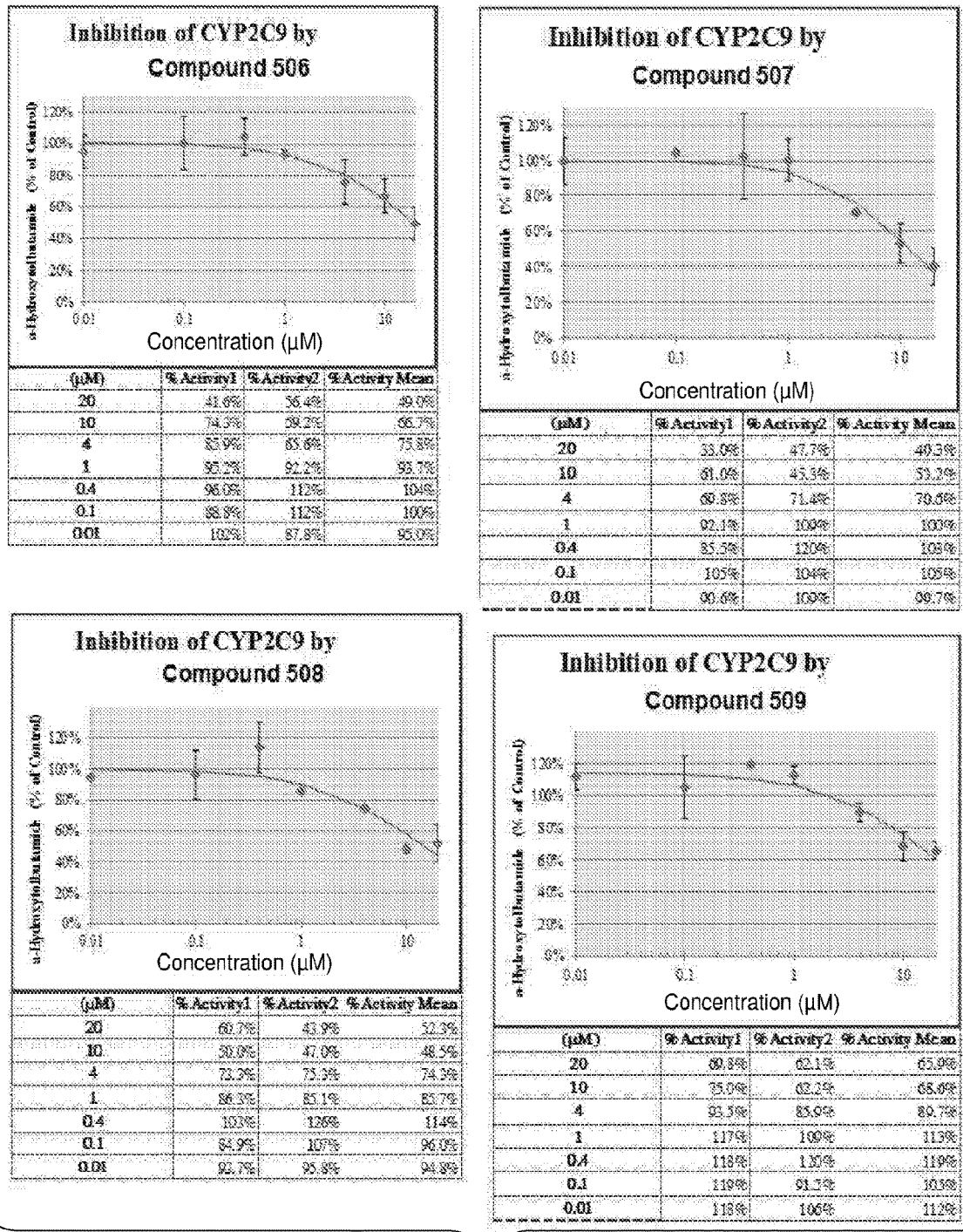
FIG. 44: Inhbition of CYP2C9 by compounds 506-509.

*avium*. FIG. 36 shows dose-response curves for compounds 513-515 against *M. abscessus*.

Further Evaluation of Compounds 506-509

Figure 37:
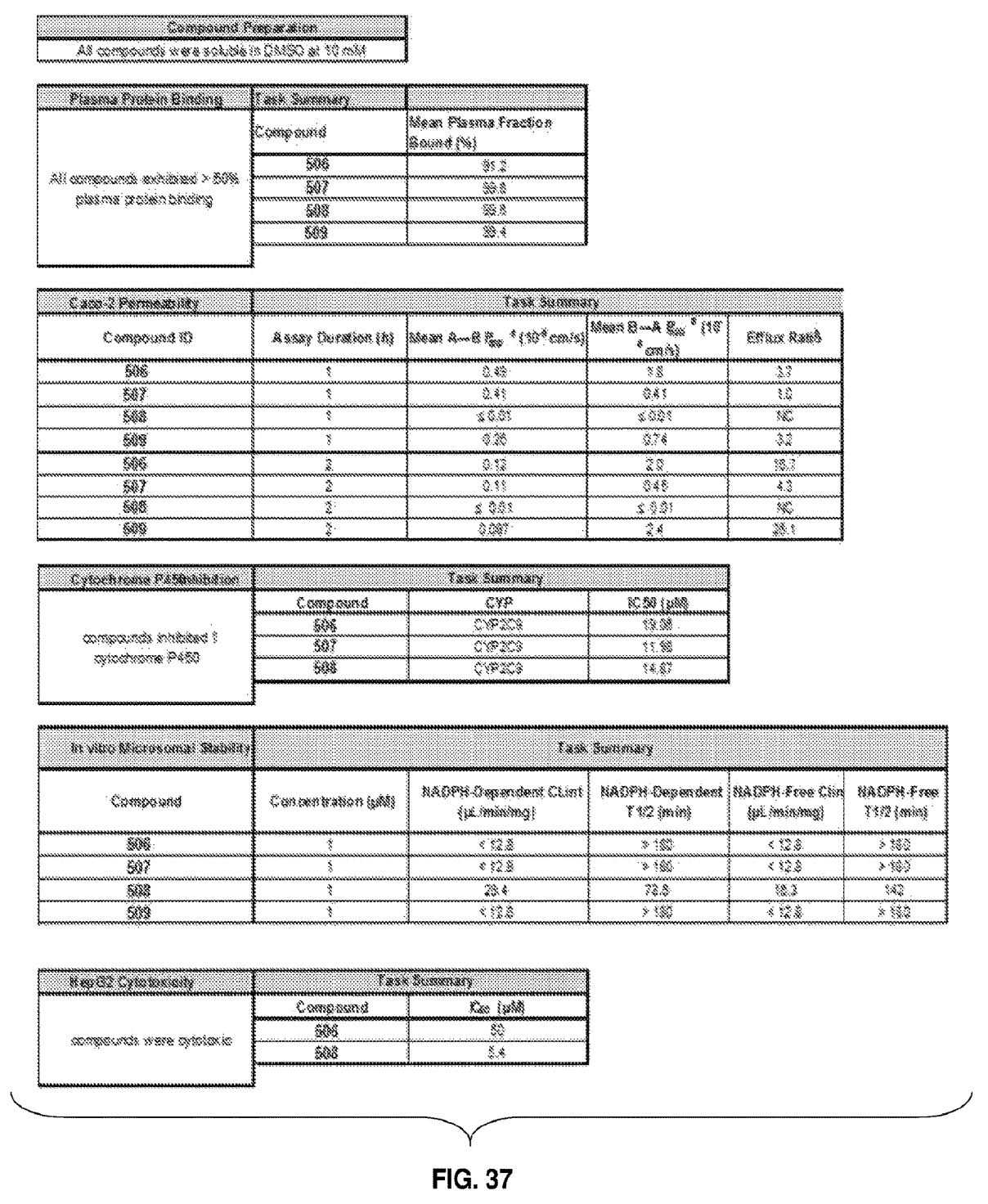

Compounds 506-509 were evaluated for plasma protein binding, Caco-2 permeability, cytochrome P450 inhibition, in vitro microsomal stability, and HepG2 cytotoxicity. FIG. 37 shows a summary of this data.

Plasma protein binding for each test compound was determined by equilibrium dialysis.

Compounds were tested using a semi-permeable membrane which separates two compartments containing protein (human plasma) and buffer. Molecules can penetrate freely, but proteins cannot pass through the membrane. Test compounds are mixed with human plasma and applied to the device; after equilibration at 37° C. with PBS, the test compound in each compartment was quantified by LC-MS/MS.

Compounds 506-509 were added to human plasma at a fixed concentration of 5 µM. The mixture was dialyzed in a RED device (Rapid Equilibrium Dialysis, Pierce) against PBS and incubated on an orbital shaker for 4 h at 37° C. Aliquots from plasma and PBS sides were collected; an equal volume of PBS was added to the plasma sample, and an equal volume of plasma was added to the PBS sample. Three volumes of methanol (containing the internal binding standard propranolol) were added to precipitate the proteins and release the compound. Each compound was tested in duplicate. Samples were centrifuged, the supernatant was recovered and analyzed by LC-MS/MS. Each experiment included warfarin as a high-binding control.

The permeability of test compounds was assessed using a Caco-2 cell monolayer. Compound permeability is measured in both directions. For A-B permeability, test compound was added to the apical side of the Caco-2 monolayer and the transport of compound to the basal side monitored. For B-A permeability, test compound was added to the basal side of the Caco-2 monolayer and the transport of the compound to the apical side monitored. Assays were run for 2 h in duplicate. The amount of compound present in each compartment was quantified by LC-MS/MS.

Caco-2 cells were trypsinized, resuspended in medium, and dispensed into a Millipore 96-well Caco-2 plate. The cells were allowed to grow and differentiate for three weeks, with feeding at 2-day intervals. For Apical to Basolateral (A→B) permeability, the compound was added to the apical (A) side and amount of permeation was determined on the basolateral (B) side; for Basolateral to Apical (B→A) permeability, the compound was added to the B side and the amount of permeation was determined on the A side. Each experiment included the control compounds atenolol (low permeability), propranolol (high permeability), and talinolol (P-gp efflux control).

The A-side contained 100 µM *Lucifer* yellow in transport buffer pH 6.5, and the B-side contained transport buffer at pH 7.4. Caco-2 cells were incubated with these buffers for either 1 h or 2 h, and the receiver side buffer was removed for analysis by LC-MS/MS. Aliquots of the cell buffers were analyzed by fluorescence to determine the transport of the impermeable dye *Lucifer* yellow to verify the Caco-2 cell monolayers were properly formed. Any deviations from control values were reported.

Compounds were tested for inhibition of six cytochrome P450 enzyme isoforms—CYP2B6, CYP2C$_8$, CYP2C$_9$, CYP2C$_{19}$, CYP2D6 and CYP3A4. For each assay, human liver microsomes are incubated with a probe substrate for each CYP isoform in the presence of compound. The formation of metabolites for each isoform is quantified by LC-MS/MS as a measure of enzyme activity. Enzyme activity was calculated and IC$_{50}$ generated. These data are shown in FIGS. 38-44.

Compounds were prepared as a 7-point dilution series in acetonitrile:DMSO (9:1). The final DMSO content in the reaction mixture was equal in all solutions used within an assay, and was <0.2%. Samples were run in duplicate. Compounds were incubated with human liver microsomes in sample buffer containing 2 mM NADPH and probe substrate in a 200 µL assay final volume. Reactions were incubated at 37° C. for the optimal time (10-60 min) and terminated by addition of methanol containing internal standard (propranolol) for analytical quantification. Samples were incubated at 4° C. for 10 min and centrifuged at 4° C. for 10 min. The supernatant was removed and the probe substrate metabolite was analyzed by LC-MS/MS. A decrease in the formation of the metabolite compared to vehicle control was used to calculate an IC$_{50}$ value (the test concentration which produces 50% inhibition).

Figure 45:
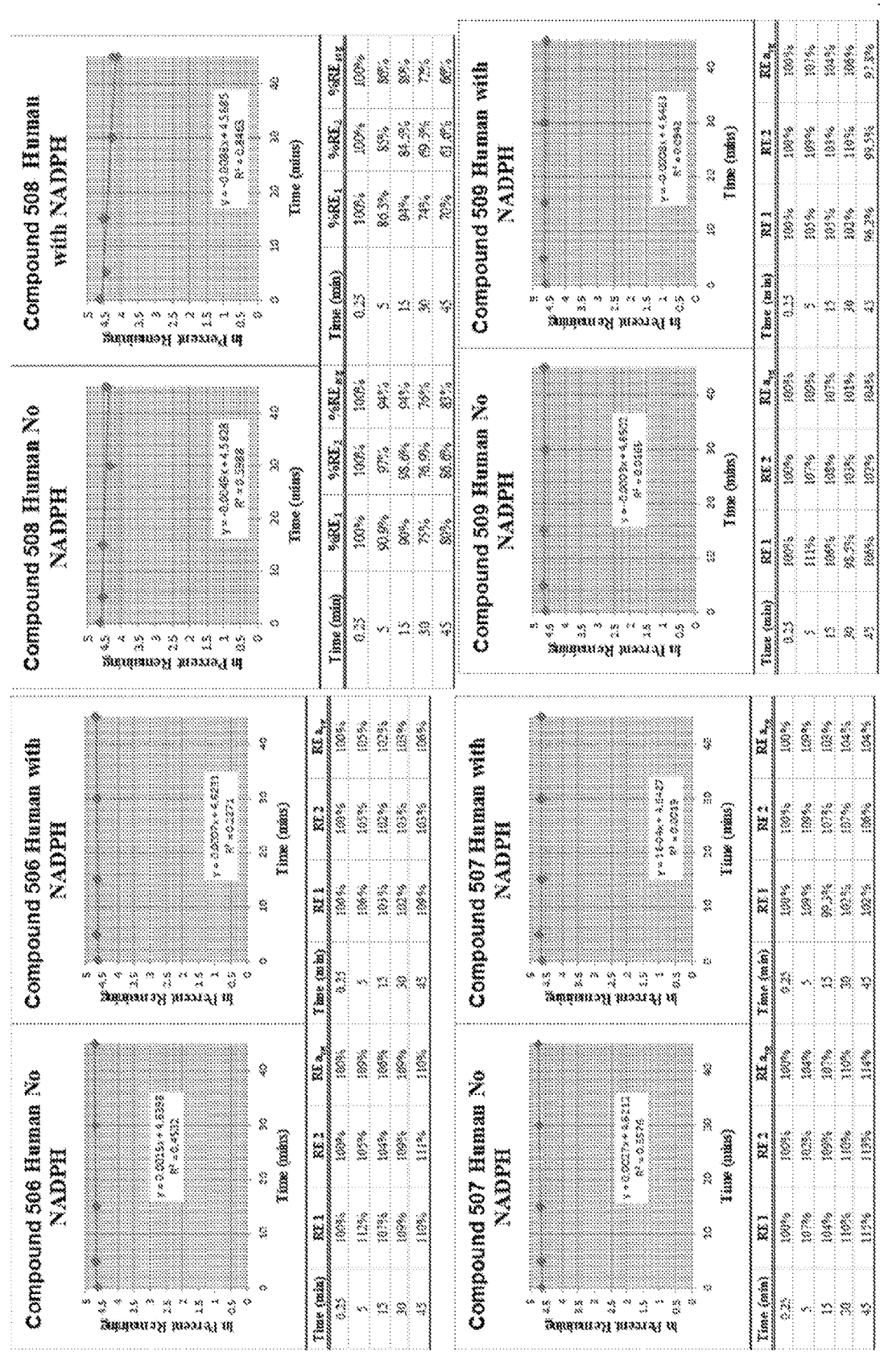
FIG. 45: Results of in vitro microsomal stability assay for compounds 506-509.

Compounds 506-509 were tested for microsomal stability using pooled human liver S9 microsomes. Microsomes are incubated with the test compound at 37° C. in the presence of the co-factor NADPH; the reaction was terminated, the supernatant recovered and test compounds quantified by LC-MS/MS. A fixed concentration of test compound was tested in duplicate at 5 timepoints and compound stability expressed as a function of time. These results are shown in FIG. 45.

The cytotoxicity of compounds 506-509 towards eukaryotic cells was determined using the human liver cells (HepG2). HepG2 cells are incubated with compounds for 72 hours and cell viability is measured. The IC$_{50}$ was determined as the concentration of compound causing a 50% decrease in viable cells after 72 h.

Figure 46:
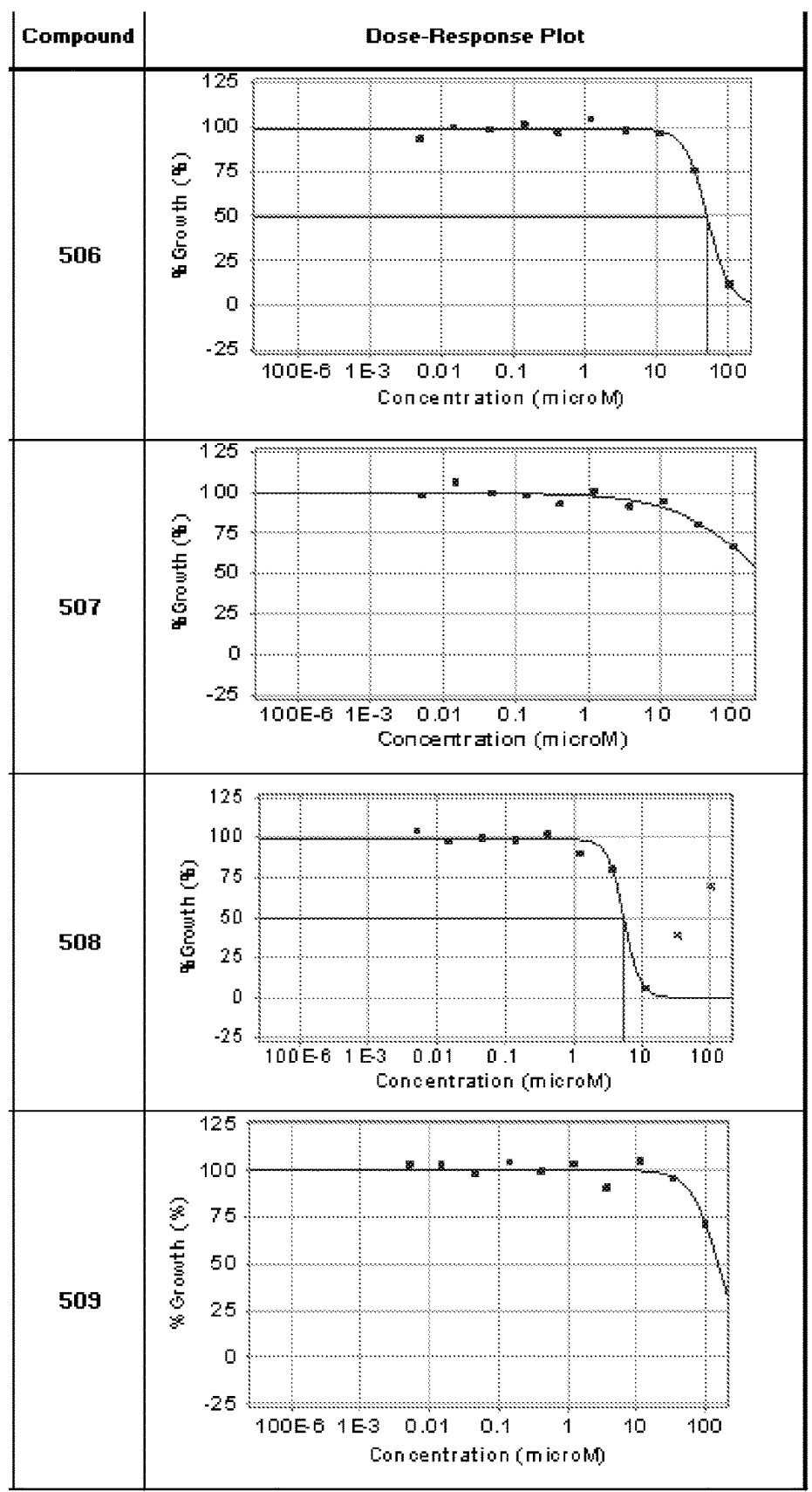
FIG. 46: Dose-response plots showing HepG2 cytotoxicity of compounds 506-509.

The cytotoxicity of compounds 506-509 was determined by measuring HepG2 cell viability after 72 h growth in the presence of test compounds. Compounds were prepared as 10-point three-fold serial dilutions in DMSO. The highest concentration of compound tested was 100 µM where compounds were soluble in DMSO at 10 mM. HepG2 cells were cultured in complete DMEM, inoculated into 384-well assay plates and incubated for 24 h at 37° C., 5% CO$_2$. Compounds were added and cells were cultured for a further 72 h. The final DMSO concentration was 1%. Cell viability was determined using the CellTiter-Glo® Luminescent Cell Viability Assay (Promega) and measuring relative luminescent units (RLU). The dose response curve was fitted using the Levenberg-Marquardt algorithm. The IC$_{50}$ was defined as the compound concentration that produced 50% decrease in viable cells. Each run included staurosporine as a control. These results are shown in FIG. 46.

Compounds were incubated with human liver microsomes at 37° C. in duplicate. Each reaction contained 0.3 mg/mL human microsomal protein in assay buffer. Samples were removed at 0, 5, 15, 30, and 45 minutes, mixed with an equal volume of stop solution (containing propranolol as an internal standard), and incubated for >10 min at −20° C. An additional volume of water was added, samples were centrifuged to remove precipitated protein and the supernatants were analyzed by LC-MS/MS to quantitate the remaining parent compound. A control reaction omitting NADPH (control buffer) was performed for each compound to detect NADPH-free degradation. Verapamil and dextromethorphan were included as control compounds.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the com-

What is claimed is:
1. A compound of Formula III:
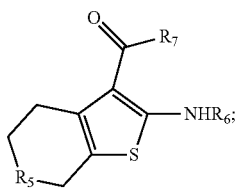
Formula III
wherein $R_5$ is NEt, $R_6$ is $COPhF_5$, and $R_7$ is $C_1$-$C_8$ alkyl, $C_1$-$C_8$ alkoxy, or $C_1$-$C_8$ alkylamino.
2. A compound of Formula 506:
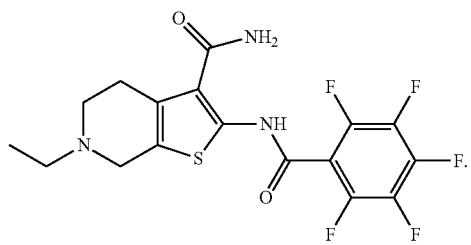
506
3. A compound of Formula 507:
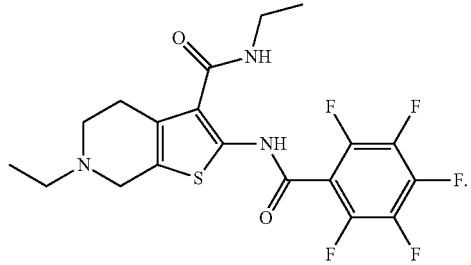
507
4. A compound of Formula 508:
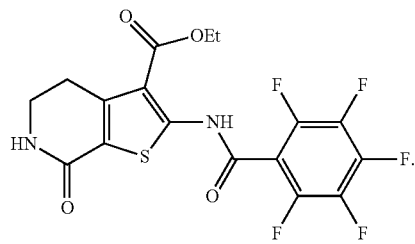
508
5. A compound of Formula 509:
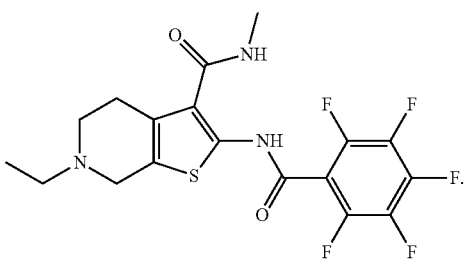
509
6. A compound of Formula 510:
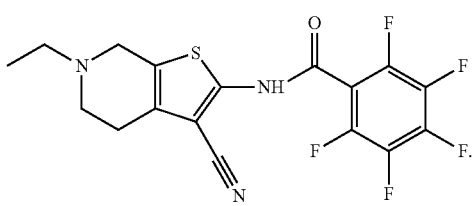
510
7. A compound of Formula 511:
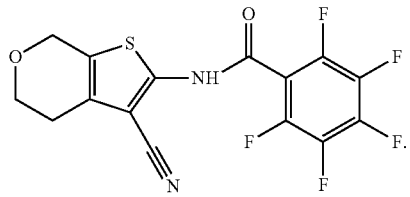
511
8. A compound of Formula 512:
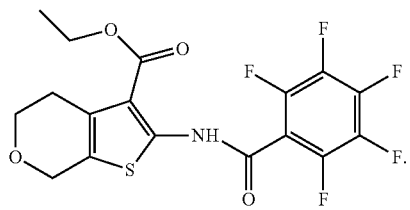
512
9. A compound of Formula 513:
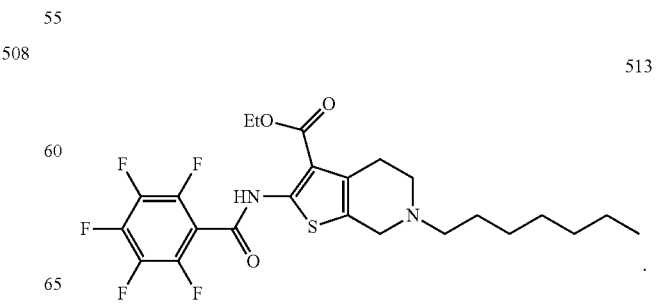
513

10. A compound of Formula 514:

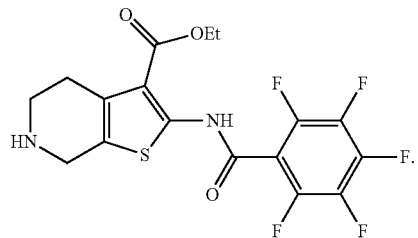

11. A compound of Formula 515:

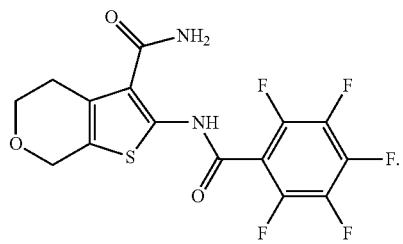

12. A compound of Formula V:

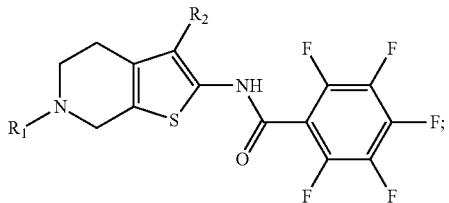

wherein:

$R_1$ is H, or substituted or unsubstituted $C_1$-$C_8$ acyl, $C_1$-$C_8$ alkyl, $C_1$-$C_8$ aminoalkyl, $C_1$-$C_8$ alkenyl, or Ph; and $R_2$ is a substituted or substituted tetrazole, oxadiazole, thiadiazole, thiadiazole ketone, oxadiazolethione, amide, acylurea, or oxadiazole ketone;

and salts, stereoisomers, racemates, hydrates, solvates, prodrugs, and polymorphs thereof.

* * * * *